US008546407B2

(12) United States Patent
Berdini et al.

(10) Patent No.: US 8,546,407 B2
(45) Date of Patent: Oct. 1, 2013

(54) ORTHO-CONDENSED PYRIDINE AND PYRIMIDINE DERIVATIVES (E.G., PURINES) AS PROTEIN KINASES INHIBITORS

(75) Inventors: Valerio Berdini, Cambridge (GB); Robert George Boyle, Cambridge (GB); Gordon Saxty, Cambridge (GB); David Winter Walker, Cambridge (GB); Steven John Woodhead, Cambridge (GB); Paul Graham Wyatt, Perth (GB); Alastair Donald, Abingdon (GB); John Caldwell, Sutton (GB); Ian Collins, Redhill (GB); Tatiana Faria Da Fonseca, Sunburg-on-Themes (GB)

(73) Assignees: Astex Therapeutics Limited, Cambrdige (GB); The Institute of Cancer Research: Royal Cancer Hospital, London (GB); Cancer Research Technology Limited, London (GB)

( * ) Notice: Subject to any disclaimer, the term of this patent is extended or adjusted under 35 U.S.C. 154(b) by 1255 days.

(21) Appl. No.: 11/577,963

(22) PCT Filed: Oct. 25, 2005

(86) PCT No.: PCT/GB2005/004119
§ 371 (c)(1),
(2), (4) Date: Jun. 5, 2009

(87) PCT Pub. No.: WO2006/046024
PCT Pub. Date: May 4, 2006

(65) Prior Publication Data
US 2009/0247538 A1 Oct. 1, 2009

Related U.S. Application Data

(60) Provisional application No. 60/621,821, filed on Oct. 25, 2004, provisional application No. 60/684,119, filed on May 24, 2005.

(30) Foreign Application Priority Data

Oct. 25, 2004 (GB) .................................. 0423655.0

(51) Int. Cl.
*C07D 487/04* (2006.01)
*A61K 31/519* (2006.01)
*A61P 35/00* (2006.01)

(52) U.S. Cl.
USPC ......... 514/265.1; 544/280; 546/113; 514/300

(58) Field of Classification Search
USPC ..................................... 544/280; 514/265.1
See application file for complete search history.

(56) References Cited

U.S. PATENT DOCUMENTS 6,162,804 A    12/2000  Bilodeau et al.

6,432,947 B1    8/2002  Arnaiz et al.
2002/0094974 A1  7/2002  Castelhano et al.
2003/0045536 A1  3/2003  Castelhano et al.
2003/0073708 A1  4/2003  Castelhano et al.
2003/0139427 A1  7/2003  Castelhano et al.
2004/0082598 A1  4/2004  Castelhano et al.
2004/0082599 A1  4/2004  Castelhano et al.
2006/0111362 A1  5/2006  Kira et al.
2006/0148844 A1  7/2006  Nakade et al.
2007/0135402 A1  6/2007  Habashita et al.
2008/0070936 A1  3/2008  Castelhano et al.

FOREIGN PATENT DOCUMENTS

| EP | 1444982 A1 | 8/2004 |
| GB | 1047935 A | 11/1966 |
| WO | 9500516 | 1/1995 |
| WO | 9738665 | 10/1997 |
| WO | 9907703 | 2/1999 |
| WO | 9962908 | 12/1999 |
| WO | 9965908 | 12/1999 |
| WO | 9965909 | 12/1999 |
| WO | 0075145 A1 | 12/2000 |
| WO | 0107050 A1 | 2/2001 |
| WO | 0146196 A1 | 6/2001 |
| WO | 0218348 A2 | 3/2002 |
| WO | 02057267 A1 | 7/2002 |
| WO | 03057696 A1 | 7/2003 |
| WO | 03088908 A2 | 10/2003 |
| WO | 2004014850 A2 | 2/2004 |

(Continued)

OTHER PUBLICATIONS

Vippagunta, S.R., (Adv. Drug. Delivery Rev., 2001, 48, pp. 3-26).*
Barnett et al : "The Akt/PKB Family of 1-15 Protein Kinases : A Review of Small Molecule Inhibitors and Progress Towards Target Validation" Current Topics in Medicinal Chemistry, Bentham Science Publishers, Hilversum, NL, vol. 5, No. 2, Jan. 1, 2005, pp. 109-125, XP009074071, ISSN : 1568-0266.
Quintela J M et al "Pyrazolopyrimidines: synthesis, effect on histamine release from rat peritoneal mast cells and cytotoxic activity" European Journal of Medicinal Chemistry, Elsevier, Paris vol. 36, No. 4, May 2001, pp. 321-322 (ISSN 0223-5234).
"Substances with antineoplastic activity II. 6-carboxyalkylthiopurines", M. Semonsky et al, Collection of Czechoslovakian Chemical Communications, (1960), 25, 1091-1099.

(Continued)

*Primary Examiner* — Susanna Moore
(74) *Attorney, Agent, or Firm* — Heslin Rothenberg Farley & Mesiti P.C.

(57) ABSTRACT

The invention provides a compound for use as a protein kinase B inhibitor, the compound being a compound of the formula (Ic) or salts, tautomers or N-oxides thereof.

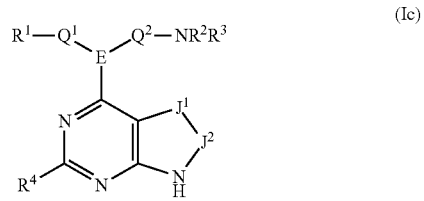

(Ic)

18 Claims, No Drawings

(56) References Cited

FOREIGN PATENT DOCUMENTS

| | | | |
|---|---|---|---|
| WO | 2004037823 A1 | 5/2004 |
| WO | 2004043380 A2 | 5/2004 |
| WO | 2004074287 A1 | 9/2004 |
| WO | 2004080463 A1 | 9/2004 |
| WO | 2004094426 A1 | 11/2004 |
| WO | 2005003128 A1 | 1/2005 |
| WO | 2005020921 A2 | 3/2005 |
| WO | 2005026149 A1 | 3/2005 |
| WO | 2005044181 A2 | 5/2005 |
| WO | 2005051304 A2 | 6/2005 |
| WO | 2005117909 A2 | 12/2005 |
| WO | 2006046023 A1 | 5/2006 |
| WO | 2006046024 A1 | 5/2006 |
| WO | 2006071819 A1 | 7/2006 |
| WO | 2006075094 A2 | 7/2006 |
| WO | 2006075095 A2 | 7/2006 |
| WO | 2006091450 A1 | 8/2006 |
| WO | 2006135639 A1 | 12/2006 |
| WO | 2007007919 A2 | 1/2007 |
| WO | 2007025090 A2 | 3/2007 |
| WO | 2007084667 A2 | 7/2007 |
| WO | 2007125310 A2 | 11/2007 |
| WO | 2007125315 A2 | 11/2007 |
| WO | 2007125320 A1 | 11/2007 |
| WO | 2007125321 A2 | 11/2007 |
| WO | 2007125325 A1 | 11/2007 |
| WO | 2008075109 A1 | 6/2008 |
| WO | 2008075110 A1 | 6/2008 |
| WO | 2009047563 A1 | 4/2009 |

OTHER PUBLICATIONS

"Potential Purine Antagonists. XIV. Synthesis of some 4-(substitutedamino)pyrazolo-[3,4-d]pyrimidines", C. W. Noell & R. K. Robins, J. Org. Chem., (1958), 23, 1547-1550.

"Weitere Untersuchungen an $N^6$-Derivaten des Adenins" ("Further studies on N6-derivatives of adenine"), H. Lettre & H. Ballweg, Naturwissenschaften, (1958), 45, 364.

"Structure-activity relationships among purines related to 6-mercaptopurine" Cancer Research, (1958), 18, 445-456.

"Synthesis of potent anticancer agents" K Panagopolous et al Arzneimittel-Forschung, (1965), 15(3), 204-207.

Chemical Abstract No. 106:196130 & JP 62010085A2 (Yoshitomi), Jan. 19, 1987.

Calabresi, P. and Chabner, B.A. Section IX Chemotherapy of Neoplastic Diseases—Introduction, Goodman and Gillman's The Pharmacologial Basis of Therapeutics, (Hardman, J.G, Limbird, L.E, Molinoff, P.B., Ruddon, R.W, and Gilman, A.G.,eds) McGraw-Hill, New York, 2001, 1381-1388.

Dowling RJ, Topisirovic I, Fonseca BD, Sonenberg N, "Dissecting the role of mTOR: lessons from mTOR inhibitors", Biochim Biophys Acta. Mar. 2010;1804(3):433-9.

Emory University, Cancer Quest.org, http://www.cancerquest.org/stages-tumor-progression.html, Jul. 2, 2010.

James J. Gibbons, Robert T. Abraham, Ker Yu "Mammalian Target of Rapamycin: Discovery of Rapamycin Reveals a Signaling Pathway Important for Normal and Cancer Cell Growth" Seminars on Oncology, vol. 36, Supplement 3 , pp. S3-S17, Dec. 2009.

National Institute on Aging, NIH, "Age page" http://www.nia.nih.gov/HealthInformation/Publications/cancer.htm, Jul. 2, 2010.

Olson MF, "Applications for Rock kinase inhibition", Current opinion in Cell Biology, Apr. 2008 20(2):242-8.

Pollard JR and Mortimer M, "Discovery and development of aurora kinase inhibitors as anticancer agents" J Med Chem. May 14, 2009;52(9):2629-51.

Vippagunta SR, "Crystalline solids", Adv Drug Deliv Rev. May 16, 2001;48(1):3-26.

Kenneth W Kinzler and Bert Vogelstein, "The Genetic Basis of Human Cancer", 2002, p. 3.

Luke, Richard; "Discovery of AZD5363—An orally bioavailable, potent inhibitor of AKT kinases;" PowerPoint talk slides; May 21, 2012; Oncology Innovative Medicines, AstraZeneca, Alderley Park, UK.

Luke et al. "Discovery of AZD5363, an orally bioavailable, potent, ATP-competitive inhibitor of AKT kinases;" American Association for Cancer Research poster; Apr. 2011; Oncology iMed, AstraZeneca, Alderley Park, Macclesfield, UK.

Davies et al. "CCT129254 (AT11854) is a well tolerated, orally bioavailable inhibitor of AKT/PKB with pharmacodynamic and antitumor activity in a range of preclinical models;" American Association for Cancer Research poster; Nov. 2009; Astra Zeneca, Alderley Park, Macclesfield, UK; Astex Therapeutics, Cambridge, UK; Cancer Research UK Centre for Cancer Therapeutics at The Institute for Cancer Research, Sutton, UK.

* cited by examiner

ORTHO-CONDENSED PYRIDINE AND PYRIMIDINE DERIVATIVES (E.G., PURINES) AS PROTEIN KINASES INHIBITORS

CROSS REFERENCE TO RELATED APPLICATIONS

This application is a 371 filing of PCT International application no. PCT/GB2005/004119 filed Oct. 25, 2005, published in English as WO 2006/046024 on May 4, 2006, and claims the priority of GB Application No. 0423655.0 filed Oct. 25, 2004 and U.S. Application Nos. 60/621,821 filed Oct. 25, 2004 and 60/684,119 filed May 24, 2005, the disclosures of which are hereby incorporated by reference in their entirety.

TECHNICAL FIELD

This invention relates to purine, purinone and deazapurine and deazapurinone compounds that inhibit or modulate the activity of protein kinase B (PKB) and protein kinase A (PKA), to the use of the compounds in the treatment or prophylaxis of disease states or conditions mediated by PKB and PKA, and to novel compounds having PKB and PKA inhibitory or modulating activity. Also provided are pharmaceutical compositions containing the compounds and novel chemical intermediates.

BACKGROUND OF THE INVENTION

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J,* 9:576-596 (1995); Knighton, et al., *Science,* 253:407-414 (1991); Hiles, et al., *Cell,* 70:419-429 (1992); Kunz, et al., *Cell,* 73:585-596 (1993); Garcia-Bustos, et al., *EMBO J.,* 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Apoptosis or programmed cell death is an important physiological process which removes cells no longer required by an organism. The process is important in early embryonic growth and development allowing the non-necrotic controlled breakdown, removal and recovery of cellular components. The removal of cells by apoptosis is also important in the maintenance of chromosomal and genomic integrity of growing cell populations. There are several known checkpoints in the cell growth cycle at which DNA damage and genomic integrity are carefully monitored. The response to the detection of anomalies at such checkpoints is to arrest the growth of such cells and initiate repair processes. If the damage or anomalies cannot be repaired then apoptosis is initiated by the damaged cell in order to prevent the propagation of faults and errors. Cancerous cells consistently contain numerous mutations, errors or rearrangements in their chromosomal DNA. It is widely believed that this occurs in part because the majority of tumours have a defect in one or more of the processes responsible for initiation of the apoptotic process. Normal control mechanisms cannot kill the cancerous cells and the chromosomal or DNA coding errors continue to be propagated. As a consequence restoring these pro-apoptotic signals or suppressing unregulated survival signals is an attractive means of treating cancer.

The signal transduction pathway containing the enzymes phosphatidylinositol 3-kinase (PI3K), PDK1 and PKB amongst others, has long been known to mediate increased resistance to apoptosis or survival responses in many cells. There is a substantial amount of data to indicate that this pathway is an important survival pathway used by many growth factors to suppress apoptosis. The enzymes of the PI3K family are activated by a range of growth and survival factors e.g. EGF, PDGF and through the generation of polyphosphatidylinositols, initiates the activation of the downstream signalling events including the activity of the kinases PDK1 and protein kinase B (PKB) also known as akt. This is also true in host tissues, e.g. vascular endothelial cells as well as neoplasias. PKB is a protein ser/thr kinase consisting of a kinase domain together with an N-terminal PH domain and C-terminal regulatory domain. The enzyme $PKB_{alpha}$ (akt1) itself is phosphorylated on Thr 308 by PDK1 and on Ser 473 by a kinase referred to as PDK2, whereas $PKB_{beta}$ (akt2) is phosphorylated on Thr 309 and on Ser 474, and $PKB_{gamma}$ (akt3) is phosphorylated on Thr 305 and on Ser 472.

At least 10 kinases have been suggested to function as a Ser 473 kinase including mitogen-activated protein (MAP) kinase-activated protein kinase-2 (MK2), integrin-linked kinase (ILK), p38 MAP kinase, protein kinase Calpha (PKCalpha), PKCbeta, the NIMA-related kinase-6 (NEK6), the mammalian target of rapamycin (mTOR), the double-stranded DNA-dependent protein kinase (DNK-PK), and the ataxia telangiectasia mutated (ATM) gene product. Available data suggest that multiple systems may be used in cells to regulate the activation of PKB. Full activation of PKB requires phosphorylation at both sites whilst association between PIP3 and the PH domain is required for anchoring of the enzyme to the cytoplasmic face of the lipid membrane providing optimal access to substrates.

Activated PKB in turns phosphorylates a range of substrates contributing to the overall survival response. Whilst we cannot be certain that we understand all of the factors responsible for mediating the PKB dependent survival response, some important actions are believed to be phosphorylation and inactivation of the pro-apoptotic factor BAD and caspase 9, phosphorylation of Forkhead transcription factors e.g. FKHR leading to their exclusion from the nucleus, and activation of the NfkappaB pathway by phosphorylation of upstream kinases in the cascade.

In addition to the anti-apoptotic and pro-survival actions of the PKB pathway, the enzyme also plays an important role in promoting cell proliferation. This action is again likely to be mediated via several actions, some of which are thought to be phosphorylation and inactivation of the cyclin dependent kinase inhibitor of $p21^{CiP1/WAF1}$, and phosphorylation and activation of mTOR, a kinase controlling several aspects of cell size, growth and protein translation.

The phosphatase PTEN which dephosphorylates and inactivates polyphosphatidylinositols is a key tumour suppressor protein which normally acts to regulate the PI3K/PKB survival pathway. The significance of the PI3K/PKB pathway in tumourigenesis can be judged from the observation that PTEN is one of the most common targets of mutation in human tumours, with mutations in this phosphatase having been found in ~50% or more of melanomas (Guldberg et al 1997, Cancer Research 57, 3660-3663) and advanced prostate cancers (Cairns et al 1997 Cancer Research 57, 4997). These observations and others suggest that a wide range of tumour types are dependent on the enhanced PKB activity for growth and survival and would respond therapeutically to appropriate inhibitors of PKB.

There are 3 closely related isoforms of PKB called alpha, beta and gamma, which genetic studies suggest have distinct but overlapping functions. Evidence suggests that they can all independently play a role in cancer. For example PKB beta has been found to be over-expressed or activated in 10-40% of ovarian and pancreatic cancers (Bellacosa et al 1995, Int. J. Cancer 64, 280-285; Cheng et al 1996, PNAS 93, 3636-3641; Yuan et al 2000, Oncogene 19, 2324-2330), PKB alpha is amplified in human gastric, prostate and breast cancer (Staal 1987, PNAS 84, 5034-5037; Sun et al 2001, Am. J. Pathol. 159, 431-437) and increased PKB gamma activity has been observed in steroid independent breast and prostate cell lines (Nakatani et al 1999, J. Biol. Chem. 274, 21528-21532).

The PKB pathway also functions in the growth and survival of normal tissues and may be regulated during normal physiology to control cell and tissue function. Thus disorders associated with undesirable proliferation and survival of normal cells and tissues may also benefit therapeutically from treatment with a PKB inhibitor. Examples of such disorders are disorders of immune cells associated with prolonged expansion and survival of cell population leading to a prolonged or up regulated immune response. For example, T and B lymphocyte response to cognate antigens or growth factors such as interferon gamma activates the PI3K/PKB pathway and is responsible for maintaining the survival of the antigen specific lymphocyte clones during the immune response. Under conditions in which lymphocytes and other immune cells are responding to inappropriate self or foreign antigens, or in which other abnormalities lead to prolonged activation, the PKB pathway contributes an important survival signal preventing the normal mechanisms by which the immune response is terminated via apoptosis of the activated cell population. There is a considerable amount of evidence demonstrating the expansion of lymphocyte populations responding to self antigens in autoimmune conditions such as multiple sclerosis and arthritis. Expansion of lymphocyte populations responding inappropriately to foreign antigens is a feature of another set of conditions such as allergic responses and asthma. In summary inhibition of PKB could provide a beneficial treatment for immune disorders.

Other examples of inappropriate expansion, growth, proliferation, hyperplasia and survival of normal cells in which PKB may play a role include but are not limited to atherosclerosis, cardiac myopathy and glomerulonephritis.

In addition to the role in cell growth and survival, the PKB pathway functions in the control of glucose metabolism by insulin. Available evidence from mice deficient in the alpha and beta isoforms of PKB suggests that this action is mediated by the beta isoform primarily. As a consequence, modulators of PKB activity may also find utility in diseases in which there is a dysfunction of glucose metabolism and energy storage such as diabetes, metabolic disease and obesity.

Cyclic AMP-dependent protein kinase (PKA) is a serine/threonine protein kinase that phosphorylates a wide range of substrates and is involved in the regulation of many cellular processes including cell growth, cell differentiation, ion-channel conductivity, gene transcription and synaptic release of neurotransmitters. In its inactive form, the PKA holoenzyme is a tetramer comprising two regulatory subunits and two catalytic subunits.

PKA acts as a link between G-protein mediated signal transduction events and the cellular processes that they regulate. Binding of a hormone ligand such as glucagon to a transmembrane receptor activates a receptor-coupled G-protein (GTP-binding and hydrolyzing protein). Upon activation, the alpha subunit of the G protein dissociates and binds to and activates adenylate cyclase, which in turn converts ATP to cyclic-AMP (cAMP). The cAMP thus produced then binds to the regulatory subunits of PKA leading to dissociation of the associated catalytic subunits. The catalytic subunits of PKA, which are inactive when associated with the regulatory sub-units, become active upon dissociation and take part in the phosphorylation of other regulatory proteins.

For example, the catalytic sub-unit of PKA phosphorylates the kinase Phosphorylase Kinase which is involved in the phosphorylation of Phosphorylase, the enzyme responsible for breaking down glycogen to release glucose. PKA is also involved in the regulation of glucose levels by phosphorylating and deactivating glycogen synthase. Thus, modulators of PKA activity (which modulators may increase or decrease PKA activity) may be useful in the treatment or management of diseases in which there is a dysfunction of glucose metabolism and energy storage such as diabetes, metabolic disease and obesity.

PKA has also been established as an acute inhibitor of T cell activation. Anndahl et al, have investigated the possible role of PKA type I in HIV-induced T cell dysfunction on the basis that T cells from HIV-infected patients have increased levels of cAMP and are more sensitive to inhibition by cAMP analogues than are normal T cells. From their studies, they concluded that increased activation of PKA type I may contribute to progressive T cell dysfunction in HIV infection and that PKA type I may therefore be a potential target for immunomodulating therapy.-Aandahl, E. M., Aukrust, P., Skålhegg, B. S., Müller, F., Frøland, S. S., Hansson, V., Taskén, K. *Protein kinase A type I antagonist restores immune responses of T cells from HIV-infected patients. FASEB J.* 12, 855-862 (1998).

It has also been recognised that mutations in the regulatory sub-unit of PKA can lead to hyperactivation in endocrine tissue.

Because of the diversity and importance of PKA as a messenger in cell regulation, abnormal responses of cAMP can lead to a variety of human diseases derived from this, such as irregular cell growth and proliferation (Stratakis, C. A.; Cho-Chung, Y. S.; Protein Kinase A and human diseases. *Trends Endrocri. Metab.* 2002, 13, 50-52). Over-expression of PKA has been observed in a variety of human cancer cells including those from ovarian, breast and colon patients. Inhibition of PKA would therefore be an approach to treatment of cancer (Li, Q.; Zhu, G-D.; *Current Topics in Medicinal Chemistry*, 2002, 2, 939-971).

For a review of the role of PKA in human disease, see for example, *Protein Kinase A and Human Disease*, Edited by Constantine A. Stratakis, Annals of the New York Academy of Sciences, Volume 968, 2002, ISBN 1-57331-412-9.

PRIOR ART

Several classes of compounds have been disclosed as having PKA and PKB inhibitory activity.

For example, a class of isoquinolinyl-sulphonamido-diamines having PKB inhibitory activity is disclosed in WO 01/91754 (Yissum).

WO 93/13072 (Italfarmaco) discloses a class of bis-sulphonamido diamines as protein kinase inhibitors.

WO 99/65909 (Pfizer) discloses a class of pyrrole[2,3-d] pyrimidine compounds having protein tyrosine kinase activity and which are of potential use as immunosuppressant agents.

WO 2004/074287 (Astra Zeneca) discloses piperazinyl-pyridyl amides for use in treating autoimmune diseases such as arthritis. The piperazine group in the compounds can be linked to a purine group.

WO02/18348 (F. Hoffman La Roche) discloses a class of amino-quinazoline derivatives as alpha-1 adrenergic antagonists. A method for preparing the amino-quinazoline compounds involves the use of a gem-disubstituted cyclic amine such as piperidine in which one of the gem substituents is an aminomethyl group.

WO03/088908 (Bristol Myers Squibb) discloses N-heteroaryl-4,4-disubstituted piperidines as potassium channel inhibitors.

WO01/07050 (Schering) discloses substituted piperidines as nociceptin receptor ORL-1 agonists for use in treating cough.

US 2003/0139427 (OSI) discloses pyrrolidine- and piperidine-substituted purines and purine analogues having adenosine receptor binding activity.

WO 2004/043380 (Harvard College et al.) discloses technetium and rhenium labelled imaging agents containing disubstituted piperidine metal ion-chelating ligands.

WO 97/38665 (Merck) discloses gem-disubstituted piperidine derivatives having farnesyl transferase inhibitory activity.

EP 1568699 (Eisai) discloses 1,3-dihydroimidazole fused ring compounds having DPPIV-inhibiting activity. The compounds are described as having a range of potential uses including the treatment of cancer.

US 2003/0073708 and US 2003/045536 (both in the name of Castelhano et al), WO 02/057267 (OSI Pharmaceuticals) and WO 99/62518 (Cadus Pharmaceutical Corporation) each disclose a class of 4-aminodeazapurines in which the 4-amino group can form part of a cyclic amine such as azetidine, pyrrolidine and piperidine. The compounds are described as having adenosine receptor antagonist activity.

U.S. Pat. No. 6,162,804 (Merck) discloses a class of benzimidazole and aza-benzimidazole compounds that have tyrosine kinase inhibitor activity.

SUMMARY OF THE INVENTION

The invention provides compounds that have protein kinase B (PKB) and/or protein kinase A (PKA) inhibiting or modulating activity, and which it is envisaged will be useful in preventing or treating disease states or conditions mediated by PKB and/or PKA.

Accordingly, in one aspect, the invention provides a compound for use as a protein kinase B inhibitor, the compound being a compound of the formula (I):

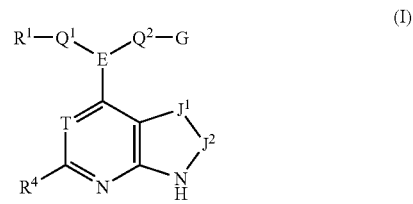

or salts, solvates, tautomers or N-oxides thereof, wherein

T is N or a group $CR^5$;

$J^1$-$J^2$ represents a group selected from $N=C(R^6)$, $(R^7)C=N$, $(R^8)N-C(O)$, $(R^8)_2C-C(O)$, $N=N$ and $(R^7)C=C(R^6)$;

E is a monocyclic carbocyclic or heterocyclic group of 5 or 6 ring members wherein the heterocyclic group contains up to 3 heteroatoms selected from O, N and S;

$Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety; and wherein the carbon atoms of the linker group $Q^1$ may optionally bear one or more substituents selected from fluorine and hydroxy;

$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom α with respect to the G group;

G is selected from hydrogen, $NR^2R^3$, OH and SH with the proviso that when E is aryl or heteroaryl and $Q^2$ is a bond, then G is hydrogen;

$R^1$ is hydrogen or an aryl or heteroaryl group, with the proviso that when $R^1$ is hydrogen and G is $NR^2R^3$, then $Q^2$ is a bond;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, cyano, amino, methylamino, dimethylamino, methoxy and a monocyclic or bicyclic aryl or heteroaryl group;

or $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ when present and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ and $NHCONHR^9$;

$R^5$ and $R^7$ are each independently selected from hydrogen, halogen, $C_{1-5}$ saturated hydrocarbyl, cyano and $CF_3$;

$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^cC$ is selected from hydrogen and $C_{1-4}$ hydrocarbyl; and $X^1$ is O, S or $NR^c$ and $X^2$ is =O, =S or =$NR^c$.

In a further aspect, the invention provides a compound for use as a protein kinase B inhibitor, the compound being a compound of the formula (Ia):

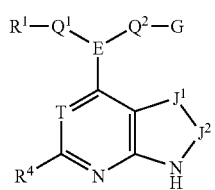

(Ia)

or salts, solvates, tautomers or N-oxides thereof, wherein

T is N or a group $CR^5$;

$J^1$-$J^2$ represents a group selected from N=$C(R^6)$, $(R^7)$C=N, $(R^8)$N—C(O), $(R^8)_2$C—C(O), N=N and $(R^7)$C=$C(R^6)$;

E is a monocyclic carbocyclic or heterocyclic group of 5 or 6 ring members wherein the heterocyclic group contains up to 3 heteroatoms selected from O, N and S;

$Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom α with respect to the G group;

G is selected from hydrogen, $NR^2R^3$, OH and SH with the proviso that when E is aryl or heteroaryl and $Q^2$ is a bond, then G is hydrogen;

$R^1$ is hydrogen or an aryl or heteroaryl group, with the proviso that when $R^1$ is hydrogen and G is $NR^2R^3$, then $Q^2$ is a bond;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, amino, methylamino, dimethylamino, methoxy and a monocyclic or bicyclic aryl or heteroaryl group;

or $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ when present and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ and $NHCONHR^9$;

$R^5$ and $R^7$ are each independently selected from hydrogen, halogen, $C_{1-5}$ saturated hydrocarbyl, cyano and $CF_3$;

$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

In another aspect, the invention provides a compound for use as a protein kinase B inhibitor, the compound being a compound of the formula (Ib):

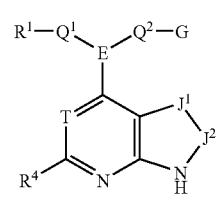

(Ib)

or salts, solvates, tautomers or N-oxides thereof, wherein

T is N or a group $CR^5$;

$J^1$-$J^2$ represents a group selected from N=$C(R^6)$, $(R^7)$C=N, $(R^8)$N—C(O), $(R^8)_2$C—C(O), N=N and $(R^7)$C=$C(R^6)$;

E is a monocyclic carbocyclic or heterocyclic group of 5 or 6 ring members wherein the heterocyclic group contains up to 3 heteroatoms selected from O, N and S;

$Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom α with respect to the G group;

G is selected from hydrogen, $NR^2R^3$, OH and SH with the proviso that when E is aryl or heteroaryl and $Q^2$ is a bond, then G is hydrogen;

$R^1$ is hydrogen or an aryl or heteroaryl group, with the proviso that when $R^1$ is hydrogen and G is $NR^2R^3$, then $Q^2$ is a bond;

$R^2$ and $R^3$ are independently selected from hydrogen; $C_{1-4}$ hydrocarbyl and $C_{1-4}$ acyl wherein the hydrocarbyl and acyl groups are optionally substituted by a monocyclic or bicyclic aryl or heteroaryl group;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ when present and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;

$R^5$ and $R^7$ are each independently selected from hydrogen, halogen, $C_{1-5}$ saturated hydrocarbyl, cyano and $CF_3$;

$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond; O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

In another aspect, the invention provides a novel compound of the formula (Ic):

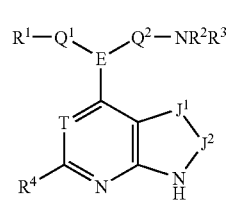

or salts, solvates, tautomers or N-oxides thereof, wherein

T is N or a group $CR^5$;

$J^1$-$J^2$ represents a group selected from N=C($R^6$), ($R^7$)C=N, ($R^8$)N—C(O), ($R^8$)$_2$C—C(O), N=N and ($R^7$)C=C($R^6$);

E is a monocyclic carbocyclic or heterocyclic group of 5 or 6 ring members wherein the heterocyclic group contains up to 3 heteroatoms selected from O, N and S;

$Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety; and wherein the carbon atoms of the linker group $Q^1$ may optionally bear one or more substituents selected from fluorine and hydroxy;

$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom α with respect to the G group; and provided that when E is aryl or heteroaryl, then $Q^2$ is other than a bond;

$R^1$ is an aryl or heteroaryl group;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, cyano, hydroxy, amino, methylamino, dimethylamino, methoxy and a monocyclic or bicyclic aryl or heteroaryl group;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;

$R^5$ and $R^7$ are each independently selected from hydrogen, halogen, $C_{1-5}$ saturated hydrocarbyl, cyano and $CF_3$;

$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

In another aspect, the invention provides a novel compound of the formula (Id):

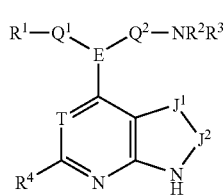

(Id)

or salts, solvates, tautomers or N-oxides thereof, wherein
T is N or a group $CR^5$;
$J^1$-$J^2$ represents a group selected from N=$C(R^6)$, $(R^7)$C=N, $(R^8)N$—C(O), $(R^8)_2C$—C(O), N=N and $(R^7)$C=$C(R^6)$;
E is a monocyclic carbocyclic or heterocyclic group of 5 or 6 ring members wherein the heterocyclic group contains up to 3 heteroatoms selected from O, N and S;
$Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom α with respect to the G group; and provided that when E is aryl or heteroaryl, then $Q^2$ is other than a bond;
$R^1$ is an aryl or heteroaryl group;
$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, amino, methylamino, dimethylamino, methoxy and a monocyclic or bicyclic aryl or heteroaryl group;
or $R^2$ and $R^3$ together with the nitrogen atom to which they are attached form a saturated monocyclic heterocyclic group having 4-7 ring members and optionally containing a second heteroatom ring member selected from O and N;
or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;
or $NR^2R^3$ and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;
$R^5$ and $R^7$ are each independently selected from hydrogen, halogen, $C_{1-5}$ saturated hydrocarbyl, cyano and $CF_3$;
$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;
$R^c$ is selected from hydrogen and $C_{1-4}$ hydrocarbyl; and $X^1$ is O, S or $NR^c$ and $X^2$ is =O, =S or =$NR^c$.

The invention also provides:

A compound per se of the formula (II), (III), (IV), (V), (VII) or any other sub-group or embodiment of the formula (I) as defined herein.

A compound of the formula (I), (Ia), (Ib), (Ic), (Id), (II), (IIa), (III), (IV), (V), (VI), (VII) or any sub-group thereof as defined herein for use in the prophylaxis or treatment of a disease state or condition mediated by protein kinase B.

The use of a compound of formula (I), (Ia), (Ib), (Ic), (Id), (II), (IIa), (III), (IV), (V), (VI), (VII) or any sub-group thereof as defined herein for the manufacture of a medicament for the prophylaxis or treatment of a disease state or condition mediated by protein kinase B.

A method for the prophylaxis or treatment of a disease state or condition mediated by protein kinase B, which method comprises administering to a subject in need thereof a compound of the formula (I), (Ia), (Ib), (Ic), (Id), (II), (IIa), (III), (IV), (V), (VI), (VII) or any sub-group thereof as defined herein.

A method for treating a disease or condition comprising or arising from abnormal cell growth or abnormally arrested cell death in a mammal, the method comprising administering to the mammal a compound of the formula (I), (Ia), (Ib), (Ic), (Id), (II), (IIa), (III), (IV), (V), (VI), (VII) or any sub-group thereof as defined herein in an amount effective to inhibit protein kinase B activity.

A method of inhibiting protein kinase B, which method comprises contacting the kinase with a kinase-inhibiting compound of the formula (I), (Ia), (Ib), (Ic), (Id), (II), (IIa), (III), (IV), (V), (VI), (VII) or any sub-group thereof as defined herein.

A method of modulating a cellular process (for example cell division) by inhibiting the activity of a protein kinase B using a compound of the formula (I), (Ia), (Ib), (Ic), (Id), (II), (IIa), (III), (IV), (V), (VI), (VII) or any sub-group thereof as defined herein.

A compound of the formula (I), (Ia), (Ib), (Ic), (Id), (II), (Ia), (III), (IV), (V), (VI), (VII) or any sub-group or embodiment thereof as defined herein for use in the prophylaxis or treatment of a disease state or condition mediated by protein kinase A.

The use of a compound of formula (I), (Ia), (Ib), (Ic), (Id), (II), (Ia), (III), (IV), (V), (VI), (VII) or any sub-group or embodiment thereof as defined herein for the manufacture of a medicament for the prophylaxis or treatment of a disease state or condition mediated by protein kinase A.

A method for the prophylaxis or treatment of a disease state or condition mediated by protein kinase A, which method comprises administering to a subject in need thereof a compound of the formula (I), (Ia), (Ib), (Ic), (Id), (II), (IIa), (III), (IV), (V), (VI), (VII) or any sub-group or embodiment thereof as defined herein.

A method for treating a disease or condition comprising or arising from abnormal cell growth or abnormally arrested cell death in a mammal, the method comprising administering to the mammal a compound of the formula (I), (Ia), (Ib), (Ic), (Id), (II), (IIa), (III), (IV), (V), (VI), (VII) or any sub-group or embodiment thereof as defined herein in an amount effective to inhibit protein kinase A activity.

A method of inhibiting protein kinase A, which method comprises contacting the kinase with a kinase-inhibiting compound of the formula (I), (Ia), (Ib), (Ic), (Id), (II), (IIa), (III), (IV), (V), (VI), (VII) or any sub-group or embodiment thereof as defined herein.

A method of modulating a cellular process (for example cell division) by inhibiting the activity of a protein kinase A using a compound of the formula (I), (Ia), (Ib), (Ic), (Id), (II), (IIa), (III), (IV), (V), (VI), (VII) or any sub-group or embodiment thereof as defined herein.

The use of a compound of the formula (I), (Ia), (Ib), (Ic), (Id), (II), (IIa), (III), (IV), (V), (VI), (VII) or any sub-group thereof as defined herein for the manufacture of a medicament for the prophylaxis or treatment of a disease state or condition arising from abnormal cell growth or abnormally arrested cell death.

A method for treating a disease or condition comprising or arising from abnormal cell growth in a mammal, which method comprises administering to the mammal a compound of the formula (I), (Ia), (Ib), (Ic), (Id), (II), (IIa), (III), (IV), (V), (VI), (VII) or any sub-group thereof as defined herein in an amount effective in inhibiting abnormal cell growth or abnormally arrested cell death.

A method for alleviating or reducing the incidence of a disease or condition comprising or arising from abnormal cell growth or abnormally arrested cell death in a mammal, which method comprises administering to the mammal a compound of the formula (I), (Ia), (Ib), (Ic), (Id), (II), (IIa), (III), (IV), (V), (VI), (VII) or any sub-group thereof as defined herein in an amount effective in inhibiting abnormal cell growth.

A pharmaceutical composition comprising a novel compound of the formula (I), (Ia), (Ib), (Ic), (Id), (II), (IIa), (III), (IV), (V), (VI), (VII) or any sub-group thereof as defined herein and a pharmaceutically acceptable carrier.

A compound of the formula (I), (Ia), (Ib), (Ic), (Id), (II), (IIa), (III), (IV), (V), (VI), (VII) or any sub-group thereof as defined herein for use in medicine.

The use of a compound of the formula (I), (Ia), (Ib), (Ic), (Id), (II), (IIa), (III), (IV), (V), (VI), (VII) or any sub-group thereof as defined herein for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a compound (e.g. a therapeutically effective amount) of the formula (I), (Ia), (Ib), (Ic), (Id), (II), (IIa), (III), (IV), (V), (VI), (VII) or any sub-group thereof as defined herein.

A method for alleviating or reducing the incidence of a disease state or condition disclosed herein, which method comprises administering to a patient (e.g. a patient in need thereof) a compound (e.g. a therapeutically effective amount) of the formula (I), (Ia), (Ib), (Ic), (Id), (II), (Ia), (III), (IV), (V), (VI), (VII) or any sub-group thereof as defined herein.

A method for the diagnosis and treatment of a disease state or condition mediated by protein kinase B, which method comprises (i) screening a patient to determine whether a disease or condition from which the patient is or may be suffering is one which would be susceptible to treatment with a compound having activity against protein kinase B; and (ii) where it is indicated that the disease or condition from which the patient is thus susceptible, thereafter administering to the patient a compound of the formula (I), (Ia), (Ib), (Ic), (Id), (II), (IIa), (III), (IV), (V), (VI), (VII) or any sub-group thereof as defined herein.

The use of a compound of the formula (I), (Ia), (Ib), (Ic), (Id), (II), (IIa), (III), (IV), (V), (VI), (VII) or any sub-group thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase B.

A method for the diagnosis and treatment of a disease state or condition mediated by protein kinase A, which method comprises (i) screening a patient to determine whether a disease or condition from which the patient is or may be suffering is one which would be susceptible to treatment with a compound having activity against protein kinase A; and (ii) where it is indicated that the disease or condition from which the patient is thus susceptible, thereafter administering to the patient a compound of the formula (I), (Ia), (Ib), (Ic), (Id), (II), (IIa), (III), (IV), (V), (VI), (VII) or any sub-group or embodiment thereof as defined herein.

The use of a compound of the formula (I), (Ia), (Ib), (Ic), (Id), (II), (IIa), (III), (IV), (V), (VI), (VII) or any sub-group or embodiment thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase A.

Any one or more of the following optional provisos may apply in any combination to any one of the formulae (I), (Ia), (Ib), (Ic), (Id), (II), (IIa), (III), (IV), (V), (VI), (VII) and any sub-groups and embodiments as defined herein.

(i) When $J^1$-$J^2$ is $(R^7)C=C(R^6)$ and $R^1$ is an aryl or heteroaryl group, the aryl or heteroaryl group bears one or more substituents (i.e. a moiety other than hydrogen) as defined herein.

(ii) When $Q^1$ is a bond, and E is a piperazine group, $R^1$ is other than a substituted pyridyl group linked to a nitrogen atom of the piperazine group wherein the substituted pyridyl group is substituted by an amide moiety.

(iii) When $Q^1$ contains a nitrogen atom and the moiety $Q^2$-G contains a heterocyclic group, $R^1$ is other than a substituted aminoquinoxaline group.

GENERAL PREFERENCES AND DEFINITIONS

The following general preferences and definitions shall apply to each of the moieties T, E, G, $Q^1$, $Q^2J^1$, $J^2$, T and $R^1$ to $R^9$ and any sub-definition, sub-group or embodiment thereof, unless the context indicates otherwise.

Any references to Formula (I) herein shall be taken also to refer to formulae (Ia), (Ib), (Ic), (Id), (Ie), (II), (IIa), (III), (IV), (V), (VI), (VII) and any other sub-group of compounds within formula (I)), or embodiment thereof, unless the context requires otherwise.

In this specification, references to "the bicyclic group", when used in regard to the point of attachment of the group E shall, unless the context indicates otherwise, be taken to refer to the group:

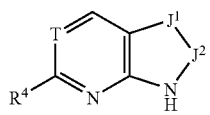

References to "carbocyclic" and "heterocyclic" groups as used herein shall, unless the context indicates otherwise, include both aromatic and non-aromatic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term non-aromatic group embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings. Each ring may contain up to about four heteroatoms typically selected from nitrogen, sulphur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a a 5- or 6-membered ring containing 1, 2 or 3 ring heteroatoms;
e) a pyrazole ring fused to a a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered ring containing 1, 2 or 3 ring heteroatoms; and
o) a cyclopentyl ring fused to a 5- or 6-membered ring containing 1, 2 or 3 ring heteroatoms.

Particular examples of bicyclic heteroaryl groups containing a six membered ring fused to a five membered ring include but are not limited to benzfuran, benzthiophene, benzimidazole, benzoxazole, benzisoxazole, benzthiazole, benzisothiazole, isobenzofuran, indole, isoindole, indolizine, indoline, isoindoline, purine (e.g., adenine, guanine), indazole, benzodioxole and pyrazolopyridine groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1, 2, 3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocylic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic urea moieties (e.g. as in imidazolidin-2-one), cyclic thiourea moieties, cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide).

Examples of monocyclic non-aromatic heterocyclic groups include 5-, 6- and 7-membered monocyclic heterocyclic groups. Particular examples include morpholine, thiomorpholine and its S-oxide and S,S-dioxide (particularly thiomorpholine), piperidine (e.g. 1-piperidinyl, 2-piperidinyl 3-piperidinyl and 4-piperidinyl), N-alkyl piperidines such as N-methyl piperidine, piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine, N-ethyl piperazine and N-isopropylpiperazine. In general, preferred non-aromatic heterocyclic groups include piperidine, pyrrolidine, azetidine, morpholine, piperazine and N-alkyl piperazines.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are monocyclic rings and most preferably saturated monocyclic rings.

Typical examples are three, four, five and six membered saturated carbocyclic rings, e.g. optionally substituted cyclopentyl and cyclohexyl rings.

One sub-set of non-aromatic carbocyclic groups includes unsubstituted or substituted (by one or more groups $R^{10}$) monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example *Advanced Organic Chemistry*, by Jerry March, 4th Edition, Wiley Interscience, pages 131-133, 1992. Examples of bridged ring systems include bicyclo[2.2.1]heptane, aza-bicyclo[2.2.1]heptane, bicyclo[2.2.2]octane, aza-bicyclo[2.2.2]octane, bicyclo[3.2.1]octane and aza-bicyclo[3.2.1]octane.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, SO$_2$, NR$^c$, SO$_2$NR$^c$ or NR$^c$SO$_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, SO$_2$, NR$^c$, $X^1C(X^2)$, $C(X^2)X^1$ or $X^1C(X^2)X^1$;

$R^c$ is selected from hydrogen and $C_{1-4}$ hydrocarbyl; and
$X^1$ is O, S or NR$^c$ and $X^2$ is =O, =S or =NR$^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 10, or 9, or 8, or 7, or 6, or 5 non-hydrogen atoms.

One sub-group of substituents $R^{10}$ is represented by $R^{10a}$ which consists of substituents selected from halogen, hydroxy, trifluoromethyl, cyano, nitro, carboxy, amino, mono- or di-$C_{1-4}$ hydrocarbylamino, carbocyclic and heterocyclic groups having from 3 to 7 ring members; a group $R^a$-$R^b$ wherein $R^a$ is a bond, O, CO, OC(O), NR$^c$C(O), OC(NR$^c$), C(O)O, C(O)NR$^c$, OC(O)O, NR$^c$C(O)O, OC(O)NR$^c$, NR$^c$C(O)NR$^c$, S, SO, SO$_2$, NR$^c$, SO$_2$NR$^c$ or NR$^c$SO$_2$; and $R^b$ is selected from hydrogen, carbocyclic and heterocyclic groups having from 3 to 7 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 7 ring members and wherein one or more carbon atoms of the $C_{1-8}$ hydrocarbyl group may optionally be replaced by O, S, SO, SO$_2$, NR$^c$, OC(O), NR$^c$C(O), OC(NR$^c$), C(O)O, C(O)NR$^c$, OC(O)O, NR$^c$C(O)O, OC(O)NR$^c$ or NR$^c$C(O)NR$^c$;

R$^c$C is selected from hydrogen and $C_{1-4}$ hydrocarbyl.

Another sub-group of substituents $R^{10}$ is represented by $R^{10b}$ which consists of substituents selected from halogen, hydroxy, trifluoromethyl, cyano, amino, mono- or di-$C_{1-4}$ alkylamino, cyclopropylamino, carbocyclic and heterocyclic groups having from 3 to 7 ring members; a group $R^a$-$R^b$ wherein $R^a$ is a bond, O, CO, OC(O), NR$^c$C(O), OC(NR$^c$), C(O)O, C(O)NR$^c$, S, SO, SO$_2$, NR$^c$, SO$_2$NR$^c$ or NR$^c$SO$_2$; and $R^b$ is selected from hydrogen, carbocyclic and heterocyclic groups having from 3 to 7 ring members, and a $C_{1-8}$ hydrocarbyl group optionally substituted by one or more substituents selected from hydroxy, oxo, halogen, cyano, amino, mono- or di-$C_{1-4}$ alkylamino, carbocyclic and heterocyclic groups having from 3 to 7 ring members and wherein one or more carbon atoms of the $C_{1-8}$ hydrocarbyl group may optionally be replaced by O, S, SO, $SO_2$ or $NR^c$; provided that $R^a$ is not a bond when $R^b$ is hydrogen; and
$R^c$ is selected from hydrogen and $C_{1-4}$alkyl.

A further sub-group of substituents $R^{10}$ is represented by $R^{10c}$ which consists of substituents selected from:
halogen,
hydroxy,
trifluoromethyl,
cyano,
amino, mono- or di-$C_{1-4}$ alkylamino,
cyclopropylamino,
monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
a group $R^a\text{-}R^b$;
$R^a$ is a bond, O, CO, OC(O), $NR^cC(O)$, $OC(NR^c)$, C(O)O, $C(O)NR^c$, S, SO, $SO_2$, $NR^c$, $SO_2NR^c$ or $NR^cSO_2$;
$R^b$ is selected from hydrogen, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
and $R^b$ is further selected from a $C_{1-8}$ hydrocarbyl group optionally substituted by one or more substituents selected from hydroxy, oxo, halogen, cyano, amino, mono- or di-$C_{1-4}$ alkylamino, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy, and wherein one or two carbon atoms of the $C_{1-8}$ hydrocarbyl group may optionally be replaced by O, S or $NR^c$; provided that $R^a$ is not a bond when $R^b$ is hydrogen; and $R^c$ is selected from hydrogen and $C_{1-4}$ alkyl.

Where the carbocyclic and heterocyclic groups have a pair of substituents on adjacent ring atoms, the two substituents may be linked so as to form a cyclic group. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group. Examples of such linked substituent groups include:

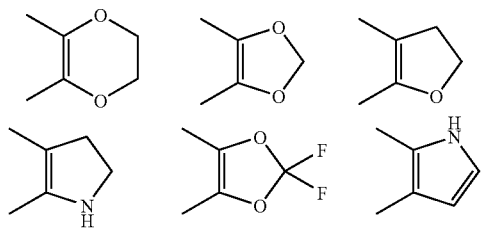

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms. Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, can be substituted by one or more substituents as defined herein. The examples and preferences expressed below apply to each of the hydrocarbyl substituent groups or hydrocarbyl-containing substituent groups referred to in the various definitions of substituents for compounds of the formula (I) and sub-groups thereof as defined herein unless the context indicates otherwise.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "saturated hydrocarbyl", whether used alone or together with a suffix such as "oxy" (e.g. as in "hydrocarbyloxy"), refers to a non-aromatic hydrocarbon group containing no multiple bonds such as C=C and C≡C.

Particular hydrocarbyl groups are saturated hydrocarbyl groups such as alkyl and cycloalkyl groups as defined herein.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 8 carbon atoms, particular examples being $C_{1-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

Examples of carbocyclic aryl groups include substituted and unsubstituted phenyl, naphthyl, indane and indene groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members.

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom.

The definition "$R^a$-$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, $C(S)NR^c$, $C(NR^c)O$, $C(NR^c)S$, $C(NR^c)NR^c$, OC(O)O, SC(O)O, $NR^cC(O)O$, OC(S)O, SC(S)O, $NR^cC(S)O$, $OC(NR^c)O$, $SC(NR^c)O$, $NR^cC(NR^c)O$, OC(O)S, SC(O)S, SC(S)S, $NR^cC(S)S$, $OC(NR^c)S$, SC(N-$R^c$)S, $NR^cC(NR^c)S$, $OC(O)NR^c$, $SC(O)NR^c$, $NR^cC(O)NR^c$, $OC(S)NR^c$, $SC(S)NR^c$, $NR^cC(S)NR^c$, $OC(NR^c)NR^c$, SC(N- $R^c)NR^c$, $NR^cC(NR^cNR^c$, S, SO, $SO_2$. $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted by, for example, a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl, difluoromethyl, 2,2,2-trifluoroethyl and perfluoroalkyl groups such as trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$ alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl, phenethyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $SO_2NR^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for E, T, G, $Q^1$, $Q^2$, $J^1$, $J^2$ and $R^1$ to $R^{10}$

T

In formula (I), T can be nitrogen or a group $CR^5$ and $J^1$-$J^2$ can represent a group selected from N=C($R^6$), ($R^7$)C=N, ($R^8$)N—C(O), ($R^8$)$_2$C—C(O) and ($R^7$)C=C($R^6$). Thus the bicyclic group can take the form of, for example:

- a purine (T is N, $J^1$-$J^2$ is N=C($R^6$));
- a 3H-imidazo[4,5-b]pyridine (T is $CR^5$, $J^1$-$J^2$ is N=C ($R^6$));
- a 7H-pyrrolo[2,3-d]pyrimidine (T is N, $J^1$-$J^2$ is ($R^7$)C=C ($R^6$));
- a 1H-pyrrolo[2,3-b]pyridine (T is $CR^5$, $J^1$-$J^2$ is ($R^7$)C=C ($R^6$));
- a 5,7-dihydro-pyrrolo[2,3-d]pyrimidin-6-one (T is N, $J^1$-$J^2$ is ($R^8$)$_2$C—C(O));
- a 3H-[1,2,3]triazolo[4,5-d]pyrimidine (T is N, $J^1$-$J^2$ is N=N);
- a 3H-[1,2,3]triazolo[4,5-b]pyridine (T is $CR^5$, $J^1$-$J^2$ is N=N);
- a 7,9-dihydro-purin-8-one (T is N, $J^1$-$J^2$ is ($R^8$)N—C(O));
- a 1H-pyrazolo[3,4-d]pyrimidine (T is N, $J^1$-$J^2$ is ($R^7$)C=N); or
- a pyrazolo[3,4-b]pyridine (T is $CR^5$, $J^1$-$J^2$ is ($R^7$)C=N).

$R^4$ $R^4$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically, $R^4$ is selected from hydrogen, chlorine, fluorine and methyl, and preferably $R^4$ is hydrogen.

$R^5$ $R^5$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically, $R^5$ is selected from hydrogen, halogen, $C_{1-5}$ saturated hydrocarbyl, cyano and $CF_3$. Preferably, $R^5$ is selected from hydrogen, chlorine, fluorine and methyl, and more preferably $R^5$ is hydrogen.

$R^6$ $R^6$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically $R^6$ is selected from hydrogen, chlorine, fluorine and methyl, and preferably $R^6$ is hydrogen.

$R^7$ $R^7$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically $R^7$ is selected from hydrogen, halogen, $C_{1-5}$ saturated hydrocarbyl, cyano and $CF_3$. Preferably, $R^7$ is selected from hydrogen, chlorine, fluorine and methyl, and more preferably $R^7$ is hydrogen.

$R^8$ $R^8$ is selected from hydrogen, halogen, $C_{1-5}$ saturated hydrocarbyl (e.g. alkyl), cyano, $CONH_2$, $CONHR^9$, $CF_3$, $NH_2$, $NHCOR^9$ and $NHCONHR^9$. In one embodiment, when attached to a nitrogen atom, $R^8$ is selected from hydrogen and $C_{1-5}$ saturated hydrocarbyl (e.g. alkyl) and more typically is selected from hydrogen, methyl and ethyl; and preferably is hydrogen. In another embodiment, when attached to a carbon atom, $R^8$ is selected from hydrogen, chlorine, fluorine, methyl, and ethyl; and preferably is hydrogen.

$R^9$ $R^9$ is phenyl or benzyl each optionally substituted as defined herein. Particular groups $R^9$ are phenyl and benzyl groups that are unsubstituted or are substituted with a solubilising group such as an alkyl or alkoxy group bearing an amino, substituted amino, carboxylic acid or sulphonic acid group. Particular examples of solubilising groups include amino-$C_{1-4}$-alkyl, mono-$C_{1-2}$-alkylamino-$C_{1-4}$-alkyl, di-$C_{1-2}$-alkylamino-$C_{1-4}$-alkyl, amino-$C_{1-4}$-alkoxy, mono-$C_{1-2}$-alkylamino-$C_{1-4}$-alkoxy, di-$C_{1-2}$-alkylamino-$C_{1-4}$-alkoxy, piperidinyl-$C_{1-4}$-alkyl, piperazinyl-$C_{1-4}$-alkyl, morpholinyl-$C_{1-4}$-alkyl, piperidinyl-$C_{1-4}$-alkoxy, piperazinyl-$C_{1-4}$-alkoxy and morpholinyl-$C_{1-4}$-alkoxy.

$Q^1$ and $Q^2$ $Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety; and wherein the carbon atoms of the linker group $Q^1$ may optionally bear one or more substituents selected from fluorine and hydroxy.

$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom α with respect to the G group.

In one embodiment, $Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom α with respect to the $G^2$ group.

In one group of compounds of the invention, at least one of $Q^1$ and $Q^2$ represents a bond. Within this group of compounds, one sub-group consists of compounds in which both of $Q^1$ and $Q^2$ represent a bond. In another sub-group, one of $Q^1$ and $Q^2$ represents a bond, and the other represents a saturated hydrocarbon linker group containing from 1 to 3 carbon atoms, wherein one of the carbon atoms in the linker group may optionally be replaced by an oxygen or nitrogen atom.

When $Q^1$ and/or $Q^2$ are saturated hydrocarbon groups, the hydrocarbon groups are typically alkylene groups such as $(CH_2)_n$ where n is 1, 2 or 3, one particular example being $CH_2$. One of the carbon atoms in the alkylene group $Q^1$ may optionally be replaced by, for example, an oxygen atom, and an example of such a group is $CH_2$—O—$CH_2$.

The carbon atoms of the linker groups $Q^1$ and $Q^2$ may optionally bear one or more substituents selected from oxo, fluorine and hydroxy, provided that the hydroxy group is not located at a carbon atom α with respect to the $NR^2R^3$ group when present, and provided also that the oxo group is located at a carbon atom α with respect to the $NR^2R^3$ group when present. Typically, the hydroxy group, if present, is located at a position β with respect to G when G is other than hydrogen. In general, no more than one hydroxy group will be present. Where fluorine atoms are present, they may be present in a difluoromethylene or trifluoromethyl group, for example.

In one sub-group of compounds, $Q^1$ is a saturated hydrocarbon linker group containing from 1 to 3 carbon atoms, wherein an adjacent pair of carbon atoms is replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety. In one preferred embodiment, $R^q$ is hydrogen. In another embodiment, $R^q$ is $C_{1-4}$ alkyl or cyclopropyl, preferably methyl. In a further embodiment, $R^q$ is a $C_{1-4}$ alkylene chain that links to $R^1$ or to another carbon atom of $Q^1$ to form a cyclic moiety.

Examples of linker groups $Q^1$ containing $CONR^q$ or $NR^qCO$ are the groups $CH_2NHCO$ and $CH_2N(Me)CO$ where the carbonyl group is attached to E.

Examples of linker groups $Q^1$ containing $CONR^q$ or $NR^qCO$, where $R^q$ is a $C_{1-4}$ alkylene chain that links to another carbon atom of $Q^1$ to form a cyclic moiety, are groups represented by the formula:

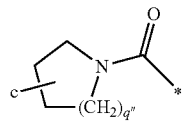

where * represents the point of attachment to the moiety E, q" is 0, 1 or 2, and the point of attachment to $R^1$ is indicated by the letter "c".

Examples of linker groups $Q^1$ containing $CONR^q$ or $NR^qCO$, where $R^q$ is a $C_{1-4}$ alkylene chain that links to $R^1$ to form a cyclic moiety, are groups represented by the formula:

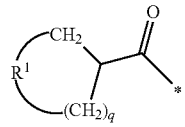

where q is as defined herein and $R^1$ is an aryl or heteroaryl group. Particular examples of moieties $R^1$-$Q^1$ of this type include 1,2,3,4-tetrahydroisoquinolin-2-ylcarbonyl.

It will be appreciated that that when an oxo group is present at the carbon atom adjacent an $NR^2R^3$ group, the compound of the formula (I) will be an amide.

In one embodiment of the invention, no fluorine atoms are present in the linker groups $Q^1$ and/or $Q^2$.

In another embodiment of the invention, no hydroxy groups are present in the linker groups $Q^1$ and/or $Q^2$.

In a further embodiment, no oxo group is present in the linker groups $Q^1$ and/or $Q^2$.

In one group of compounds of the formula (I) neither hydroxy groups nor fluorine atoms are present in the linker groups $Q^1$ and/or $Q^2$, e.g. the linker groups $Q^1$ and/or $Q^2$ are unsubstituted.

In another group of compounds of the invention, the linker group $Q^2$ can have a branched configuration at the carbon atom attached to the $NR^2R^3$ group, when present. For example, the carbon atom attached to the $NR^2R^3$ group can be attached to a pair of gem-dimethyl groups.

$Q^1$ and $Q^2$ may be attached to the same atom of group E, or to different atoms. In one embodiment, $Q^1$ and $Q^2$ are attached to the same atom (i.e. a carbon atom) of group E.

G

The moiety G is selected from hydrogen, $NR^2R^3$, OH and SH with the proviso that when E is aryl or heteroaryl and $Q^2$ is a bond, then G is hydrogen. Thus, in the compounds of formula (I), an amino group $NR^2R^3$ or an SH or OH group are not directly linked to E when E is an aryl or heteroaryl group.

In one embodiment, G is hydrogen.

Preferably at least one of $R^1$ and G is other than hydrogen.

In another embodiment, G is selected from $NR^2R^3$, OH and SH. Within this embodiment, one particular sub-group of compounds is the group in which G is $NR^2R^3$.

Within the sub-group of compounds in which G is $NR^2R^3$, $R^2$ and $R^3$ can be independently selected from hydrogen; $C_{1-4}$ hydrocarbyl and $C_{1-4}$ acyl wherein the hydrocarbyl and acyl groups are optionally substituted by one or more substituents selected from fluorine, hydroxy, cyano, amino, methylamino, dimethylamino, methoxy and a monocyclic or bicyclic aryl or heteroaryl group;

In one group of compounds, $R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, amino, methylamino, dimethylamino, methoxy and a monocyclic or bicyclic aryl or heteroaryl group.

Within this group of compounds are the compounds wherein $R^2$ and $R^3$ are independently selected from hydrogen; $C_{1-4}$ hydrocarbyl and $C_{1-4}$ acyl wherein the hydrocarbyl and acyl groups are each optionally substituted by a monocyclic or bicyclic aryl or heteroaryl group.

Also within this group of compounds is the sub-group of compounds of the invention wherein $R^2$ and $R^3$ are independently selected from hydrogen, $C_{1-4}$ hydrocarbyl and $C_{1-4}$ acyl.

In each of the foregoing groups and sub-groups of compounds, the hydrocarbyl group forming part of $NR^2R^3$ typically is an alkyl group, more usually a $C_1$, $C_2$ or $C_3$ alkyl group, for example a methyl group.

In a particular sub-group of compounds, $R^2$ and $R^3$ are independently selected from hydrogen and methyl and hence $NR^2R^3$ can be an amino, methylamino or dimethylamino group.

In one embodiment, $NR^2R^3$ is an amino group. In another particular embodiment, $NR^2R^3$ is a methylamino group.

In another group of compounds, $R^2$ and $R^3$ together with the nitrogen atom to which they are attached form a saturated monocyclic heterocyclic group having 4-7 ring members and optionally containing a second heteroatom ring member selected from O and N.

In another group of compounds, $NR^2R^3$ and a carbon atom of linker group $Q^2$ to which it is attached from a cyano group.

In a further group of compounds, $NR^2R^3$ is as hereinbefore defined except that $NR^2R^3$ and a carbon atom of linker group $Q^2$ to which it is attached may not form a cyano group.

The saturated monocyclic ring can be an azacycloalkyl group such as an azetidine, pyrrolidine, piperidine or azepane ring, and such rings are typically unsubstituted.

Alternatively, the saturated monocyclic ring can contain an additional heteroatom selected from O and N, and examples of such groups include morpholine and piperazine. Where an additional N atom is present in the ring, this can form part of an NH group or an N—$C_{1-4}$alkyl group such as an N-methyl, N-ethyl, N-propyl or N-isopropyl group.

In a further group of compounds, one of $R^2$ and $R^3$ together with the nitrogen atom to which they are attached and one or more atoms from the linker group $Q^2$ form a saturated monocyclic heterocyclic group having 4-7 ring members and optionally containing a second heteroatom ring member selected from O and N.

$R^1$

The group $R^1$ is hydrogen or a heteroaryl group, wherein the aryl or heteroaryl group may be selected from the list of such groups set out in the section headed General Preferences and Definitions.

In one sub-group of compounds, $R^1$ is hydrogen.

In another sub-group of compounds, $R^1$ is an aryl or heteroaryl group.

When $R^1$ is aryl or heteroaryl, it can be monocyclic or bicyclic and, in one particular embodiment, is monocyclic. Particular examples of monocyclic aryl and heteroaryl groups are six membered aryl and heteroaryl groups containing up to 2 nitrogen ring members, and five membered heteroaryl groups containing up to 3 heteroatom ring members selected from O, S and N.

Examples of such groups include phenyl, naphthyl, thienyl, furan, pyrimidine and pyridine, with phenyl being presently preferred.

The aryl or heteroaryl group $R^1$ can be unsubstituted or substituted by up to 5 substituents, and examples of substituents are those listed in any one of groups $R^{10}R^{10a}$, $R^{10b}$ and $R^{10c}$ above.

In one embodiment, the aryl or heteroaryl group $R^1$ is unsubstituted.

In another embodiment, the aryl or heteroaryl group $R^1$ is substituted by one or more substituents selected from those listed in any one of groups $R^{10}R^{10a}$, $R^{10b}$ and $R^{10c}$ above.

One particular group of substituents for the aryl or heteroaryl group $R^1$ consists of hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by one or more $C_{1-2}$ alkoxy, halogen, hydroxy or optionally substituted phenyl or pyridyl groups; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; optionally substituted phenyl; optionally substituted pyridyl; and optionally substituted phenoxy; wherein the optional substituent for the phenyl, pyridyl and phenoxy groups are 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

Another particular group of substituents for the aryl (e.g. phenyl) or heteroaryl group $R^1$ consists of hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; phenyl; pyridyl; and phenoxy wherein the phenyl, pyridyl and phenoxy groups are each optionally substituted with 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

Although up to 5 substituents may be present, more typically there are 0, 1, 2, 3 or 4 substituents, preferably 0, 1, 2 or 3, and more preferably 0, 1 or 2.

In one embodiment, $R^1$ is unsubstituted (e.g. is an unsubstituted phenyl group) or substituted (e.g. is a substituted phenyl group) by up to 5 substituents selected from hydroxy; $C_{1-4}$ acyloxy; fluorine; chlorine; bromine; trifluoromethyl; trifluoromethoxy; difluoromethoxy; benzyloxy; cyano; $C_{1-4}$ hydrocarbyloxy and $C_{1-4}$ hydrocarbyl each optionally substituted by $C_{1-2}$ alkoxy or hydroxy.

In another embodiment, the group $R^1$ is unsubstituted (e.g. is an unsubstituted phenyl group) or substituted (e.g. is a substituted phenyl group) substituted by up to 5 substituents selected from hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy.

In another embodiment, the group $R^1$ can have one or two substituents selected from fluorine, chlorine, trifluoromethyl, trifluoromethoxy, difluoromethoxy, benzyloxy, methyl and methoxy.

In a further embodiment, the group $R^1$ can have one or two substituents selected from fluorine, chlorine, trifluoromethyl, trifluoromethoxy, difluoromethoxy, benzyloxy, tert-butyl, methyl and methoxy.

For example, $R^1$ can have one or two substituents selected from fluorine, chlorine, trifluoromethyl, methyl and methoxy.

When $R^1$ is a phenyl group, particular examples of substituent combinations include mono-chlorophenyl and dichlorophenyl. Further examples include benzyloxyphenyl, trifluoromethoxyphenyl, tert-butylphenyl, methoxyphenyl, fluoro-chlorophenyl, difluorophenyl, and trifluoromethylphenyl.

In one sub-group of compounds, the group $R^1$ is a phenyl group having a substituent at the para position selected from fluorine, chlorine, trifluoromethyl, trifluoromethoxy, difluoromethoxy, benzyloxy, methyl and methoxy.

In another sub-group of compounds, the group $R^1$ is a phenyl group having a tert-butyl substituent at the para position.

In another sub-group of compounds, the group $R^1$ is a phenyl group having a substituent at the ortho position selected from fluorine, chlorine, trifluoromethyl, trifluoromethoxy, difluoromethoxy, methyl and methoxy, and optionally a second substituent at the meta or para position selected from the group $R^1$ is a phenyl group having a substituent at the para position selected from fluorine, chlorine, trifluoromethyl, trifluoromethoxy, difluoromethoxy, methyl and methoxy.

When $R^1$ is a six membered aryl or heteroaryl group, a substituent may advantageously be present at the para position on the six-membered ring. Where a substituent is present at the para position, it is preferably larger in size than a fluorine atom.

Particular examples of the group R¹ are shown in Table 1 below, the point of attachment to Q¹ (or E when Q¹ is a bond) being indicated by means of an asterisk.
| | |
|---|---|
| 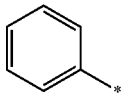 | A1 |
| 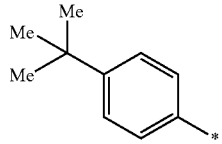 | A2 |
| 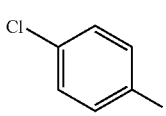 | A3 |
| 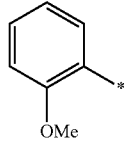 | A4 |
| 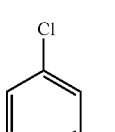 | A5 |
| 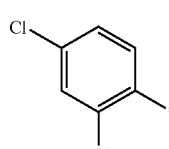 | A6 |
| 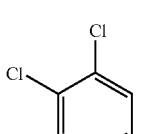 | A7 |
| 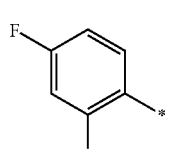 | A8 |
| 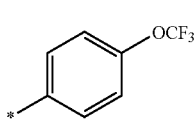 | A9 |
| 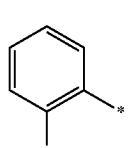 | A10 |
-continued
| | |
|---|---|
| 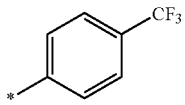 | A11 |
| 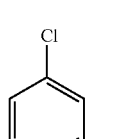 | A12 |
| 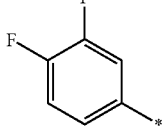 | A13 |
| 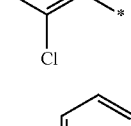 | A14 |
| 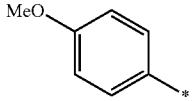 | A15 |
| 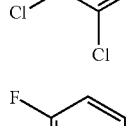 | A16 |
| 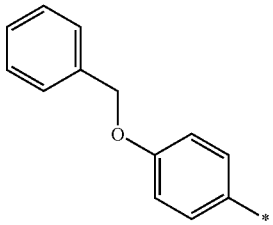 [SMILES: *c1ccc(OCc2ccccc2)cc1] | A17 |
| 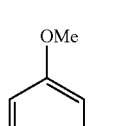 | A18 |
| 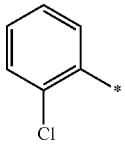 | A19 |
| 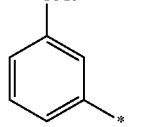 | A20 |

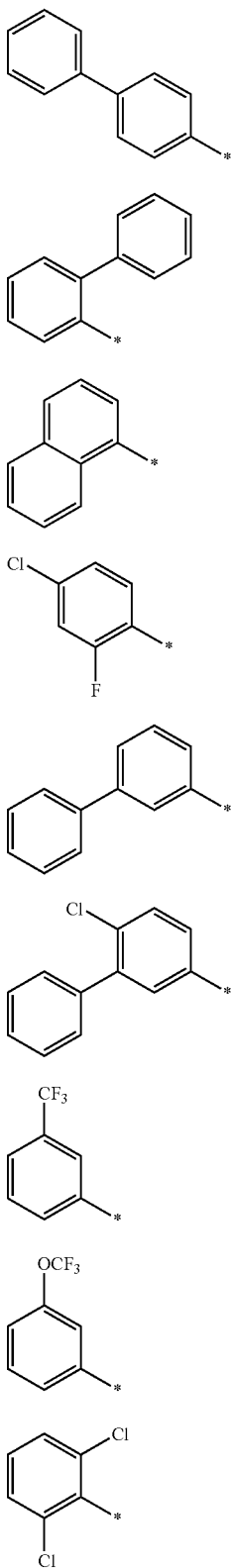

E

In formula (I), E is a monocyclic carbocyclic or heterocyclic group of 5 or 6 ring members wherein the heterocyclic group contains up to 3 heteroatoms selected from O, N and S.

The carbocyclic or heterocyclic group E can be aromatic or non-aromatic.

In one embodiment, the carbocyclic or heterocyclic group E is non-aromatic.

In another embodiment, the carbocyclic or heterocyclic group E is aromatic.

When E is an aromatic group, i.e. an aryl or heteroaryl group, the group can be selected from the examples of such groups set out in the General Preferences and Definitions section above.

Particular aromatic cyclic groups E are aryl and heteroaryl groups containing a six membered aromatic or heteroaromatic ring such as a phenyl, pyridine, pyrazine, pyridazine or pyrimidine ring, more particularly a phenyl, pyridine, pyrazine or pyrimidine ring, and more preferably a pyridine or phenyl ring.

Examples of non-aromatic monocyclic are as set out in the General Preferences and Definitions section above.

Particular examples of groups include cycloalkanes such as cyclohexane and cyclopentane, and nitrogen-containing rings such as piperidine, pyrrolidine, piperidine, piperazine and piperazone.

One particular non-aromatic monocyclic group is a piperidine group and more particularly a piperidine group wherein the nitrogen atom of the piperidine ring is attached to the bicyclic group.

The moieties $Q^1$ and $Q^2$ can be attached to the same carbon atom in the group E or they can be attached to separate atoms. It will be appreciated that when the group E is aromatic, $Q^1$ and $Q^2$ cannot be attached to the same carbon atom in the group E but may be, for example, attached to adjacent carbon atoms.

In one embodiment, E is non-aromatic and $Q^1$ and $Q^2$ are attached to the same carbon atom in the group E.

In another embodiment, $Q^1$ and $Q^2$ are attached to different atoms in the group E.

It is preferred that the group $Q^2$ and the bicyclic group are attached to the group E in a meta or para relative orientation; i.e. $Q^2$ and the bicyclic group are not attached to adjacent ring members of the group E. Examples of groups such groups E include 1,4-phenylene, 1,3-phenylene, 2,5-pyridylene and 2,4-pyridylene, 1,4-piperidinyl, 1,4-piperindonyl, 1,4-piperazinyl, and 1,4-piperazonyl.

The groups E can be unsubstituted or can have up to 4 substituents $R^{11}$ which may be selected from the group $R^{10}$ as hereinbefore defined. More typically however, the substituents $R^{11}$ are selected from hydroxy; oxo (when E is non-aromatic); halogen (e.g. chlorine and bromine); trifluoromethyl; cyano; $C_{1-4}$ hydrocarbyloxy optionally substituted by $C_{1-2}$ alkoxy or hydroxy; and $C_{1-4}$ hydrocarbyl optionally substituted by $C_{1-2}$ alkoxy or hydroxy.

Typically, there are 0-3 substituents, more usually 0-2 substituents, for example 0 or 1 substituent. In one embodiment, the group E is unsubstituted. In one particular group of compounds of the invention, E is a group:

One set of preferred groups $R^1$ includes groups A2, A4 and A5 in Table 1.

Another set of preferred groups includes groups A2, A4, A5, A10, A11, A13, A14, A15, A16, A17, A18, A19 and A19.

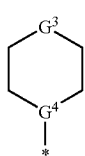

where G³ is selected from C, CH, CH₂, N and NH; and G⁴ is selected from N and CH.

Particular examples of the group E, together with their points of attachment to the groups Q¹ and Q² (ᵃ) and the bicyclic group (*) are shown in Table 2 below.

TABLE 2

B1
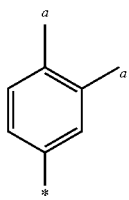

B2
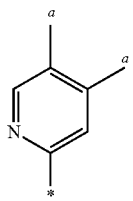

B3
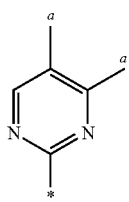

B4
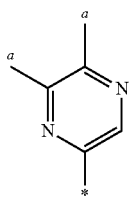

B9
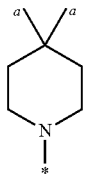 [SMILES: *N1CCC(C)(C)CC1]

B10
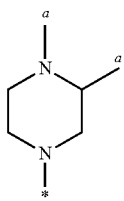 [SMILES: *N1CCN(C)C(C)C1]

TABLE 2-continued

B11
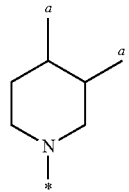

B12
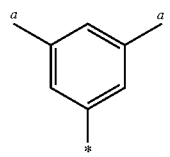

One preferred group E is group B9.

Particular and Preferred Sub-Groups of the Formula (I)

One sub-group of compounds of the formula (I) has the general formula (II):

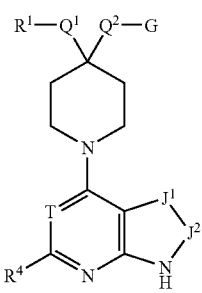

(II)

wherein R¹, R⁴, Q¹, Q², T, J¹, J² and G are as defined herein in respect of formula (I) and sub-groups, examples and preferences thereof. Within Formula (II), particular compounds are those in which Q¹ is a bond or a $C_{1-2}$ alkylene group and Q² is a bond or a methylene group. Preferably R¹ is an aryl or heteroaryl group.

Within Formula (II), one sub-group of compounds has the general formula (IIa):

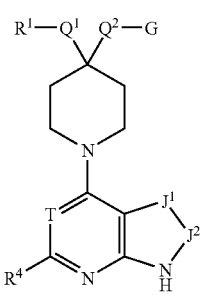

(IIa)

or a salt, solvate tautomer or N-oxide thereof;
wherein R¹ is an aryl or heteroaryl group;
G is selected from NR²R³, OH and SH;
and R⁴, Q, Q², T, J¹ and J² are as defined herein.

In formulae (II) and (IIa), preferably G is NR²R³ and more preferably G is NH₂ or NHMe.

In formulae (II) and (IIa) and embodiments thereof, the group R¹ is preferably an optionally substituted aryl or heteroaryl group, and typically a monocyclic aryl or heteroaryl group of 5 or 6 ring members. Particular aryl and heteroaryl groups are phenyl, pyridyl, furanyl and thienyl groups, each optionally substituted. Optionally substituted phenyl groups are particularly preferred.

Alternatively, the group $R^1$ can be, for example, an optionally substituted naphthyl group, for example an optionally substituted 1-naphthyl group. One particular example of such a group is unsubstituted 1-naphthyl.

The aryl or heteroaryl group $R^1$ (e.g. a phenyl, pyridyl, furanyl or thienyl group) can be unsubstituted or substituted by up to 5 substituents, and examples of substituents are those listed above in groups $R^{10}$, $R^{10a}$, $R^{10b}$ and $R^{10c}$.

Particular sub-groups of compounds of the formulae (II) or (IIa) consist of compounds in which $R^1$ is unsubstituted phenyl or, more preferably; phenyl bearing 1 to 3 (and more preferably 1 or 2) substituents selected from hydroxy; $C_{1-4}$ acyloxy; fluorine; chlorine; bromine; trifluoromethyl; cyano; $C_{1-4}$ hydrocarbyloxy and $C_{1-4}$ hydrocarbyl groups wherein the $C_{1-4}$ hydrocarbyloxy and $C_{1-4}$ hydrocarbyl groups are each optionally substituted by one or more $C_{1-2}$ alkoxy, halogen, hydroxy or optionally substituted phenyl or pyridyl groups; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; optionally substituted phenyl; optionally substituted pyridyl; and optionally substituted phenoxy; wherein the optional substituent for the phenyl, pyridyl and phenoxy groups are 1, 2 or 3 substituents selected from $C_{1-2}$ acyloxy, fluorine, chlorine, bromine, trifluoromethyl, cyano, and $C_{1-2}$ hydrocarbyloxy and $C_{1-2}$-hydrocarbyl groups wherein the $C_{1-2}$ hydrocarbyloxy and $C_{1-2}$ hydrocarbyl groups are each optionally substituted by methoxy or hydroxy.

More particular sub-groups of compounds within formulae (II) and (IIa) consist of compounds wherein $R^1$ is unsubstituted phenyl or, more preferably, phenyl bearing 1 to 3 (and more preferably 1 or 2) substituents independently selected from hydroxy; $C_{1-4}$ acyloxy; fluorine; chlorine; bromine; trifluoromethyl; cyano; $C_{1-4}$ alkoxy or $C_{1-4}$ alkyl groups wherein the $C_{1-4}$ alkoxy and $C_{1-4}$ alkyl groups are each optionally substituted by one or more fluorine atoms or by $C_{1-2}$ alkoxy, hydroxy or optionally substituted phenyl; $C_{1-4}$ acylamino; benzoylamino; pyrrolidinocarbonyl; piperidinocarbonyl; morpholinocarbonyl; piperazinocarbonyl; optionally substituted phenyl; optionally substituted pyridyl; and optionally substituted phenoxy wherein the optionally substituted phenyl, pyridyl and phenoxy groups are each optionally substituted with 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

Although up to 5 substituents may be present, more typically there are 0, 1, 2, 3 or 4 substituents, preferably 0, 1, 2 or 3, and more preferably 0, 1 or 2.

In one embodiment within each of formulae (II) and (IIa), $R^1$ is unsubstituted phenyl or a phenyl group substituted by 1 or 2 substituents independently selected from hydroxy; $C_{1-4}$ acyloxy; fluorine; chlorine; bromine; trifluoromethyl; trifluoromethoxy; difluoromethoxy; benzyloxy; cyano; $C_{1-4}$ hydrocarbyloxy and $C_{1-4}$ hydrocarbyl each optionally substituted by $C_{1-2}$ alkoxy or hydroxy.

More preferably, the group $R^1$ is a substituted phenyl group bearing 1 or 2 substituents independently selected from fluorine; chlorine; trifluoromethyl; trifluoromethoxy; difluoromethoxy; cyano; methoxy, ethoxy, i-propoxy, methyl, ethyl, propyl, isopropyl, tert-butyl and benzyloxy.

In one sub-group of compounds within each of formulae (II) and (IIa), the group $R^1$ is a phenyl group having a substituent at the para position selected from fluorine, chlorine, trifluoromethyl, trifluoromethoxy, difluoromethoxy, benzyloxy, methyl, tert-butyl and methoxy, and optionally a second substituent at the ortho- or meta-position selected from fluorine, chlorine or methyl. Within this sub-group, the phenyl group can be monosubstituted. Alternatively, the phenyl group can be disubstituted.

In a particular sub-group of compounds within each of formulae (II) and (IIa), the group $R^1$ is a monosubstituted phenyl group having a tert-butyl substituent at the para position.

In another particular sub-group of compounds within each of formulae (II) and (IIa), the group $R^1$ is a monosubstituted phenyl group having a chlorine substituent at the para position.

In a further sub-group of compounds within each of formulae (II) and (IIa), $R^1$ is a dichlorophenyl group, particular examples of which are 2,4-dichlorophenyl, 2,5-dichlorophenyl, 3,4-dichlorophenyl and 2,3-dichlorophenyl.

In each of formulae (II) and (IIa) and the above embodiments, sub-groups and examples thereof:
T is preferably N; and/or
$R^4$ is hydrogen; and/or
$J^1$-$J^2$ represents a group selected from N=CH, HN—C(O), (Me)NC(O), (Et)NC(O) and HC=CH; and/or
$Q^1$ is a bond or a $C_{1-2}$ alkylene group and $Q^2$ is a bond or a methylene group; and/or
G is $NR^2R^3$ and more preferably G is $NH_2$ or NHMe.

Another sub-group of compounds within Formula (II) has the general formula (III):

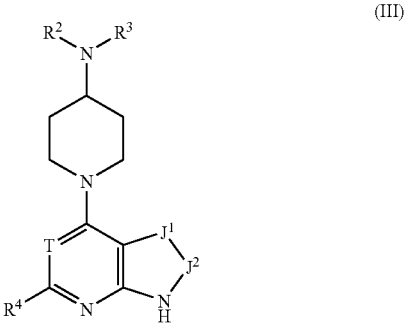

wherein $R^2$, $R^3$, $R^4$, T, $J^1$ and $J^2$ are as defined herein in respect of formula (I) and sub-groups, examples and preferences thereof.

Another sub-group of compounds within formula (II) has the general formula (IV):

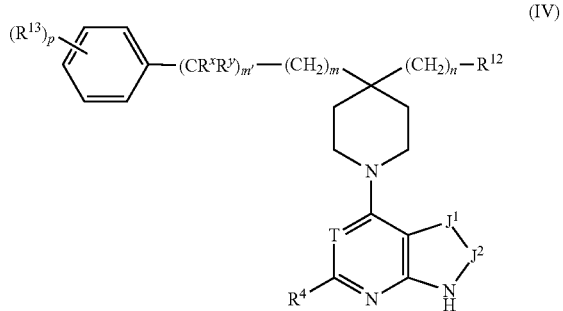

wherein m is 0, 1 or 2; m' is 0 or 1 provided that the sum of m and m' is in the range 0 to 2; n is 0 or 1; p is 0, 1, 2 or 3; $R^x$ and $R^y$ are the same or different and each is selected from hydrogen, methyl and fluorine; $R^{12}$ is CN or $NR^2R^3$ and each $R^{13}$ is independently selected from $R^{10}$, $R^{10a}$, $R^{10b}$ and $R^{10c}$ wherein $J^1$, $J^2$, T, $R^2$, $R^3$, $R^4$, $R^{10}$, $R^{10a}$, $R^{10b}$ and $R^{10c}$ are as defined herein.

In formula (IV), m is preferably 0 or 1. When m' is 0, more preferably m is 1. When m' is 1, preferably m is 0.

In one group of compounds n is 0. In another group of compounds, n is 1.

Preferably p is 0, 1 or 2 and $R^{13}$ is selected from hydroxy; $C_{1-4}$ acyloxy; fluorine; chlorine; bromine; trifluoromethyl; trifluoromethoxy; difluoromethoxy; benzyloxy; cyano; $C_{1-4}$ hydrocarbyloxy and $C_{1-4}$ hydrocarbyl each optionally substituted by $C_{1-2}$ alkoxy or hydroxy.

More preferably, $R^{13}$ is selected from fluorine; chlorine; trifluoromethyl; trifluoromethoxy; difluoromethoxy; cyano; methoxy, ethoxy, i-propoxy, methyl, ethyl, propyl, isopropyl, tert-butyl and benzyloxy.

For example the phenyl group may have a substituent $R^{13}$ at the para position selected from fluorine, chlorine, trifluoromethyl, trifluoromethoxy, difluoromethoxy, benzyloxy, methyl, tert-butyl and methoxy, and optionally a second substituent at the ortho- or meta-position selected from fluorine, chlorine or methyl. Within this sub-group, the phenyl group can be monosubstituted. Alternatively, the phenyl group can be disubstituted.

In another sub-group of compounds, p is 1 and the substituent $R^{13}$ is a tert-butyl substituent at the para position.

In another sub-group of compounds, p is 1 and the substituent $R^{13}$ is a chlorine substituent at the para position.

In another sub-group of compounds, p is 2 and the phenyl group is a dichlorophenyl group, particular examples of which are 2,4-dichlorophenyl, 2,5-dichlorophenyl, 3,4-dichlorophenyl and 2,3-dichlorophenyl.

In one sub-group of compounds within formula (IV), $R^{12}$ is $NR^2R^3$ and more preferably $R^{12}$ is selected from $NH_2$, NHMe and $NMe_2$, with $NH_2$ being particularly preferred.

One particular sub-group of compounds within formula (IV) can be represented by the formula (V):

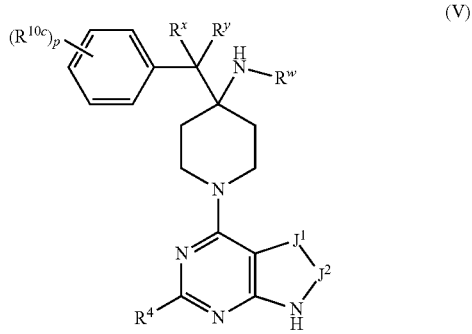

(V)

wherein $J^1$, $J^2$, $R^x$, $R^y$, $R^4$, p and $R^{10c}$ are as defined herein, and $R^w$ is hydrogen or methyl. In one embodiment, $R^w$ is hydrogen. In another embodiment, $R^w$ is methyl. Preferably, p is 0, 1 or 2 and each substituent $R^{10c}$ (when p is 1 or 2) is selected from the substituents listed above in respect of $R^{13}$ and its embodiments, sub-groups and examples.

In formulae (IV) and (V), $R^x$ and $R^y$ may both be hydrogen. Alternatively, $R^x$ and $R^y$ may both be methyl, or may both be fluorine, or one of $R^x$ and $R^y$ may be hydrogen and the other may be methyl or fluorine.

Another sub-group of compounds within formula (II) can be represented by formula (VI)

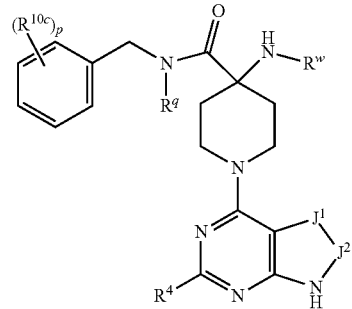

(VI)

wherein $R^q$ is hydrogen or methyl and $R^{10c}$, $R^4$, $R^w$, $J^1$ and $J^2$ are as defined herein.

Preferably, p is 0, 1 or 2 and each substituent $R^{10c}$ (when p is 1 or 2) is selected from the substituents listed above in respect of $R^{13}$ and its embodiments, sub-groups and examples.

In one group of compounds, $R^q$ is hydrogen. In another group of compounds, $R^q$ is methyl.

In one embodiment, $R^w$ is hydrogen. In another embodiment, $R^w$ is methyl.

Compounds of formulae (V) and (VI) show selectivity as inhibitors of PKB relative to PKA.

Particular compounds within formulae (V) and (VI) are those wherein $R^4$ is hydrogen.

In formulae (V) and (VI), the moiety $J^1$-$J^2$ is preferably selected from N=CH, CH=CH, HN—C(O), (Me)NC(O) and (Et)NC(O), and more preferably from N=CH and CH=CH.

In one particularly preferred group of compounds within formulae (V) and (VI), the moiety $J^1$-$J^2$ is CH=CH.

In each of formulae (V) and (VI), one group of preferred substituents $R^{10c}$ consists of chlorine, fluorine, methyl, ethyl, isopropyl, methoxy, difluoromethoxy, trifluoromethoxy, trifluoromethyl, tert-butyl, cyano and benzyloxy.

In each of formulae (V) and (VI), a further group of preferred substituents $R^{10c}$ consists of chlorine, fluorine, methyl, methoxy, difluoromethoxy, trifluoromethoxy, trifluoromethyl, cyano and benzyloxy.

In formulae (V) and (VI), p is preferably 1 or 2.

In one embodiment, p is 1.

In another embodiment, p is 2.

When p is 1, the phenyl ring can be 2-substituted, or 3-substituted, or 4-substituted.

Particular examples of groups wherein p is 1 are the groups A2, A3, A5, A6, A8, A9, A10, A11, A12, A15, A18 and A19 in Table 1 above. More preferred groups are groups A2, A5, A10, A11, A15, A18 and A19 in Table 1.

When p is 2, the phenyl ring can be, for example, 2,3-disubstituted, 2,4-disubsubstituted, or 2,5-disubstituted.

Particular examples of groups wherein p is 2 are the groups A4, A7, A13, A14, A16, A17 and A20 in Table 1.

Another sub-group of compounds of the invention can be represented by the formula (VII):

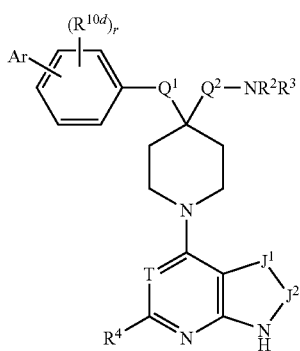

wherein Ar is a 5- or 6-membered monocyclic aryl or heteroaryl group having up to 2 heteroatom ring members selected from O, N and S and being optionally substituted by one or two substituents selected from fluorine, chlorine, methyl and methoxy; $R^{10d}$ is a substituent selected from fluorine, chlorine, methyl, trifluoromethyl, trifluoromethoxy and methoxy; r is 0, 1 or 2 (more typically 0 or 1); and T, $Q^1$, $Q^2$, $NR^2R^3$, $R^4$, and $J^1$-$J^2$ are as defined herein.

In formula (VII), particular 5- or 6-membered monocyclic aryl or heteroaryl groups Ar can be selected from phenyl, pyridyl, furyl and thienyl, each optionally substituted as defined herein. One particular monocyclic aryl group is optionally substituted phenyl, with unsubstituted phenyl being a particular example.

Within formula (VII), preferred compounds are those compounds wherein $NR^2R^3$ is selected from $NH_2$, NHMe and $NMe_2$ (with $NH_2$ being particularly preferred); and/or $R^4$ is hydrogen or methyl (more preferably hydrogen); and/or T is CH or N; and/or $Q^1$ is selected from $CH_2$ and $CH_2NHCO$ (wherein the carbonyl group is attached to the piperidine ring); and/or $Q^2$ is selected from $CH_2$ and a bond (and more preferably is a bond); and/or $J^1$-$J^2$ is selected from CH=N and CH=CH.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^5$ and/or $R^6$ and/or $R^7$ and/or $R^8$ and $R^9$ and/or $R^{10}$ and/or $R^{11}$ and $J^1$-$J^2$ and/or T and/or $Q^1$ and/or $Q^2$ and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the invention are as illustrated in the examples below and include:
methyl-[1-(9H-purin-6-yl)-piperidin-4-yl]-amine;
benzyl-[1-(9H-purin-6-yl)-piperidin-4-yl]-amine;
1-(9H-purin-6-yl)piperidin-4-ylamine;
6-(4-aminopiperidin-1-yl)-7,9-dihydropurin-8-one;
6-(4-benzyl-4-hydroxypiperidin-1-yl)-7,9-dihydropurin-8-one;
6-(piperazin-1-yl)-7,9-dihydropurin-8-one;
(3S)-6-(3-benzyloxymethylpiperazin-1-yl)-7,9-dihydropurin-8-one;
6-(4-phenethylaminopiperidin-1-yl)-7,9-dihydro-purin-8-one;
6-[4-(2-chlorobenzylamino)-piperidin-1-yl]-7,9-dihydro-purin-8-one;
6-[4-(3-chlorobenzylamino)-piperidin-1-yl]-7,9-dihydro-purin-8-one;
1-(1H-pyrazolo[3,4-d]pyrimidin-4-yl)-piperidin-4-ylamine;
1-(7H-pyrrolo[2,3-d]pyrimidin-4-yl)-piperidin-4-ylamine;
1-(1H-pyrrolo[2,3-b]pyridin-4-yl)-piperidin-4-ylamine;
C-[4-(4-chloro-phenyl)-1-(7H-pyrrolo[2,3-d]pyrimidin-4-yl)-piperidin-4-yl]-methylamine;
C-[4-(4-chloro-phenyl)-1-(9H-purin-6-yl)-piperidin-4-yl]-methylamine;
4-benzyl-1-(9H-purin-6-yl)piperidin-4-ylamine;
4-(4-chlorobenzyl)-1-(7H-pyrrolo[2,3-d]pyrimidin-4-yl)piperidin-4-ylamine;
4-(4-chlorobenzyl)-1-(9H-purin-6-yl)piperidin-4-yl amine;
C-[4-(4-chlorobenzyl)-1-(7H-pyrrolo[2,3-d]pyrimidin-4-yl)piperidin-4-yl]methylamine;
6-[4-aminomethyl-4-(4-chlorophenyl)piperidin-1-yl]-7,9-dihydropurin-8-one;
C-[4-(4-chlorophenyl)-1-(1H-pyrrolo[2,3-b]pyridin-4-yl)piperidin-4-yl]methylamine;
6-[4-aminomethyl-4-(4-chlorophenyl)piperidin-1-yl]-7-benzyl-7,9-dihydro-purin-8-one;
6-[4-aminomethyl-4-(4-chlorophenyl)piperidin-1-yl]-7-ethyl-7,9-dihydro-purin-8-one;
C-[4-(4-chlorobenzyl)-1-(9H-purin-6-yl)piperidin-4-yl]methylamine;
4-(4-chlorophenyl)-1-(7H-pyrrolo[2,3-d]pyrimidin-4-yl)piperidine-4-carbonitrile;
4-(4-chlorophenyl)-1-(7H-pyrrolo[2,3-d]pyrimidin-4-yl)piperidin-4-ylamine;
C-[4-(3-chlorophenyl)-1-(7H-pyrrolo[2,3-d]pyrimidin-4-yl)piperidin-4-yl]methylamine;
C-[4-(3-chlorophenyl)-1-(9H-purin-6-yl)piperidin-4-yl]methylamine;
C-[4-(3,4-dichlorophenyl)-1-(7H-pyrrolo[2,3-d]pyrimidin-4-yl)piperidin-4-yl]methylamine;
C-[4-(3,4-dichlorophenyl)-1-(9H-purin-6-yl)piperidin-4-yl]methylamine;
C-[1-(7H-pyrrolo[2,3-d]pyrimidin-4-yl)-4-trifluoromethoxyphenyl)piperidin-4-yl]methylamine;
C-[1-(9H-purin-6-yl)-4-(4-trifluoromethoxyphenyl)piperidin-4-yl]methylamine;
1-(5-phenyl-7H-pyrrolo[2,3-d]pyrimidin-4-yl)-piperidin-4-ylamine;
C-[1-(7H-pyrrolo[2,3-d]pyrimidin-4-yl)-4-(4-trifluoromethylphenyl)piperidin-4-yl]methylamine;
C-[1-(9H-purin-6-yl)-4-(4-trifluoromethylphenyl)piperidin-4-yl]methylamine;
C-[1-(7H-pyrrolo[2,3-d]pyrimidin-4-yl)-4-(3-trifluoromethylphenyl)piperidin-4-yl]methylamine;
C-[1-(9H-purin-6-yl)-4-(3-trifluoromethylphenyl)piperidin-4-yl]methylamine;
C-[4-(3,4-difluorophenyl)-1-(7H-pyrrolo[2,3-d]pyrimidin-4-yl)piperidin-4-yl]methylamine;
C-[4-(3,4-difluorophenyl)-1-(9H-purin-6-yl)piperidin-4-yl]methylamine;
C-[4-(4-methoxyphenyl)-1-(7H-pyrrolo[2,3-d]pyrimidin-4-yl)piperidin-4-yl]methylamine;
C-[4-(4-methoxyphenyl)-1-(9H-purin-6-yl)piperidin-4-yl]methylamine;
C-[4-(4-benzyloxyphenyl)-1-(7H-pyrrolo[2,3-d]pyrimidin-4-yl)piperidin-4-yl]methylamine;
C-[4-(4-benzyloxyphenyl)-1-(9H-purin-6-yl)piperidin-4-yl]methylamine;

[4-(4-chloro-phenyl)-1-(7H-pyrrolo[2,3-d]pyrimidin-4-yl)-piperidin-4-ylmethyl]-methyl-amine;

[4-(4-chlorophenyl)-1-(7H-pyrrolo[2,3-d]pyrimidin-4-yl)-piperidin-4-ylmethyl]-isopropylamine;

[4-(4-chlorobenzyl)-1-(7H-pyrrolo[2,3-d]pyrimidin-4-yl)-piperidin-4-yl]-dimethylamine;

C-[4-(3,4-dichlorobenzyl)-1-(7H-pyrrolo[2,3-d]pyrimidin-4-yl)piperidin-4-yl]methylamine;

C-[4-(3,4-dichlorobenzyl)-1-(9H-purin-6-yl)piperidin-4-yl]methylamine;

C-[1-(7H-pyrrolo[2,3-d]pyrimidin-4-yl)-4-(4-trifluoromethoxybenzyl)piperidin-4-yl]methylamine;

C-[1-(9H-purin-6-yl)-4-(4-trifluoromethoxybenzyl)piperidin-4-yl]methylamine;

4-(3,4-dichlorobenzyl)-1-(7H-pyrrolo[2,3-d]pyrimidin-4-yl)piperidin-4-ylamine;

4-(3,4-dichlorobenzyl)-1-(9H-purin-6-yl)piperidin-4-yl amine;

1-(7H-pyrrolo[2,3-d]pyrimidin-4-yl)-4-(4-trifluoromethoxybenzyl)piperidin-4-ylamine;

1-(9H-purin-6-yl)-4-(4-trifluoromethoxybenzyl)piperidin-4-ylamine;

1-(7H-pyrolo[2,3-d]pyrimidin-4-yl)-4-(3-chlorobenzyl)piperidin-4-ylamine;

4-(4-chlorobenzyl)-1-(1H-pyrrolo[2,3-b]pyridin-4-yl)-piperidin-4-ylamine;

4-(2-chlorobenzyl)-1-(7H-pyrrolo[2,3-d]pyrimidin-4-yl)piperidin-4-ylamine;

4-(4-tert-Butylbenzyl)-1-(7H-pyrrolo[2,3-d]pyrimidin-4-yl)piperidin-4-ylamine;

4-(3-methoxybenzyl)-1-(7H-pyrrolo[2,3-d]pyrimidin-4-yl)piperidin-4-ylamine;

4-(3-trifluoromethoxybenzyl)-1-(7H-pyrrolo[2,3-d]pyrimidin-4-yl)piperidin-4-ylamine;

4-(2,4-dichlorobenzyl)-1-(7H-pyrrolo[2,3-d]pyrimidin-4-yl)piperidin-4-ylamine;

4-(2-chloro-4-fluorobenzyl)-1-(7H-pyrrolo[2,3-d]pyrimidin-4-yl)piperidin-4-ylamine;

4-(2,6-dichlorobenzyl)-1-(7H-pyrrolo[2,3-d]pyrimidin-4-yl)piperidin-4-ylamine;

[4-(4-chlorobenzyl)-1-(7H-pyrrolo[2,3-d]pyrimidin-4-yl)piperidin-4-yl]methylamine;

1-(7H-pyrrolo[2,3-d]pyrimidin-4-yl)-4-(2-trifluoromethoxybenzyl)piperidin-4-ylamine;

4-(2,5-dichlorobenzyl)-1-(7H-pyrrolo[2,3-d]pyrimidin-4-yl)piperidin-4-ylamine;

4-(2,3-dichlorobenzyl)-1-(7H-pyrrolo[2,3-d]pyrimidin-4-yl)piperidin-4-ylamine;

4-(4-tert-butylbenzyl)-1-(1H-pyrrolo[2,3-b]pyridin-4-yl)-piperidin-4-ylamine;

4-(2,4-dichlorobenzyl)-1-(1H-pyrrolo[2,3-b]pyridin-4-yl)-piperidin-4-ylamine;

C-[4-(4-chlorophenyl)-1-(1H-pyrrolo[2,3-b]pyridin-4-yl)-piperidin-4-yl]-methylamine;

4-amino-1-(7H-pyrrolo[2,3-d]pyrimidin-4-yl)-piperidine-4-carboxylic acid 4-chloro-benzylamide;

4-amino-1-(7H-pyrrolo[2,3-d]pyrimidin-4-yl)-piperidine-4-carboxylic acid 3-chloro-benzylamide;

4-amino-1-(7H-pyrrolo[2,3-d]pyrimidin-4-yl)-piperidine-4-carboxylic acid 4-trifluoromethyl-benzylamide;

4-amino-1-(7H-pyrrolo[2,3-d]pyrimidin-4-yl)-piperidine-4-carboxylic acid 4-fluoro-benzylamide;

4-amino-1-(7H-pyrrolo[2,3-d]pyrimidin-4-yl)-piperidine-4-carboxylic acid 2-chloro-benzylamide;

4-amino-1-(7H-pyrrolo[2,3-d]pyrimidin-4-yl)-piperidine-4-carboxylic acid 4-trifluoromethoxy-benzylamide;

4-amino-1-(7H-pyrrolo[2,3-d]pyrimidin-4-yl)-piperidine-4-carboxylic acid (4-chloro-benzyl)-methyl-amide;

4-amino-1-(7H-pyrrolo[2,3-d]pyrimidin-4-yl)-piperidine-4-carboxylic acid 4-tert-butyl-benzylamide;

4-amino-1-(7H-pyrrolo[2,3-d]pyrimidin-4-yl)-piperidine-4-carboxylic acid 2,4-dichloro-benzylamide;

4-amino-1-(7H-pyrrolo[2,3-d]pyrimidin-4-yl)-piperidine-4-carboxylic acid 3,4-dichloro-benzylamide; and 4-(4-chloro-benzyloxymethyl)-1-(7H-pyrrolo[2,3-d]pyrimidin-4-yl)-piperidin-4-ylamine;

[4-amino-1-(7H-pyrrolo[2,3-d]pyrimidin-4-yl)-piperidin-4-yl]-(3,4-dihydro-1H-isoquinolin-2-yl)-methanone;

[4-amino-1-(7H-pyrrolo[2,3-d]pyrimidin-4-yl)-piperidin-4-yl]-(2-phenyl-pyrrolidin-1-yl)-methanone;

4-(4-chlorobenzyl)-1-(1H-pyrazolo[3,4-b]pyridin-4-yl)-piperidin-4-ylamine;

4-(4-tert-butyl-benzyl)-1-(1H-pyrazolo[3,4-b]pyridin-4-yl)-piperidin-4-ylamine;

4-(4-tert-butyl-benzyl)-1-(1H-pyrrolo[2,3-b]pyridin-4-yl)-piperidin-4-ylamine;

N-[4-amino-1-(7H-pyrrolo[2,3-d]pyrimidin-4-yl)-piperidin-4-ylmethyl]-4-chloro-benzamide;

4-biphenyl-4-ylmethyl-1-(7H-pyrrolo[2,3-d]pyrimidin-4-yl)-piperidin-4-ylamine;

4-biphenyl-2-ylmethyl-1-(7H-pyrrolo[2,3-d]pyrimidin-4-yl)-piperidin-4-ylamine;

4-(2-methoxy-benzyl)-1-(7H-pyrrolo[2,3-d]pyrimidin-4-yl)-piperidin-4-ylamine;

4-naphthalen-1-ylmethyl-1-(7H-pyrrolo[2,3-d]pyrimidin-4-yl)-piperidin-4-ylamine;

4-amino-1-(7H-pyrrolo[2,3-d]pyrimidin-4-yl)-piperidine-4-carboxylic acid 4-chloro-2-fluoro-benzylamide;

4-amino-1-(7H-pyrrolo[2,3-d]pyrimidin-4-yl)-piperidine-4-carboxylic acid (biphenyl-3-ylmethyl)-amide;

4-biphenyl-3-ylmethyl-1-(7H-pyrrolo[2,3-d]pyrimidin-4-yl)-piperidin-4-ylamine; and 4-(6-chloro-biphenyl-3-ylmethyl)-1-(7H-pyrrolo[2,3-d]pyrimidin-4-yl)-piperidin-4-ylamine; and salts, solvates, tautomers and N-oxides thereof.

Salts, Solvates. Tautomers, Isomers, N-Oxides. Esters, Pro-drugs and Isotopes

Unless otherwise specified, a reference to a particular compound also includes ionic, salt, solvate, and protected forms thereof, for example, as discussed below.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. As in the preceding sections of this application, all references to formula (I) should be taken to refer also to formulae (Ia), (Ib), (Ic), (Id), (Ie), (II), (IIa), (III), (IV), (V), (VI) and sub-groups thereof unless the context indicates otherwise.

Salt forms may be selected and prepared according to methods described in *Pharmaceutical Salts Properties, Selection, and Use*, P. Heinrich Stahl (Editor), Camille G. Wermuth (Editor), ISBN: 3-90639-026-8, Hardcover, 388 pages, August 2002.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, when $J^1$-$J^2$ is N═$CR^6$, the tautomeric forms A and B are possible for the bicyclic group.

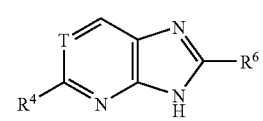

A

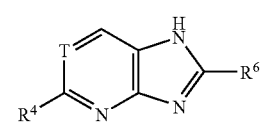

B

When $J^1$-$J^2$ is N═N, the tautomeric forms C and D are possible for the bicyclic group.

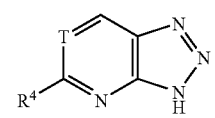

C

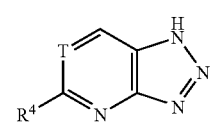

D

When $J^1$-$J^2$ is HN—CO, the tautomeric forms E, F and G are possible for the bicyclic group.

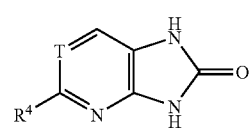

E

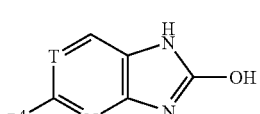

F

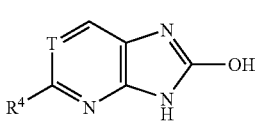

G

All such tautomers are embraced by formula (I).

Other examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

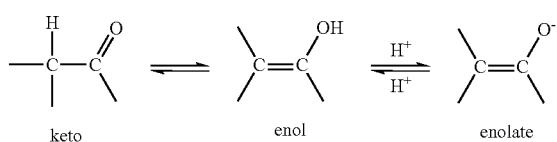

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see Advanced Organic Chemistry by Jerry March, 4$^{th}$ Edition, John Wiley & Sons, New York, 1992, pages 109-114, and see also Cahn, Ingold & Prelog, Angew. Chem. Int. Ed. Engl., 1966, 5, 385-415.

Optical isomers can be separated by a number of techniques including chiral chromatography (chromatography on a chiral support) and such techniques are well known to the person skilled in the art.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1$H, $^2$H(D), and $^3$H(T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I). In one embodiment of the invention, formula (I) includes within its scope esters of compounds of the formula (I) bearing a carboxylic acid group or a hydroxyl group. In another embodiment, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl
(e.g., -Me, -Et, -nPr, -iPr, -nBu, -sBu, -iBu, -tBu);
$C_{1-7}$-aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy) carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in Antibody-directed Enzyme Prodrug Therapy (ADEPT), Gene-directed Enzyme Prodrug Therapy (GDEPT), Polymer-directed Enzyme Prodrug Therapy (PDEPT), Ligand-directed Enzyme Prodrug Therapy (LIDEPT), etc.). For example, the prodrug may be a sugar derivative or other glycoside conjugate, or may be an amino acid ester derivative.

Methods for the Preparation of Compounds of the Formula (I)

In this section, references to compounds of the formula (I) include formulae (Ia), (Ib), (Ic), (Id), (II), (III), (IV), (V), (VI) and each of the sub-groups thereof as defined herein unless the context requires otherwise.

In a further aspect, the invention provides a process for the preparation of a compound of the formula. (I) as defined herein.

Compounds of the formula (I) wherein E is an aryl or heteroaryl group can be prepared by reaction of a compound of the formula (X) with a compound of the formula (XI) where (X) and (XI) may be suitably protected and wherein T, $J^1$, $J^2$, $Q^1$, $Q^2$, G, E, and $R^1$ to $R^5$ are as hereinbefore defined, one of the groups X and Y is chlorine, bromine or iodine or a trifluoromethanesulphonate (triflate) group, and the other one of the groups X and Y is a boronate residue, for example a boronate ester or boronic acid residue.

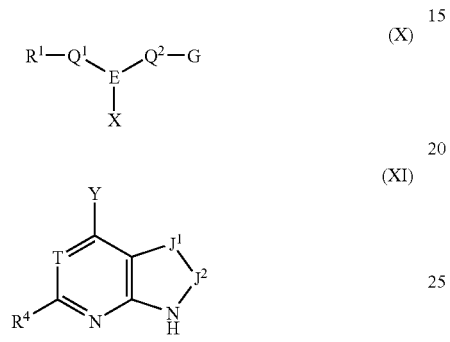

The reaction can be carried out under typical Suzuki Coupling conditions in the presence of a palladium catalyst such as tetrakis(triphenylphosphine)palladium and a base (e.g. a carbonate such as potassium carbonate). The reaction may be carried out in a polar solvent, for example an aqueous solvent such as aqueous ethanol, or an ether such as dimethoxyethane, and the reaction mixture is typically subjected to heating, for example to a temperature of 80° C. or more, e.g. a temperature in excess of 100° C.

An illustrative synthetic route involving a Suzuki coupling step is shown in Scheme 1. In Scheme 1, the bromo compound (XII) in which E is an aryl or heteroaryl group, is converted to a boronic acid (XIII) by reaction with an alkyl lithium such as butyl lithium and a borate ester (iPrO)$_3$B. The reaction is typically carried out in a dry polar solvent such as tetrahydrofuran at a reduced temperature (for example −78° C.).

The resulting boronic acid (XIII) is then reacted with the N-protected chloro compound (XIV) in the presence of bis(triphenylphosphine)palladium under the conditions described above. The protecting group PG (which can be for example a tetrahydropyranyl (THP) group) is then removed by treatment with an acid such as hydrochloric acid to give the compound of the formula (I').

In Scheme 1, where G is other than hydrogen, it is typically protected with a suitable protecting group of which examples are set out below. One particular protecting group which may be used in the context of a Suzuki coupling for protecting an amino group is the tert-butoxycarbonyl group which can be introduced by reacting the amino group with di-tert-butylcarbonate in the presence of a base such as triethylamine. Removal of the protecting group is typically accomplished at the same time as removal of the protecting group PG on the bicyclic group.

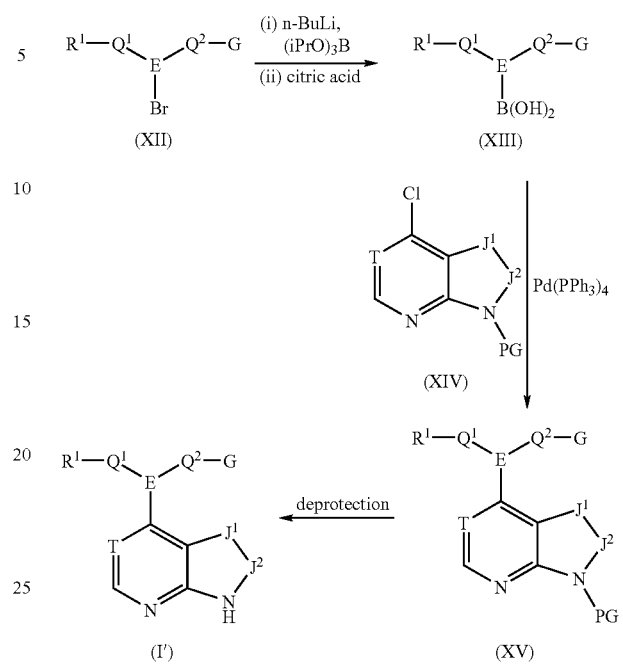

Scheme 1

In the preparative procedure outlined above, the coupling of the aryl or heteroaryl group E to the bicyclic group is accomplished by reacting a halo-purine (or deaza analogue thereof) or halo-aryl or heteroaryl compound with a boronate ester or boronic acid in the presence of a palladium catalyst and base. Many boronates suitable for use in preparing compounds of the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

Compounds of the formula (I) wherein E is a non-aromatic cyclic group and is linked to the bicyclic group by a nitrogen atom can be prepared by the reaction of a compound of the formula (XVI) where T is N, with a compound of the formula (XVII) or a protected derivative thereof, where $R^1$, $Q^1$, $Q^2$ and G are as defined herein and the ring E represents a cyclic group E containing a nucleophilic NH group as a ring member.

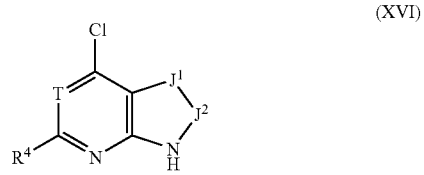

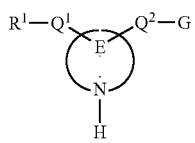

(XVII)

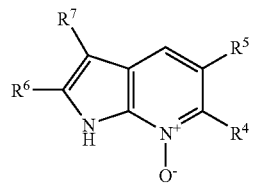

(XIX)

The reaction is typically carried out in a polar solvent such as an alcohol (e.g. ethanol, propanol or n-butanol) at an elevated temperature, for example a temperature in the region from 90° C. to 160° C., optionally in the presence of a non-interfering amine such as triethylamine. The reaction may be carried out in a sealed tube, particularly where the desired reaction temperature exceeds the boiling point of the solvent. When T is N, the reaction is typically carried out at a temperature in the range from about 100° C. to 130° C. but, when T is CH, higher temperatures may be required, for example up to about 160° C., and hence higher boiling solvents such as dimethylformamide may be used. In general, an excess of the nucleophilic amine will be used and/or an additional non-reacting base such as triethylamine will be included in the reaction mixture. Heating of the reaction mixture may be accomplished by normal means or by the use of a microwave heater.

In order to prepare compounds of the formula (I) wherein T is CH, the hydrogen atom of the group CH may be replaced by an activating group in order to facilitate nucleophilic displacement of the chlorine atom by the amine (XVII). The activating group is typically one which can be removed subsequent to the nucleophilic displacement reaction. One such activating group is an ester group such as ethoxycarbonyl or methoxycarbonyl which can be removed by hydrolysis and decarboxylation. Hydrolysis of the ethoxycarbonyl or methoxycarbonyl group to the carboxylic acid is typically carried out using an aqueous alkali such as sodium hydroxide, and the decarboxylation step is typically conducted by heating to an elevated temperature (e.g. 150° C. to 190° C.).

Compounds of the formula (XVI) are commercially available or can be prepared according to methods well known to the skilled person. For example, compounds of the formula (XVI) where T is N and $J^1$-$J^2$ is CH=N can be prepared from the corresponding hydroxy compound by reaction with a chlorinating agent such as $POCl_3$. Compounds of the formula (XVI) where $J^1$-$J^2$ is HN—C(O) can be prepared by the reaction of an ortho-diamino compound of the formula (XVIII) with carbonyl di-imidazole in the presence of a non-interfering base such as triethylamine.

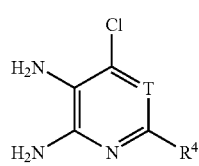

(XVIII)

Compounds of the formula (XVI) where T is $CR^5$ and $J^1$-$J^2$ is $(R^7)$H=CH($R^6$) can be prepared from the corresponding N-oxide of the formula (XIX) by reaction with phosphorus oxychloride at an elevated temperature, for example the reflux temperature of $POCl_3$.

Intermediate compounds of the formula (XVII) wherein E is a piperidine group, $Q^1$ is a saturated hydrocarbon linking group and $Q^1$ and $Q^2$ are both linked to the 4-position of the piperidine group can be prepared by the sequence of reactions shown in Scheme 2.

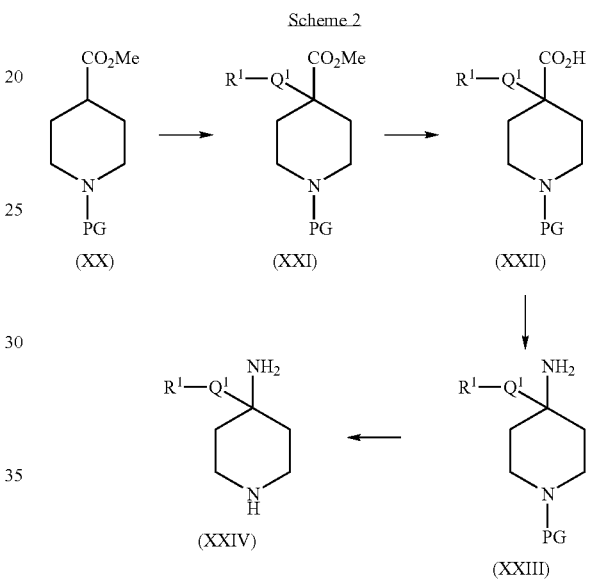

Scheme 2

In Scheme 2, 4-methoxycarbonyl-piperidine is first protected in standard fashion, for example by means of a t-butyloxycarbonyl (boc) group by reaction with di-tert-butylcarbonate in the presence of a non-interfering base to give the protected compound (XX). The protected piperidine carboxymethyl ester (XX) is then alkylated at the α-position relative to the carbonyl group of the ester by reacting with a strong base such as lithium diisopropylamide (LDA) and a compound of the formula $R^1Q^1$-Hal where Hal is a halogen, preferably bromine, and $Q^1$ is a saturated hydrocarbon group. The ester (XXI) is then hydrolysed to the corresponding carboxylic acid (XXII) using an alkali metal hydroxide such as sodium hydroxide. The carboxylic acid (XXII) can be used to prepare a range of different amine intermediates which can, in turn, be converted into compounds of the formula (II). For example, as shown in Scheme 2, the carboxylic acid can be converted to the acid chloride (e.g. by treatment with oxalyl chloride and optionally a catalytic quantity of DMF, or by treatment of a salt of the acid with oxalyl chloride) and then reacted with sodium azide to form the acid azide (not shown). The acid azide can then be heated to bring about rearrangement in a Curtius reaction (see *Advanced Organic Chemistry*, 4$^{th}$ edition, by Jerry March, John Wiley & sons, 1992, pages 1091-1092) to give compound (XXIII) in which the amino group is attached directly to the piperidine ring. The amine (XXIII) is then deprotected according to standard methods (e.g. using hydrochloric acid in the case of a Boc protecting group) and reacted with a compound of the formula (XIV) to give a compound of the formula (I).

In an alternative sequence of reactions, the ester (XXI) can be reduced to the corresponding alcohol which, following deprotection of the piperidine ring nitrogen atom, can be reacted with a compound of the formula (XXI) to give a compound of the formula (I) in which $Q^2$ is $CH_2$ and G is OH. Alternatively, the alcohol can be oxidised to the aldehyde using Dess-Martin periodinane (see Dess, D. B.; Martin, J. C. *J. Org. Soc.*, 1983, 48, 4155 and *Organic Syntheses*, Vol. 77, 141) or tetrapropylammonium perruthenate (TPAP). The resulting aldehyde can be used for a variety of synthetic interconversions such as reductive amination using sodium cyanoborohydride and an amine $HNR^2R^3$ to give a compound of the formula (XVII) in which Q2 is $CH_2$ and G is $HNR^2R^3$.

The carboxylic acid (XXII) can also be converted to an amide by reaction with an amine $HNR^2R^3$ under conditions suitable for forming an amide bond. The coupling reaction between the acid (XXII) and the amine $HNR^2R^3$ is preferably carried out in the presence of a reagent of the type commonly used in the formation of peptide linkages. Examples of such reagents include 1,3-dicyclohexylcarbodiimide (DCC) (Sheehan et al, *J. Amer. Chem. Soc.* 1955, 77, 1067), 1-ethyl-3-(3'-dimethylaminopropyl)-carbodiimide (referred to herein either as EDC or EDAC) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

Where the amine $HNR^2R^3$ is ammonia, the amide coupling reaction can be carried out using 1,1'-carbonyldiimidazole (CDI) to activate the carboxylic acid before addition of the ammonia.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

The resulting amide (not shown) can be reduced using a hydride reducing agent such as lithium aluminium hydride in the presence of aluminium chloride to give the corresponding amine.

Compounds of the formula ((XVII) in which E is a piperidine group, $Q^1$ is a bond and $R^1$ is an aryl or heteroaryl group can be prepared using the sequence of steps shown in Scheme 3.

Scheme 3

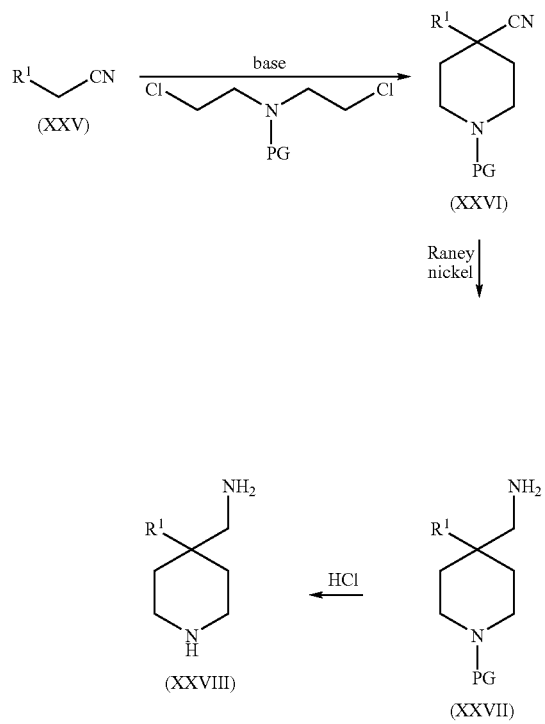

As shown in Scheme 3, the nitrile (XXV) in which $R^1$ is an aryl or heteroaryl group is reacted with a base and N-protected (PG=protecting group) bis-(2-chloroethyl)amine to give the piperidine nitrile (XXVI) which can then be reduced to give the amine (XXVII) using Raney nickel and then deprotected (e.g. using HCl when the protecting group is acid labile) to give amine (XXVIII). Alternatively, the nitrile (XXVI) can be reacted with a compound of the formula (XVI) to give a compound of the formula (I) in which $Q^2$ and G together form a nitrile group.

Compounds of the formula (I) in which E is a piperidine ring, $Q^2$ is a bond and G is an amino group can also be prepared by the reaction sequence shown in Scheme 4.

Scheme 4

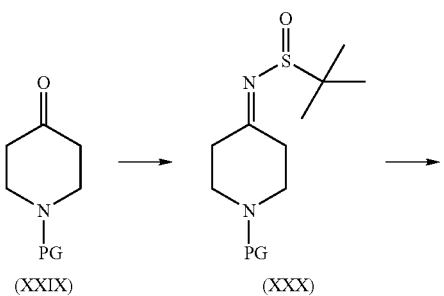

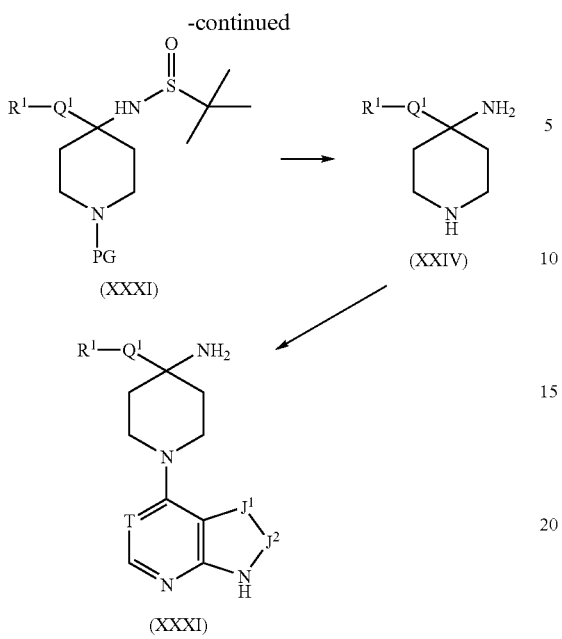

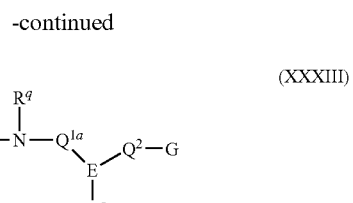

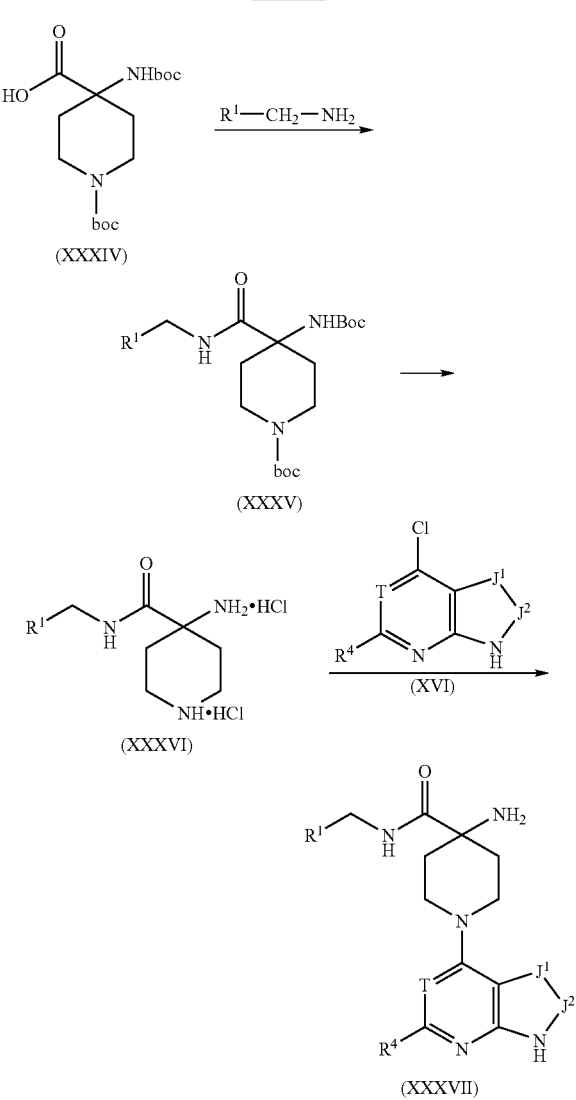

As shown in Scheme 4, a protected 4-piperidone (XXIX), in which PG is a protecting group such as Boc, is reacted with tert-butylsulphinimide in the presence of titanium tetraethoxide in a dry polar solvent such as THF to give the sulphinimine (XXX). The reaction is typically carried out with heating, for example to the reflux temperature of the solvent. The sulphinimine (XXX) is then reacted with an organometallic reagent, for example a Grignard reagent such as an aralkyl or arylmagnesium bromide, suitable for introducing the moiety $R^1$-$Q^1$, to give the sulphinamide (XXXI). The tert-butylsulphinyl group can then be removed by hydrolysis in a hydrochloric acid/dioxane/methanol mixture to give the amine (XXIV). The amine (XXIV) can then be reacted with a chloro-heterocycle (XVI) under the conditions described above to give the product (XXXI), i.e. a compound of the formula (I) in which E is piperidine, $Q^2$ is a bond and G is an amino group.

The corresponding compound wherein $Q^2$ is a bond and G is an alkylamino (e.g. methylamino) group can be prepared from the tert-butylsulphinyl intermediate compound (XXXI) by reaction of the intermediate (XXXI) with a strong base, e.g. a metal hydride such as sodium hydride, followed by the addition of an alkyl halide such as methyl iodide. The reaction is typically carried out in a polar aprotic solvent such as dimethylformamide at a reduced temperature, for example 0-5° C.

Compounds of the formula (I) where $Q^1$ contains an amide bond can be prepared from intermediates of the formulae (XXXII) and (XXXIII) by reaction with intermediate (XI) above using a Suzuki coupling procedure (when $X^L$ is bromine) or by reaction with intermediate (XVI) (when $X^L$ is hydrogen and the group E contains a nucleophilic nitrogen atom) using the methods and conditions described above.

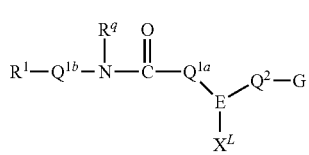

In formulae (XXXII) and (XXXIII), $Q^{1a}$ and $Q^{1b}$ are each a bond or a residue of the group $Q^1$, and $X^L$ is hydrogen or halogen such as bromine. For example, $Q^{1a}$ can be a bond and $Q^{1b}$ can be a group $CH_2$ and vice versa.

The compounds of formulae (XXXII) and (XXXIII) can be prepared by reacting together the appropriate carboxylic acid or activated derivative thereof (e.g. acid chloride) and the appropriate amine using the amide-forming conditions described above.

The formation of compounds of the formula (I) wherein the moiety $Q^1$ contains an amide group is illustrated by the sequence of reactions set out in Scheme 5.

In Scheme 5, the boc-protected piperidine amino acid (XXXIV) is reacted with the arylamine or heteroarylamine $R^1$-$NH_2$ using the amide forming conditions set out above. Thus, for example, the amide-forming reaction can be carried out using HATU (see above) in the presence of a base such as N-ethyldiisopropylamine in a polar solvent such as DMF. The amide (XXXV) is then deprotected; in this case by treatment with acid to remove the boc group; and then reacted with the bicyclic chloro compound (XVI) at elevated temperature (e.g. approximately 100° C.) to give the product (XXXVII). The reaction with the chloro compound is typically carried out in a polar solvent such as a high boiling alcohol (e.g. n-butanol) in the presence of a non-interfering base such as triethylamine.

Compounds of the formula (I) in which $Q^1$ contains an ether linkage can be prepared in a manner analogous to the methods described above for the compounds in which $Q^1$ contains an amide bond. The preparation of compounds containing an ether linkage is illustrated by the sequence of reactions set out in Scheme 6.

Scheme 6

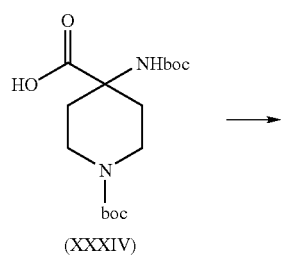

(XXXIV)

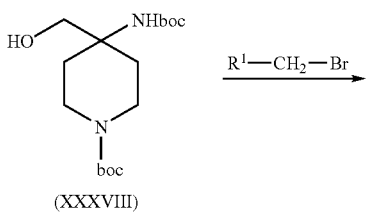

(XXXVIII)

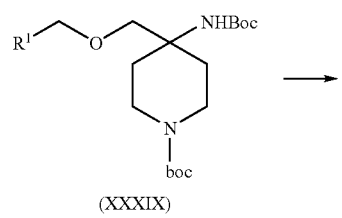

(XXXIX)

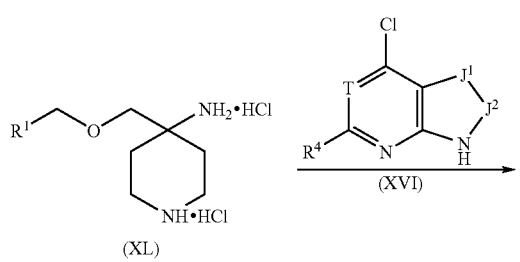

(XL)         (XVI)

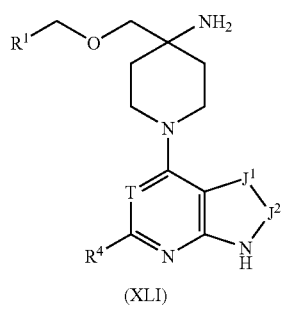

(XLI)

In Scheme 6, the N-protected piperidine amino acid (XXXIV) is reduced to the corresponding alcohol (XXXVIII) using a reducing agent such as lithium aluminium hydride in a polar aprotic solvent such as tetrahydrofuran, typically at around room temperature. The alcohol (XXXVIII) is then treated with a strong base, e.g. a metal hydride such as sodium hydride to form the alcholate which is then reacted with the arylmethyl- or heteroarylmethyl bromide $R^1$-$CH_2$—Br to form the ether (XXXIX). The ether-forming reaction is typically carried out at a reduced temperature (e.g. approximately 0° C. using an aprotic polar solvent such as DMF. The ether is then deprotected by standard methods and the deprotected ether (XL) is reacted with the chloro-compound (XVI) under the conditions described above to give the product (XLI).

Compounds of the formula (I) wherein T is CH, E is a piperidine group and $J^1$-$J^2$ is CH=N or CH=CH can be prepared according to the procedure illustrated in Scheme 7.

Scheme 7

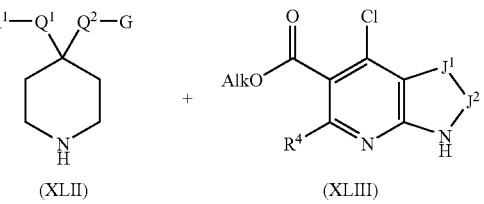

(XLII)         (XLIII)

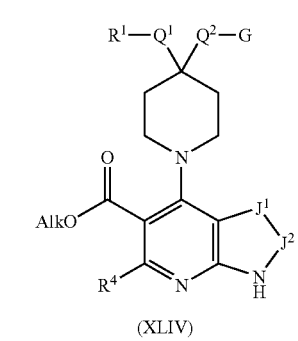

(XLIV)

NaOH 

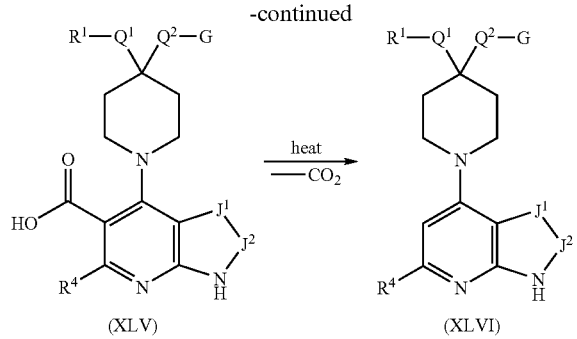

(XLV) → (XLVI) heat, −CO₂

In the sequence of reactions shown in Scheme 7, the starting material is the chlorinated carboxy ester compound (XLIII) which can be prepared by methods generally analogous to methods described in *J. Heterocycl. Chem.* 1972, 235 and *Bioorg. Med. Chem. Lett.* 2003, 2405 followed by removal of any unwanted protecting groups where necessary. In formula (XLIII), AlkO is an alkoxy group, e.g. a $C_{1-3}$ alkoxy group such as methoxy or ethoxy (particularly ethoxy).

The substituted piperidine compound (XLII), suitably protected where necessary, is reacted with the chlorinated carboxy ester compound (XLIII), to give an ester intermediate of the formula (XLIV). The reaction may be carried out in a polar solvent such as a higher boiling alcohol (e.g. n-butanol) in the presence of a non-interfering base such as triethylamine at an elevated temperature (e.g. 90° C. to 130° C., more typically 100° C. to 120° C.). Heating can be effected by means of a microwave heater.

The carboxy ester group in the chlorinated carboxy ester compound (XLIII) functions as an activating group, rendering the chlorine atom more susceptible to nucleophilic displacement. Once the nucleophilic displacement reaction has taken place, the carboxy ester group has served its purpose and can be removed. Accordingly, hydrolysis of the ester intermediate (XLIV) to the carboxylic acid (XLV) is carried out using an aqueous alkali metal hydroxide such as potassium hydroxide or sodium hydroxide with heating where necessary. The carboxylic acid (XLV) is then decarboxylated to give the product (XLVI) by heating to an elevated temperature in excess of 100° C., for example a temperature in the range from about 120° C. to about 180° C.).

Once formed, many compounds of the formula (I) can be converted into other compounds of the formula (I) using standard functional group interconversions.

For example, compounds of the formula (I) or protected forms thereof wherein $J^1$-$J^2$ is CH=N can be converted into the corresponding compound where $J^1$-$J^2$ is N—C(CO) by bromination at the carbon atom in $J^1$-$J^2$ with a brominating agent such as N-bromosuccinimide (NBS) followed by hydrolysis with a mineral acid such as hydrochloric acid.

Other examples of interconversions include the reduction of compounds of the formula (I) in which the $NR^2R^3$ forms part of a nitrile group to the corresponding amine. Compounds in which $NR^2R^3$ is an $NH_2$ group can be converted to the corresponding alkylamine by reductive alkylation, or by formation of the N-Boc derivative and reaction with an alkylating agent such as methyl iodide in the presence of a base. Alternatively, the amine can be converted to a cyclic group by methods well known to the skilled person.

Examples of functional group interconversions and reagents and conditions for carrying out such conversions can be found in, for example, *Advanced Organic Chemistry*, by Jerry March, 4th edition, 119, Wiley Interscience, New York, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0471-31192-8).

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH₃, —OAc). An aldehyde or ketone group may be protected, for example, as an acetal (R—CH(OR)₂) or ketal (R₂C(OR)₂), respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2-(phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$alkyl ester; or a $C_{5-20}$ aryl-$C_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH₂NHC(=O)CH₃).

Isolation and Purification of the Compounds of the Invention

The compounds of the invention can be isolated and purified according to standard techniques well known to the person skilled in the art. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*;

2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Chemical Intermediates

Many of the chemical intermediates described above are novel per se and such novel intermediates form a further aspect of the invention.

Examples of such intermediates include, but are not limited to, protected forms of compounds of the formula (I) and sub-groups thereof, such as protected forms of compounds of the formulae (I'), (XXXI), (XXXVII), (XLI) and (XLVI), as well as compounds of the formulae (XLIV) and (XLV) and protected forms thereof.

Particular examples of compounds of the formula (XLIV) and protected forms thereof include:

4-[4-(4-chlorophenyl)-4-(1,3-dioxo-1,3-dihydroisoindol-2-ylmethyl)-piperidin-1-yl]-1H-pyrrolo[2,3-b]pyridine-5-carboxylic acid ethyl-ester;

4-[4-amino-4-(4-chlorobenzyl)-piperidin-1-yl]-1H-pyrazolo[3,4-b]pyridine-5-carboxylic acid ethyl ester; and 4-[4-amino-4-(4-tert-butyl-benzyl)-piperidin-1-yl]-1H-pyrazolo[3,4-b]pyridine-5-carboxylic acid ethyl ester.

Particular examples of compounds of the formula (XLV) and protected forms thereof include:

4-[4-(4-chlorophenyl)-4-(1,3-dioxo-1,3-dihydroisoindol-2-ylmethyl)-piperidin-1-yl]-1H-pyrrolo[2,3-b]pyridine-5-carboxylic acid;

4-[4-amino-4-(4-chlorobenzyl)-piperidin-1-yl]-1H-pyrazolo[3,4-b]pyridine-5-carboxylic acid; and 4-[4-amino-4-(4-tert-butyl-benzyl)-piperidin-1-yl]-1H-pyrazolo[3,4-b]pyridine-5-carboxylic acid.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g. lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract.

Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Protein Kinase Inhibitory Activity

The activity of the compounds of the invention as inhibitors of protein kinase A and protein kinase B can be measured using the assays set forth in the examples below and the level of activity exhibited by a given compound can be defined in terms of the IC50 value. Preferred compounds of the present invention are compounds having an $IC_{50}$ value of less than 1 µM, more preferably less than 0.1 µM, against protein kinase B.

Some of the compounds of the formula (I) are selective inhibitors of PKB relative to PKA, i.e. the $IC_{50}$ values against PKB are from 5 to 10 times lower, and more preferably greater than 10 times lower, than the $IC_{50}$ values against PKA.

Therapeutic Uses

Prevention or Treatment of Proliferative Disorders

The compounds of the formula (I) are inhibitors of protein kinase A and protein kinase B. As such, they are expected to be useful in providing a means of preventing the growth of or inducing apoptosis of neoplasias. It is therefore anticipated that the compounds will prove useful in treating or preventing proliferative disorders such as cancers. In particular tumours with deletions or inactivating mutations in PTEN or loss of PTEN expression or rearrangements in the (T-cell lytmphocyte) TCL-1 gene may be particularly sensitive to PKB inhibitors. Tumours which have other abnormalities leading to an upregulated PKB pathway signal may also be particularly sensitive to inhibitors of PKB. Examples of such abnormalities include but are not limited to overexpression of one or more PI3K subunits, over-expression of one or more PKB isoforms, or mutations in PI3K, PDK1, or PKB which lead to an increase in the basal activity of the enzyme in question, or upregulation or overexpression or mutational activation of a growth factor receptor such as a growth factor selected from the epidermal growth factor receptor (EGFR), fibroblast growth factor receptor (FGFR), platelet derived growth factor receptor (PDGFR), insulin-like growth factor 1 receptor (IGF-1R) and vascular endothelial growth factor receptor (VEGFR) families.

It is also envisaged that the compounds of the invention will be useful in treating other conditions which result from disorders in proliferation or survival such as viral infections, and neurodegenerative diseases for example. PKB plays an important role in maintaining the survival of immune cells during an immune response and therefore PKB inhibitors could be particularly beneficial in immune disorders including autoimmune conditions.

Therefore, PKB inhibitors could be useful in the treatment of diseases in which there is a disorder of proliferation, apoptosis or differentiation.

PKB inhibitors may also be useful in diseases resulting from insulin resistance and insensitivity, and the disruption of glucose, energy and fat storage such as metabolic disease and obesity.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, esophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukaemias, myelodysplastic syndrome, or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include breast cancer, ovarian cancer, colon cancer, prostate cancer, oesophageal cancer, squamous cancer and non-small cell lung carcinomas.

A further subset of cancers includes breast cancer, ovarian cancer, prostate cancer, endometrial cancer and glioma.

It is also possible that some protein kinase B inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

Immune Disorders

Immune disorders for which PKA and PKB inhibitors may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses

PKB plays a role in apoptosis, proliferation, differentiation and therefore PKB inhibitors could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example osteoporosis and arthritis, aspirin-sensitive rhinosinusitis, cystic fibrosis, multiple sclerosis, kidney diseases.

Methods of Treatment

It is envisaged that the compounds of the formula (I) will useful in the prophylaxis or treatment of a range of disease states or conditions mediated by protein kinase A and/or protein kinase B. Examples of such disease states and conditions are set out above.

Compounds of the formula (I) are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile manner.

A typical daily dose of the compound can be in the range from 100 picograms to 100 milligrams per kilogram of body weight, more typically 10 nanograms to 10 milligrams per kilogram of bodyweight although higher or lower doses may be administered where required. Ultimately, the quantity of compound administered will be commensurate with the nature of the disease or physiological condition being treated and will be at the discretion of the physician.

The compounds of the formula (I) can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topo II inhibitors
Alkylating Agents
Monoclonal Antibodies.
Anti-Hormones
Signal Transduction Inhibitors
Proteasome Inhibitors
DNA methyl transferases
Cytokines and retinoids
Radiotherapy.

For the case of protein kinase A inhibitors or protein kinase B inhibitors combined with other therapies the two or more treatments may be given in individually varying dose schedules and via different routes.

Where the compound of the formula (I) is administered in combination therapy with one or more other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through their common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against protein kinase A and/or protein kinase B.

For example, a biological sample taken from a patient may be analysed to determine whether a condition or disease, such as cancer, that the patient is or may be suffering from is one which is characterised by a genetic abnormality or abnormal protein expression which leads to up-regulation of PKA and/or PKB or to sensitisation of a pathway to normal PKA and/or PKB activity, or to upregulation of a signal transduction component upstream of PKA and/or PKB such as, in the case of PKB, P13K, OF receptor and PDK 1 & 2.

Alternatively, a biological sample taken from a patient may be analysed for loss of a negative regulator or suppressor of the PKB pathway such as PTEN. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of PKA and/or PKB. The term diagnosis includes screening. By marker we include genetic markers including, for example, the measurement of DNA composition to identify mutations of PKA and/or PKB. The term marker also includes markers which are characteristic of up regulation of PKA and/or PKB, including enzyme activity, enzyme levels, enzyme state (e.g. phosphorylated or not) and mRNA levels of the aforementioned proteins.

The above diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, or urine.

Identification of an individual carrying a mutation in PKA and/or PKB or a rearrangement of TCL-1 or loss of PTEN expression may mean that the patient would be particularly suitable for treatment with a PKA and/or PKB inhibitor. Tumours may preferentially be screened for presence of a PKA and/or PKB variant prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of PKB, or detection of PKB variants could be applicable in the present case.

Therefore all of these techniques could also be used to identify tumours particularly suitable for treatment with PKA and/or PKB inhibitors.

For example, as stated above, PKB beta has been found to be upregulated in 10-40% of ovarian and pancreatic cancers (Bellacosa et al 1995, Int. J. Cancer 64, 280-285; Cheng et al 1996, PNAS 93, 3636-3641; Yuan et al 2000, Oncogene 19, 2324-2330). Therefore it is envisaged that PKB inhibitors, and in particular inhibitors of PKB beta, may be used to treat ovarian and pancreatic cancers.

PKB alpha is amplified in human gastric, prostate and breast cancer (Staal 1987, PNAS 84, 5034-5037; Sun et al 2001, Am. J. Pathol. 159, 431-437). Therefore it is envisaged that PKB inhibitors, and in particular inhibitors of PKB alpha, may be used to treat human gastric, prostate and breast cancer.

Increased PKB gamma activity has been observed in steroid independent breast and prostate cell lines (Nakatani et al 1999, J. Biol. Chem. 274, 21528-21532). Therefore it is envisaged that PKB inhibitors, and in particular inhibitors of PKB gamma, may be used to treat steroid independent breast and prostate cancers.

EXPERIMENTAL

The invention will now be illustrated, but not limited, by reference to the specific embodiments described in the following procedures and examples.

The starting materials for each of the procedures described below are commercially available unless otherwise specified.

Proton magnetic resonance ($^1$H NMR) spectra were recorded on a Bruker AV400 instrument operating at 400.13 MHz, in Me-d$_3$-OD at 27° C., unless otherwise stated and are reported as follows: chemical shift E/ppm (number of protons, multiplicity where s=singlet, d=doublet, t=triplet, q=quartet, m=multiplet, br=broad). The residual protic solvent MeOH ($E_H$=3.31 ppm) was used as the internal reference.

In the examples, the compounds prepared were characterised by liquid chromatography and mass spectroscopy using the systems and operating conditions set out below. Where chlorine is present, the mass quoted for the compound is for $^{35}$Cl. The operating conditions used are described below.

Platform System
HPLC System: Waters 2795
Mass Spec Detector: Micromass Platform LC
PDA Detector: Waters 2996 PDA
Polar Analytical Conditions:
Eluent A: H$_2$O (0.1% Formic Acid)
Eluent B: CH$_3$CN (0.1% Formic Acid)
Gradient: 00-50% eluent B over 3 minutes Flow: 1.5 ml/min
Column: Phenomenex Synergi 4µ Hydro 80A, 50x4.6 mm
MS Conditions:
Capillary voltage: 3.5 kV
Cone voltage: 30 V
Source Temperature: 120° C.
Scan Range: 165-700 amu
Ionisation Mode: ElectroSpray Negative, Positive or Positive & Negative
FractionLynx System
System: Waters FractionLynx (dual analytical/prep)
HPLC Pump: Waters 2525
Injector-Autosampler: Waters 2767
Mass Spec Detector: Waters-Micromass ZQ
PDA Detector: Waters 2996 PDA
Acidic Analytical Conditions:
Eluent A: $H_2O$ (0.1% Formic Acid)
Eluent B: $CH_3CN$ (0.1% Formic Acid)
Gradient: 5-95% eluent B over 5 minutes
Flow: 2.0 ml/min
Column: Phenomenex Synergi 4µ Max-RP 80A, 50×4.6 mm
MS Conditions:
Capillary voltage: 3.5 kV
Cone voltage: 25 V
Source Temperature: 120° C.
Scan Range: 125-800 amu
Ionisation Mode: ElectroSpray Positive or ElectroSpray Positive & Negative
LCT System
HPLC System: Waters Alliance 2795 Separations Module
Mass Spec Detector: Waters/Micromass LCT
UV Detector: Waters 2487 Dual λ Absorbance Detector
Polar Analytical Conditions:
Eluent A: Methanol
Eluent B: 0.1% Formic Acid in Water
Gradient:

| Time (mins) | A | B |
|---|---|---|
| 0 | 10 | 90 |
| 0.5 | 10 | 90 |
| 6.5 | 90 | 10 |
| 10 | 90 | 10 |
| 10.5 | 10 | 90 |
| 15 | 10 | 90 |

Flow: 1.0 ml/min
Column: Supelco DISCOVERY $C_{18}$ 5 cm x4.6 mm i.d., 5 µm
MS Conditions:
Capillary voltage: 3500 v (+ve ESI), 3000 v (−ve ESI)
Cone voltage: 40 v (+ve ESI), 50 v (−ve ESI)
Source Temperature: 100° C.
Scan Range: 50-1000 amu
Ionisation Mode: +ve/−ve electrospray ESI (Lockspray™)
LCT System 2
HPLC System: Waters Alliance 2795 Separations Module
Mass Spec Detector: Waters/Micromass LCT
UV Detector: Waters 2487 Dual λ Absorbance Detector
Analytical Conditions:
Eluent A: Methanol
Eluent B: 0.1% Formic Acid in Water
Gradient:

| Time (mins) | A | B |
|---|---|---|
| 0 | 10 | 90 |
| 0.6 | 10 | 90 |
| 1.0 | 20 | 80 |
| 7.5 | 90 | 10 |
| 9 | 90 | 10 |
| 9.5 | 10 | 90 |
| 10 | 10 | 90 |

Flow: 1 ml/min
Column: Supelco DISCOVERY $C_{18}$ 5 cm×4.6 mm i.d., 5 µm
MS Conditions:
Capillary voltage: 3500 v (+ve ESI), 3000 v (−ve ESI)
Cone voltage: 40 v (+ve ESI), 50 v (−ve ESI)
Source Temperature: 100° C.
Scan Range: 50-1000 amu
Ionisation Mode: +ve/−ve electrospray ESI (Lockspray™)

In the examples below, the following key is used to identify the LCMS conditions used:
PS-P Platform System—polar analytical conditions
FL-A FractionLynx System—acidic analytical conditions
LCT1 LCT System 1—polar analytical conditions
LCT2 LCT System 2—polar analytical conditions Example 1

Methyl-[1-(9H-purin-6-yl)-piperidin-4-yl]-amine

1A. {1-[9-(Tetrahydro-pyran-2-yl)-9H-purin-6-yl]-piperidin-4-yl}-carbamic acid tert-butyl ester

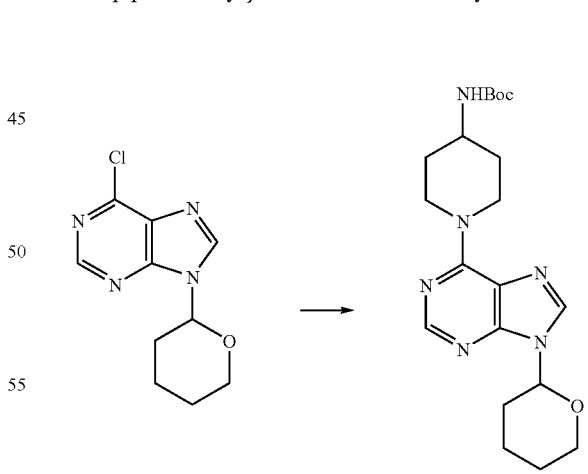

A mixture of 4-(N-Boc-amino)-piperidine (363.2 mg, 1.82 mmol), 9-(tetrahydropyran-2-yl)-6-chloropurine (219.2 mg, 0.92 mmol), n-butanol (9 ml) and triethylamine (0.68 ml, 4.55 mmol) was heated overnight at 100° C. After cooling to room temperature, the solvents were evaporated in vacuo. The crude product was purified by flash silica column chromatography eluting with 5% methanol in dichloromethane to afford the Boc protected compound as a white solid (352.7 mg, 0.88 mmol, 95%) LC-MS (LCT) $R_t$ 6.74 [M+H]$^+$ 403.

1B. Methyl-{1-[9-(tetrahydro-pyran-2-yl)-9H-purin-6-yl]-piperidin-4-yl}-carbamic acid tert-butyl ester

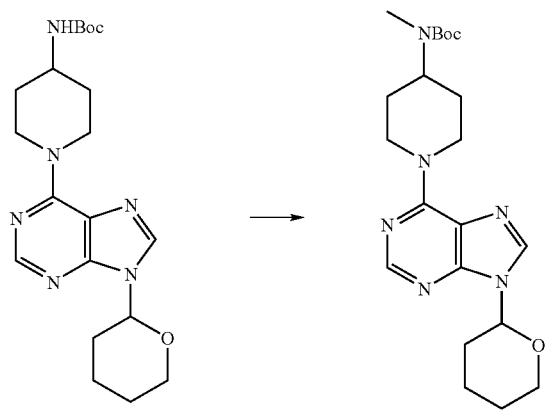 [SMILES: CC(C)(C)OC(=O)NC1CCN(c2ncnc3c2ncn3C2CCCCO2)CC1 ; CN(C(=O)OC(C)(C)C)C1CCN(c2ncnc3c2ncn3C2CCCCO2)CC1]

The {1-[9-(tetrahydro-pyran-2-yl)-9H-purin-6-yl]-piperidin-4-yl}-carbamic acid tert-butyl ester (107.7 mg, 0.27 mmol) of Example 1A was dissolved in anhydrous dimethylformamide (1 ml) and the solution was cooled to 0° C. in an ice bath. Sodium hydride (13 mg, 60% suspension in oil, 0.33 mmol) was added in small portions. The suspension was stirred vigorously for an additional 20 minutes at 0° C. and then the methyl iodide (0.020 ml, 0.32 mmol) was added drop wise. After stirring the reaction mixture for 30 minutes at 0° C. this was brought to room temperature and left stirring additionally overnight. Water (1.2 ml), followed by ethyl acetate (5 ml) was added to the reaction mixture. The organic layer was separated, washed with water, 0.1M HCl, a saturated aqueous NaHCO$_3$ solution, and brine before being dried and concentrated in vacuo. The crude product was purified by flash silica column chromatography eluting with 5% methanol in dichloromethane to afford the required compound as a white solid (83 mg, 0.2 mmol, 73%) LC-MS (LCT) $R_t$ 7.07 [M+H]$^+$ 417.

1C. Methyl-[1-(9H-purin-6-yl)-piperidin-4-yl]-amine

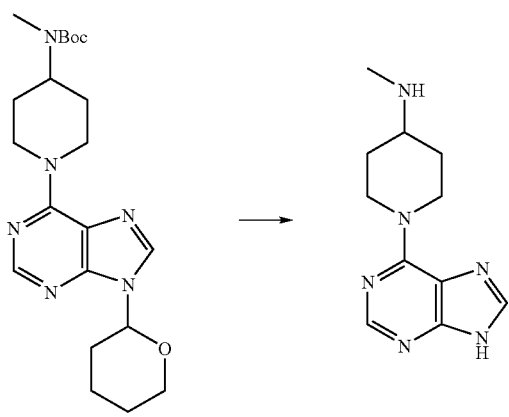 [SMILES: CN(C(=O)OC(C)(C)C)C1CCN(c2ncnc3c2ncn3C2CCCCO2)CC1 ; CNC1CCN(c2ncnc3[nH]cnc23)CC1]

A solution of methyl-{1-[9-(tetrahydro-pyran-2-yl)-9H-purin-6-yl]-piperidin-4-yl}-carbamic acid tert-butyl ester (83 mg, 0.2 mmol), ethanol (4 ml) and 1M aqueous HCl solution (1 ml) was stirred overnight at room temperature. The solvents were then evaporated in vacuo and the crude product was purified with a flash NH$_2$ column (2 g, 15 ml) eluting with methanol to afford the required compound (18 mg, 0.08 mmol, 39%) LC-MS (LCT) $R_t$ 1.27 [M+H]$^+$ 233.

Example 2

Benzyl-[1-(9H-purin-6-yl)-piperidin-4-yl]-amine

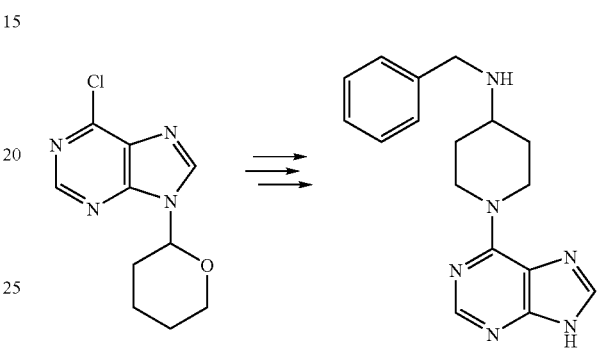

By following the method of Example 1, but using benzyl bromide in place of methyl iodide, the title compound was obtained. LC-MS (LCT) $R_t$ 3.17 [M+H]$^+$ 309

Example 3

1-(9H-Purin-6-yl)piperidin-4-ylamine

3A. [1-(9H-Purin-6-yl)piperidin-4-yl]carbamic acid tert-butyl ester

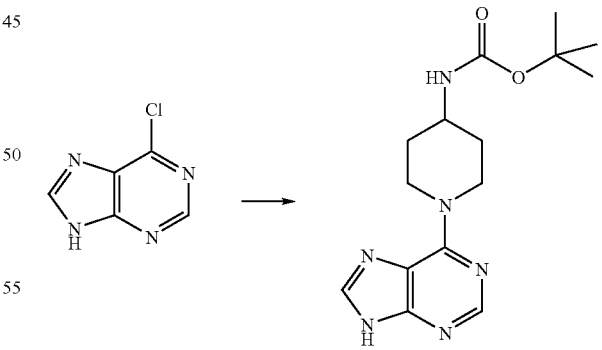

To a mixture of 6-chloropurine (0.050 g, 0.323 mmol) and piperidin-4-yl carbamic acid tert-butyl ester (0.129 g, 0.646 mmol) in n-butanol (3.2 ml) was added triethylamine (0.225 ml, 1.617 mmol). After heating at 100° C. for 20 hours, solvent was removed and the resulting solid triturated with a DCM/methanol mix (3 ml/5 ml). Filtration gave the desired product as a white solid (0.080 g, 78%). LC/MS: (LCT) $R_t$ 5.37 [M+H]$^+$ 319.

3B. 1-(9H-Purin-6-yl)piperidin-4-ylamine

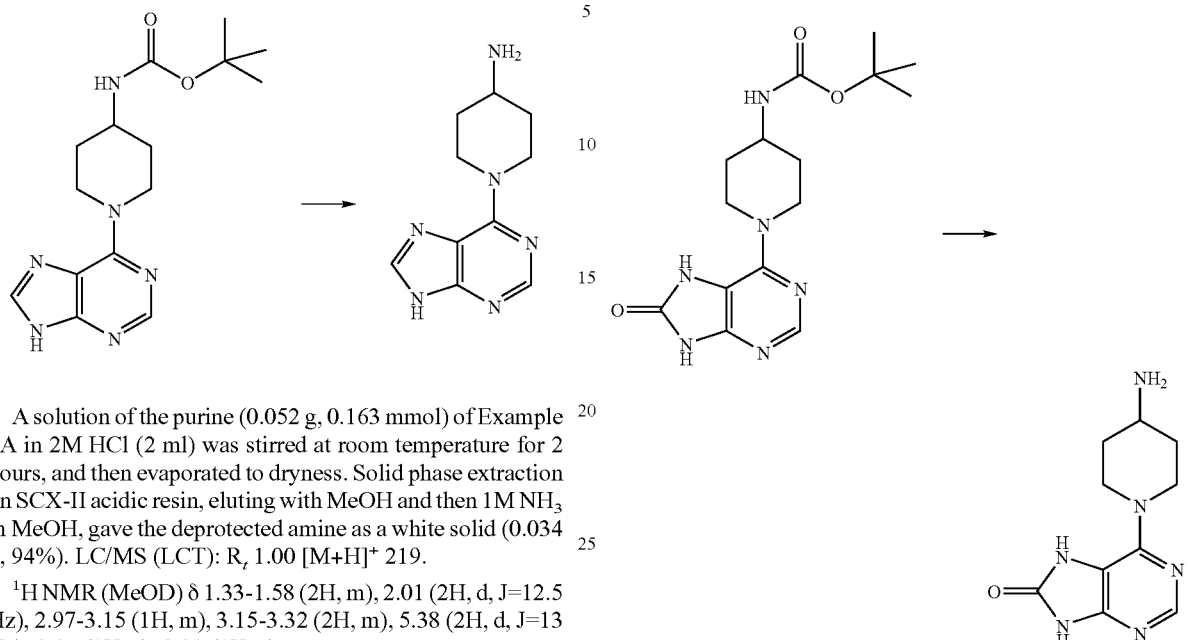

A solution of the purine (0.052 g, 0.163 mmol) of Example 4A in 2M HCl (2 ml) was stirred at room temperature for 2 hours, and then evaporated to dryness. Solid phase extraction on SCX-II acidic resin, eluting with MeOH and then 1M $NH_3$ in MeOH, gave the deprotected amine as a white solid (0.034 g, 94%). LC/MS (LCT): $R_t$ 1.00 [M+H]$^+$ 219.

$^1$H NMR (MeOD) δ 1.33-1.58 (2H, m), 2.01 (2H, d, J=12.5 Hz), 2.97-3.15 (1H, m), 3.15-3.32 (2H, m), 5.38 (2H, d, J=13 Hz), 8.01 (1H, s), 8.21 (1H, s)

Example 4

6-(4-Aminopiperidin-1-yl)-7,9-dihydropurin-8-one

4A. [1-(8-Oxo-8,9-dihydro-7H-purin-6-yl)piperidin-4-yl]carbamic acid tert-butyl ester By reacting 6-chloro-7,9-dihydro-purin-8-one with piperidin-4-yl-carbamic acid tert-butyl ester according to the method of Example 4A, the title compound was obtained. LC/MS: (LCT) $R_t$ 5.68 [M+H]$^+$ 335.

4B. 6-(4-Aminopiperidin-1-yl)-7,9-dihydropurin-8-one

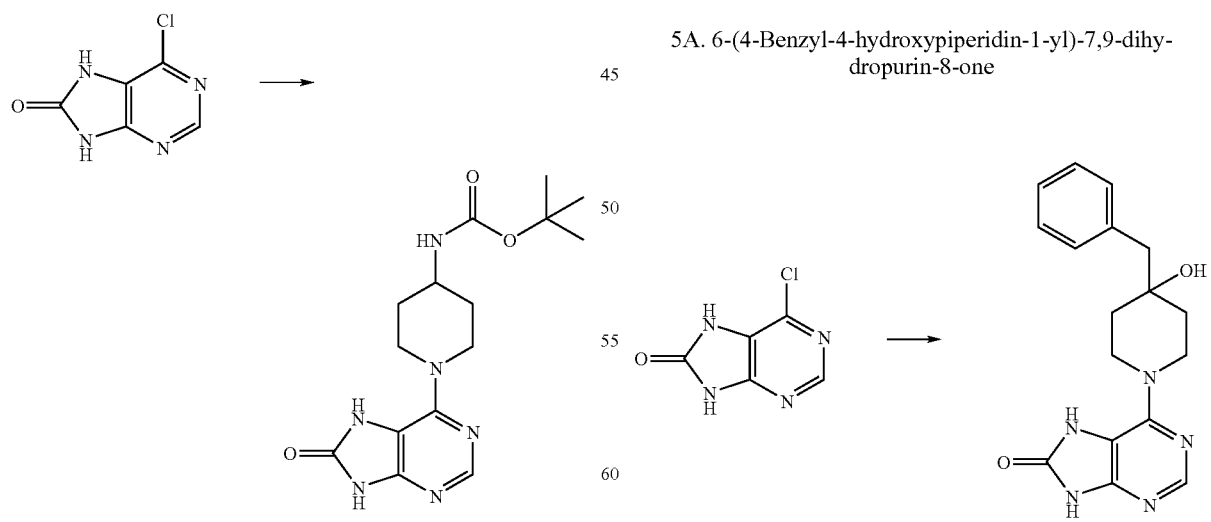

The product of Example 4A was deprotected according to the method of Example 4B to give the title compound. LC/MS (LCT): $R_t$ 1.27 [M+H]$^+$ 235.

$^1$H NMR (MeOD) δ 1.39-1.60 (2H, m), 1.92-2.07 (2H, m), 2.95-3.30 (3H, m), 4.30-4.45 (2H, m), 8.09 (1H, s)

Example 5

6-(4-Benzyl-4-hydroxypiperidin-1-yl)-7,9-dihydropurin-8-one

5A. 6-(4-Benzyl-4-hydroxypiperidin-1-yl)-7,9-dihydropurin-8-one

4-Benzyl-1-methyl-piperidin-4-ol was reacted with 6-chloro-7,9-dihydro-purin-8-one under conditions analogous to those set out in Example 3A to give the title compound LC/MS: (LCT) $R_t$ 5.68 [M+H]$^+$ 326.

By following the method of Example 3A or methods closely similar thereto, but using 6-chloro-7,9-dihydro-purin-8-one instead of 6-chloropurine, the following compounds were prepared.

$^1$H NMR (DMSO) δ 1.38-1.60 (4H, m), 2.70 (2H, s), 3.22-3.35 (2H, m), 3.94 (2H, d, J=13 Hz), 4.44 (1H, br s), 7.18-7.33 (5H, m), 8.05 (1H, s)

Example 6

6-(piperazin-1-yl)-7,9-dihydropurin-8-one

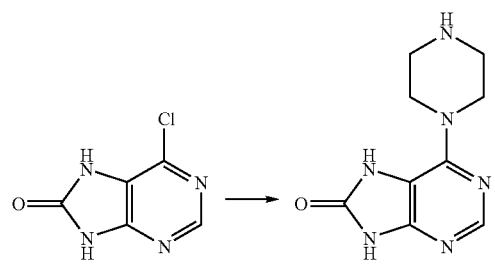 [SMILES: O=c1[nH]c2ncnc(Cl)c2[nH]1 ; O=c1[nH]c2ncnc(N3CCNCC3)c2[nH]1]

LC/MS: (LCT) R$_t$ 1.27 [M+H]$^+$ 221.

$^1$H NMR (d$_6$-DMSO) δ 2.75 (4H, br s), 3.41 (4H, br s), 8.02 (1H, s)

Example 7

(3S)-6-(3-Benzyloxymethylpiperazin-1-yl)-7,9-dihydropurin-8-one

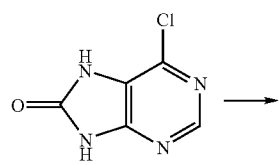

LC/MS: (LCT) R$_t$ 3.88 [M+H]$^+$ 341.

$^1$H NMR (MeOD) δ 2.59-3.08 (5H, m), 3.36-3.50 (2H, m), 3.94-4.11 (2H, m), 4.46 (2H, s), 7.13-7.34 (5H, m), 8.02 (1H, s)

Example 8

6-(4-Phenethylaminopiperidin-1-yl)-7,9-dihydropurin-8-one

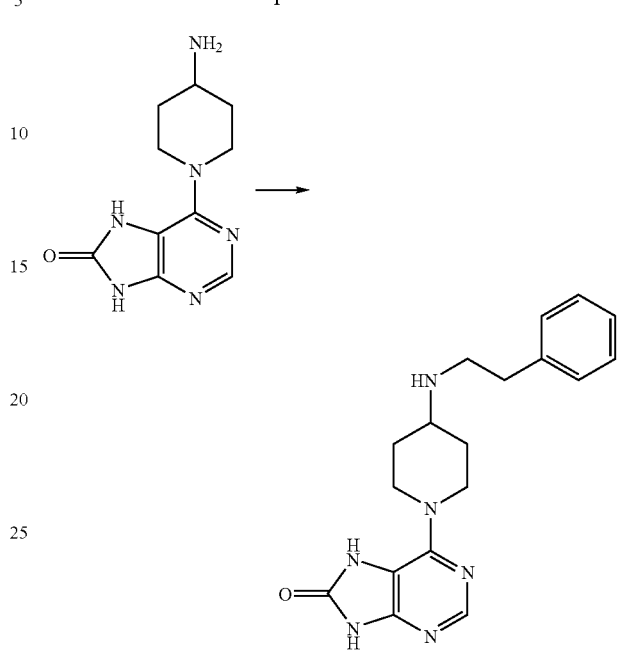

A mixture of 6-(4-aminopiperidin-1-yl)-7,9-dihydropurin-8-one (Example 4B, 0.045 g, 0.20 mmol), phenylacetaldehyde (0.025 ml, 0.20 mmol), NaBH(OAc)$_3$ (0.065 g, 0.30 mmol) and acetic acid (5 drops) in 1,2-dichloroethane (2 ml) and MeOH (0.5 ml) was stirred at room temperature for 2 hours. The solution was absorbed onto a 5 g SCX-II acidic resin cartridge and eluted with MeOH, then 1M NH$_3$-MeOH. The basic eluant was concentrated. Preparative thin layer chromatography (t.l.c.), eluting with 1% NH$_3$ (aq)/9% MeOH/90% CH$_2$Cl$_2$ gave the product as an off white solid (0.007 g, 10%). LC/MS: (LCT) R$_t$ 3.62 [M+H]$^+$ 339.

$^1$H NMR (MeOD) δ 1.34-1.40 (2H, m), 1.92-1.97 (2H, m), 2.61-3.00 (7H, m), 4.20-4.25 (2H, m), 7.11-7.24 (5H, m), 8.01 (1H, s)

Example 9

6-[4-(2-Chlorobenzylamino)-piperidin-1-yl]-7,9-dihydro-purin-8-one

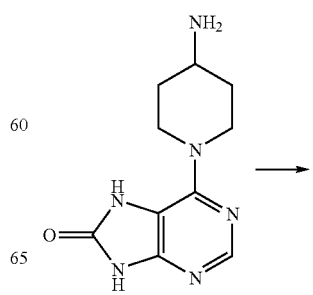

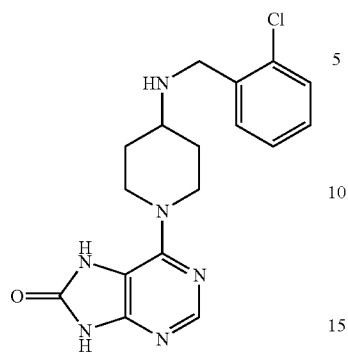

Following the method of Example 8 but using 2-chlorobenzaldehyde instead of phenylacetaldehyde gave the title compound. LC/MS: (LCT) $R_t$ 3.65 [M+H]$^+$ 359, 361.

$^1$H NMR (MeOD) δ 1.30-1.46 (2H, m), 1.95-2.00 (2H, m), 2.70-2.79 (1H, m), 2.92-3.01 (2H, m), 3.88 (2H, s), 4.18-4.23 (2H, m), 7.14-7.41 (4H, m), 8.00 (1H, s)

Example 10

6-[4-(3-Chlorobenzylamino)-piperidin-1-yl]-7,9-dihydro-purin-8-one

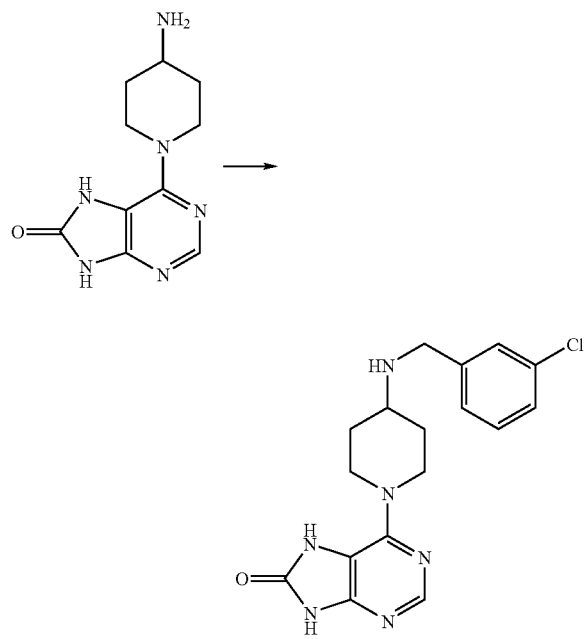

Following the method of Example 8 but using 3-chlorobenzaldehyde instead of phenylacetaldehyde gave the title compound LC/MS: (LCT) $R_t$ 3.77 [M+H]$^+$ 359, 361.

$^1$H NMR (MeOD) δ 1.19-1.44 (2H, m), 1.81-1.96 (2H, m), 2.61-2.76 (1H, m), 2.29-3.00 (2H, m), 4.74 (2H, s), 4.17-4.23 (2H, m), 7.15-7.27 (3H, m), 7.33 (1H, s), 8.00 (1H, s)

Example 11

1-(1H-Pyrazolo[3,4-d]pyrimidin-4-yl)-piperidin-4-ylamine

11A. [1-(1H-Pyrazolo[3,4-d]pyrimidin-4-yl)-piperidin-4-yl]-carbamic acid tert-butyl ester

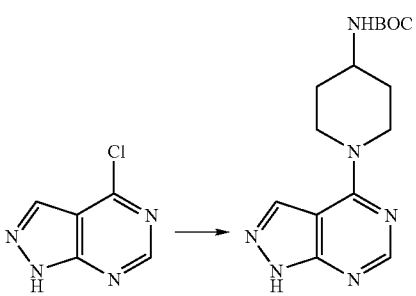

To a solution of 4-chloro-1H-pyrazolo[3,4-d]pyrimidine (*J. Amer. Chem. Soc.* 1957, 79, 6407-6413) (59 mg, 0.38 mmol) in ethanol (2 ml) was added triethylamine (100 μl, 0.72 mmol) and 4-(N-Boc-amino)piperidine (134 mg, 0.67 mmol). The solution was heated at 80° C. for 3 hours, and then cooled to room temperature. The solution was evaporated to dryness and the residue purified by recrystallisation (isopropanol) to yield the product (32 mg, 26% yield).

11B. 1-(1H-Pyrazolo[3,4-d]pyrimidin-4-yl)-piperidin-4-ylamine

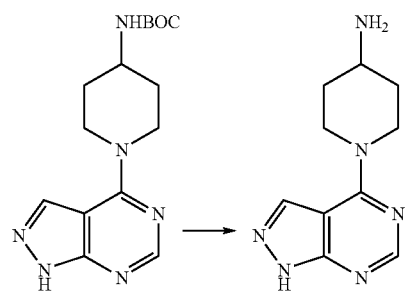

To [1-(1H-pyrazolo[3,4-d]pyrimidin-4-yl)-piperidin-4-yl]-carbamic acid tert-butyl ester (28 mg, 0.088 mmol) was added HCl (1 ml, 4M solution in dioxane, 4 mmol). The suspension was stirred at room temperature for 1 hour, and then diluted with diethyl ether (4 ml). The ethereal layer was discarded and the solid washed with a further portion of diethyl ether (2 ml). The ethereal layer was again discarded, and the resultant solid dried under high vacuum to yield the desired product (34 mg). The free base was liberated by dissolution of this material in methanol, loading onto an acidic resin SCX-2 cartridge, and elution from the cartridge with ammonia in methanol. LC/MS $R_t$ 0.86 [M+H]$^+$ 219

Example 12

1-(7H-Pyrrolo[2,3-d]pyrimidin-4-yl)-piperidin-4-ylamine

12A. 6-Amino-5-(2,2-diethoxy-ethyl)-2-mercapto-pyrimidin-4-ol

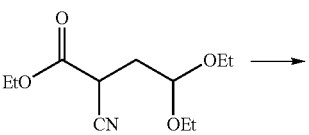

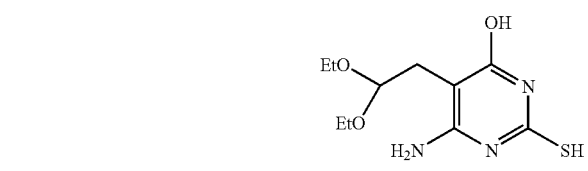

To ethanol (200 ml) was added sodium (2.05 g, 89 mmol) in small portions. The solution was stirred until complete dissolution of the sodium metal. 2-Cyano-4,4-diethoxy-butyric acid ethyl ester (*J. Chem. Soc.*, 1960, 131-138) (9.292 g, 40.5 mmol) was then added as a solution in ethanol (50 ml), followed by addition of thiourea (3.08 g, 40.4 mmol). The solution was heated at 85° C. for 18 hours, and then cooled to room temperature. The solution was concentrated, and saturated aqueous ammonium chloride solution (150 ml) was added. The mixture was stirred at room temperature for 18 hours, after which time the solid was collected by filtration, and washed with water (20 ml) to yield the product (3.376 g, 36%).

12B. 6-Amino-5-(2,2-diethoxy-ethyl)-pyrimidin-4-ol

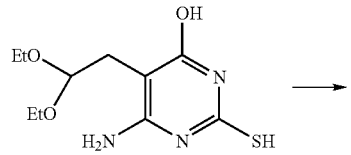

To a suspension of 6-amino-5-(2,2-diethoxy-ethyl)-2-mercapto-pyrimidin-4-ol (1.19 g, 4.6 mmol) in water (50 ml) was added Raney nickel (Aldrich Raney 2800 nickel, 4.8 ml). The mixture was heated at reflux for 1 hour, and then the hot solution was filtered through Celite®. The nickel residue was washed with further water (100 ml), and these washings were filtered through Celite. The aqueous filtrate was evaporated to dryness to yield the title product (0.747 g, 71%).

12C. 7H-Pyrrolo[2,3-d]pyrimidin-4-ol

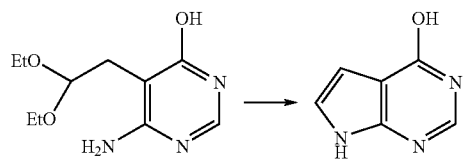 [SMILES: CCOC(Cc1c(N)ncnc1O)OCC ; Oc1ncnc2[nH]ccc12]

This compound was prepared as described in *J. Chem. Soc.*, 1960, pp. 131-138.

12D. 4-Chloro-7H-pyrrolo[2,3-d]pyrimidine

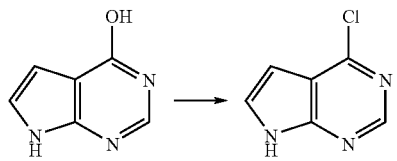 [SMILES: Oc1ncnc2[nH]ccc12 ; Clc1ncnc2[nH]ccc12]

To 7H-pyrrolo[2,3-d]pyrimidin-4-ol (0.425 g, 3.14 mmol) was added phosphorus oxychloride (4 ml). The mixture was heated at reflux for 90 minutes and then cooled to room temperature. The solution was poured onto cracked ice, and extracted with chloroform (3×50 ml) and ethyl acetate (100 ml). The extracts were then dried and concentrated, and the residue obtained triturated with hot ethyl acetate (200 ml) to yield the title compound (0.204 g, 42%).

12E. [1-(7H-Pyrrolo[2,3-d]pyrimidin-4-yl)-piperidin-4-yl]-carbamic acid tert-butyl ester

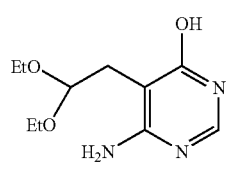

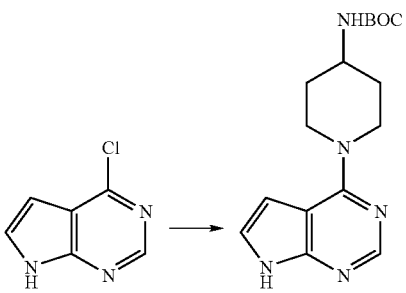

To a solution of 4-chloro-7H-pyrrolo[2,3-a]pyrimidine (74 mg, 0.48 mmol) in ethanol (1 ml) was added triethylamine (200 µl, 1.43 mmol) and 4-N-Boc-aminopiperidine (106 mg, 0.53 mmol). The solution was heated at 80° C. for 4 hours, and then cooled to room temperature. The precipitate was collected by filtration and washed with ethanol (2 ml), then dried under vacuum to yield the product (57 mg, 36%). LC/MS (LCT) $R_t$ 4.57 [M+H]$^+$ 318

12F. 1-(7H-Pyrrolo[2,3-d]pyrimidin-4-yl)-piperidin-4-ylamine

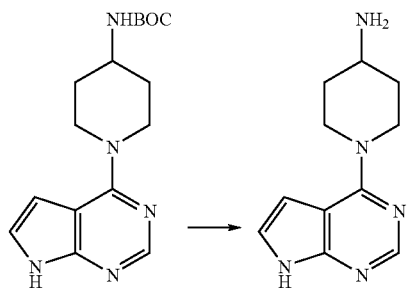

To [1-(7H-Pyrrolo[2,3-d]pyrimidin-4-yl)-piperidin-4-yl]-carbamic acid tert-butyl ester (57 mg, 0.18 mmol) was added HCl (1 ml, 4M solution in dioxane, 4 mmol). The solution was stirred at room temperature for 1 hour, and then diethyl ether was added (4 ml). The ethereal layer was discarded and the solid triturated with a further portion of ether (4 ml) and dried [product mass 27 mg]. A portion of the product was dissolved in methanol, absorbed onto an acidic resin SCX-2 cartridge, and the free base was eluted with 1M ammonia in methanol. LC/MS (LCT) $R_t$ 0.81 [M+H]$^+$ 218

Example 13

1-(1H-Pyrrolo[2,3-b]pyridin-4-yl)-piperidin-4-ylamine 13A. 1H-Pyrrolo[2,3-b]pyridine 7-oxide

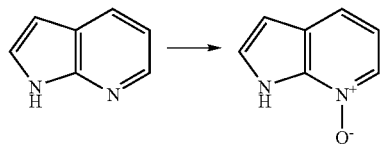 [SMILES: c1cnc2[nH]ccc2c1 ; [O-][n+]1cccc2cc[nH]c21]

To a solution of 7-azaindole (3.04 g, 25 mmol) in DME (60 ml) was added 77% m-chloroperoxybenzoic acid (6.8 g, 12 mmol). The resulting yellow solution was stirred at room temperature for 1.5 hours, during which time the product precipitated. The mixture was filtered and the solid washed with diethyl ether to give 7-hydroxy-1H-pyrrolo[2,3-b]pyridinium m-chlorobenzoate (3.9 g, 13.3 mmol, 53%). A suspension of 7-hydroxy-1H-pyrrolo[2,3-b]pyridinium m-chlorobenzoate (3.9 g, 13.3 mmol) in water (35 ml) was basified to pH 11 with a saturated aqueous solution of potassium carbonate. The 1H-pyrrolo[2,3-b]pyridine 7-oxide started to precipitate. The mixture was kept in the fridge overnight for further precipitation to occur. The solid was filtered, washed with hexane and diethyl ether to afford the required oxide as a white solid (1.35 g, 10 mmol, 40%). LC/MS (LCT) $R_t$ 2.60 [M+H]$^+$ 135.

13B. 4-Chloro-1H-pyrrolo[2,3-b]pyridine

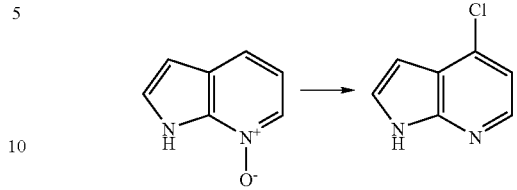

A mixture of 1H-pyrrolo[2,3-b]pyridine 7-oxide (1.35 g, 10 mmol) and phosphorous oxychloride (7.6 ml) was refluxed for 6 hours. After cooling down the reaction mixture to room temperature, ice (90 ml) was added and the mixture was basified to pH 9 with a saturated aqueous solution of potassium carbonate. The brownish solid was filtered, washed with water, hexane and diethyl ether (547 mg, 3.6 mmol, 36%). LC/MS (LCT) $R_t$ 5.74 [M+H]$^+$ 153, 155.

13C. [1-(1H-Pyrrolo[2,3-b]pyridin-4-yl-piperidin-4-yl]-carbamic acid tert-butyl ester

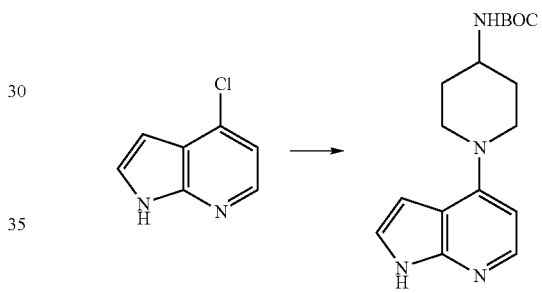

A mixture of 4-chloro-1H-pyrrolo[2,3-b]pyridine (100 mg, 0.64 mmol), 4-N-(Boc-amino)-piperidine (453 mg, 2.24 mmol) and N-methyl-pyrrolidinone (0.2 ml) was microwaved for 1 hour at 160° C. The solution was diluted with methanol and purified through an SCX acidic resin cartridge eluting initially with methanol and then with a 3M solution of ammonia in methanol. The crude product was further purified by flash silica column chromatography eluting with 8% methanol in dichloromethane to afford the required compound (56 mg, 0.18 mmol, 28%). LC/MS (LCT) $R_t$ 14.64 [M+H]$^+$ 317.

13D. 1-(1H-Pyrrolo[2,3-b]pyridin-4-yl)-piperidin-4-ylamine

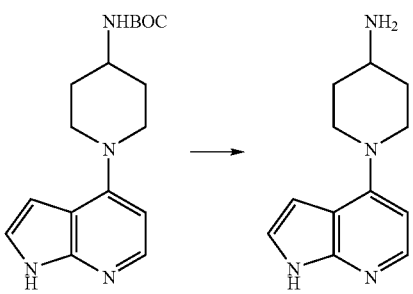

Trifluoroacetic acid (1 ml) was added dropwise to a solution of [1-(1H-pyrrolo[2,3-b]pyridin-4-yl)-piperidin-4-yl]-carbamic acid tert-butyl ester (19 mg, 0.06 mmol) in dichloromethane (1 ml), with stirring and cooling on ice. After 2.5 hours, the solvents were concentrated in vacuo and the crude product was purified on a basic resin $NH_2$ cartridge (2 g, 15 ml) eluting with methanol to afford the required compound (12.5 mg, 0.058 mmol, 96%). LC-MS (LCT) $R_t$ 0.95 [M+H]$^+$ 217

Example 14

C-[4-(4-Chloro-phenyl)-1-(7H-pyrrolo[2,3-d]pyrimidin-4-yl)-piperidin-4-yl]-methylamine 14A.
4-(4-Chlorophenyl)-4-cyanopiperidin-1-carboxylic acid tert-butyl ester

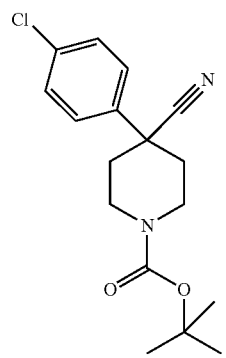 [SMILES: CC(C)(C)OC(=O)N1CCC(C#N)(c2ccc(Cl)cc2)CC1]

4-Chlorophenylacetonitrile was reacted with three equivalents of sodium hydride and one equivalent of N-tert-butyloxycarbonyl-bis-(2-chloroethyl)amine in DMF, initially at room temperature and then at 60° C. to give, after work up, the N-protected piperidine nitrile title compound.

14B. 4-Aminomethyl-4-(4-chlorophenyl)piperidine-1-carboxylic acid tert-butyl ester

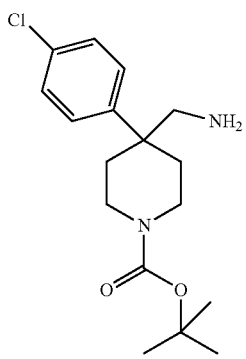 [SMILES: CC(C)(C)OC(=O)N1CCC(CN)(c2ccc(Cl)cc2)CC1]

To a solution of 4-(4-chlorophenyl)-4-cyanopiperidin-1-carboxylic acid tert-butyl ester (0.355 g, 1.107 mmol) in ethanol (20 ml) at room temperature was added Raney Nickel (Raney Nickel 2800, 1 ml) and the suspension stirred under 1 atmosphere of hydrogen for 20 hours. The suspension was filtered through celite and the filtrate concentrated to give the amine as an oil (0.258 g, 69%). LC/MS: (LCT) $R_t$ 5.02 [M—Bu$^t$—NH$_2$]$^+$ 324.

14C.
C-[4-(4-chlorophenyl)piperidin-4-yl]methylamine hydrochloride

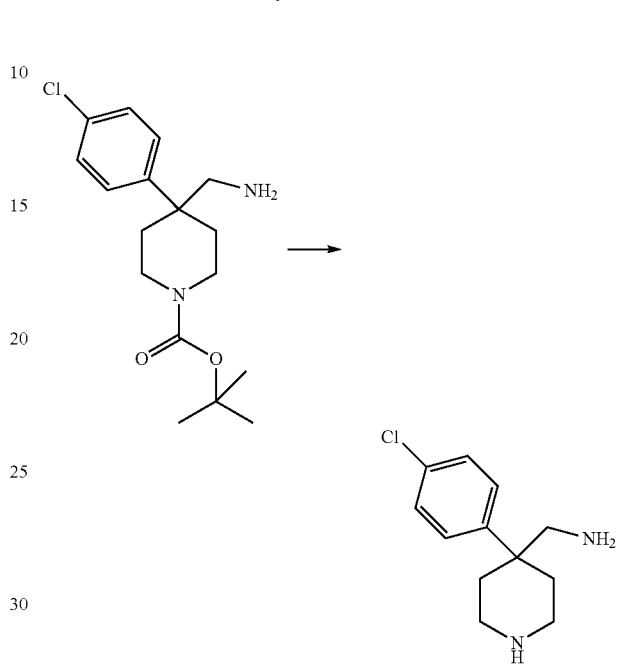

To a solution of 4-aminomethyl-4-(4-chlorophenyl)piperidine-1-carboxylic acid tert-butyl ester (0.258 g, 0.794 mmol) in methanol (10 ml) at room temperature was added 2M hydrochloric acid (10 ml). After 18 h the solution was concentrated to dryness to give the amine salt as a white foam (0.232 g, 98%). $^1$H NMR (MeOD) δ 2.10-2.22 (2H, m), 2.60-2.66 (2H, m), 2.92-3.02 (2H, m), 3.24 (2H, s), 3.37-3.46 (2H, m), 7.51-7.59 (4H, m).

14D. C-[4-(4-Chloro-phenyl)-1-(7H-pyrrolo[2,3-d]pyrimidin-4-yl)-piperidin-4-yl]-methylamine

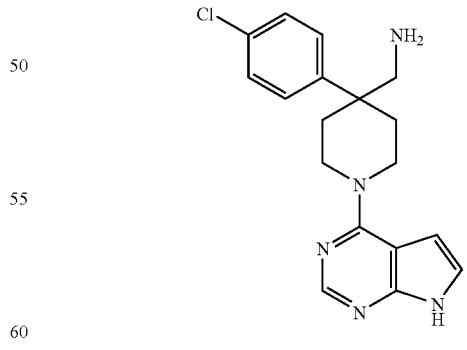

A solution of C-[4-(4-chlorophenyl)piperidin-4-yl]methylamine hydrochloride (0.060 g, 0.202 mmol), 4-chloro-7H-pyrrolo[2,3-d]pyrimidine (0.031 g, 0.202 mmol) and triethylamine (0.14 ml, 1.008 mmol) in n-butanol (2 ml) was heated at 100° C. for 2 days. The reaction mixture was evaporated to dryness and purified by Solid phase extraction on SCX-II acidic resin, eluting with MeOH then 1M NH₃ in MeOH, to give the crude amine. Purification by silica column chromatography (15%-20% methanol in DCM) gave an off white foam solid (0.018 g, 26%). LC/MS (LCT): $R_t$ 3.60 [M+H]⁺ 341.

¹H NMR (MeOD) δ 1.87-1.98 (2H, m), 2.33-2.43 (2H, m), 2.82, (2H, s), 3.45-3.55 (2H, m), 4.43-4.46 (2H, m), 6.65 (1H, d, J=4 Hz), 7.13 (1H, d, J=4 Hz), 7.44-7.52 (4H, m), 8.13 (1H, s)

Example 15

C-[4-(4-Chloro-phenyl)-1-(9H-purin-6-yl)-piperidin-4-yl]-methylamine

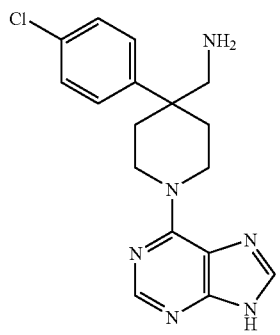 [SMILES: NCC1(c2ccc(Cl)cc2)CCN(c2ncnc3[nH]cnc23)CC1]

The product of Example 14C was reacted with 6-chloropurine following a method analogous to the method of Example 2 to give the title compound. LC/MS: (LCT) $R_t$ 3.91 [M+H]⁺ 342.

¹H NMR (MeOD) δ 1.85-1.95 (2H, m), 3.31-2.46 (2H, m), 2.83 (2H, s), 3.57-3.70 (2H, m), 4.85-5.00 (2H, m), 7.45-7.57 (4H, m), 8.01 (1H, s), 8.20 (1H, s)

Example 16

4-Benzyl-1-(9H-purin-6-yl)piperidin-4-ylamine 16A. 4-Benzylpiperidine-1,4-dicarboxylic acid 1-tert-butyl ester 4-methyl ester

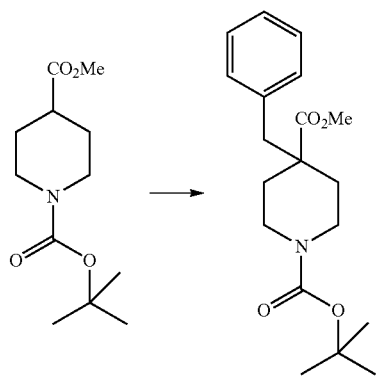 [SMILES: COC(=O)C1CCN(C(=O)OC(C)(C)C)CC1 ; COC(=O)C1(Cc2ccccc2)CCN(C(=O)OC(C)(C)C)CC1]

To a solution of isopropylamine (1.34 ml, 9.559 mmol) in THF (40 ml) at 0° C. was added n-butyllithium (3.65 ml of a 2.5M sol. In hexanes, 9.125 mmol). The resulting LDA solution was added via cannula to a solution of piperidine-1,4-dicarboxylic acid 1-tert-butyl ester 4 methyl ester (2.11 g, 8.690 mmol) in THF (40 ml) and HMPA (8 ml) at −78° C. and stirring continued for 1 hour. Benzyl bromide (1.19 ml, 9.994 mmol) in THF (5 ml) was then added and the solution warmed to room temperature over 2 hours. After stirring for 18 h, saturated aqueous ammonium chloride (200 ml) was added and the aqueous phase extracted with diethyl ether (2×100 ml). Organic phases were combined, dried over magnesium sulphate and concentrated to dryness. Purification by silica column chromatography (0.5% methanol in DCM) gave the ester as an oil (1.816 g, 63%). LC/MS: (LCT) $R_t$ 7.67 [M+H]⁺ 333.

16B. 4-Benzylpiperidine-1,4-dicarboxylic acid mono-tert-butyl ester

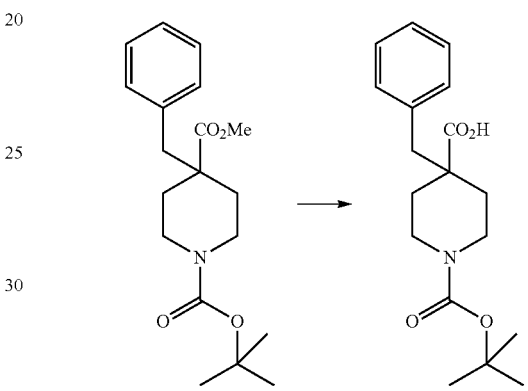

To a solution of 4-benzylpiperidine-1,4-dicarboxylic acid 1-tert-butyl ester 4-methyl ester (1.772 g, 5.315 mmol) in dioxane (24 ml), methanol (12 ml), and water (12 ml) at room temperature was added lithium hydroxide monohydrate (4.460 g, 106.292 mmol). After stirring at 50° C. for 2 days the solution was acidified to pH 6 using 2M HCl and the resulting white precipitate extracted with diethyl ether (2×100 ml). The organic phases were combined, dried over sodium sulphate and concentrated to dryness to give the acid as a white solid (1.477 g, 87%). LC/MS (LCT): $R_t$ 7.37 [M+H]⁺ 319.

16C. 4-Benzyl-1-(9H-purin-6-yl)piperidin-4-ylamine

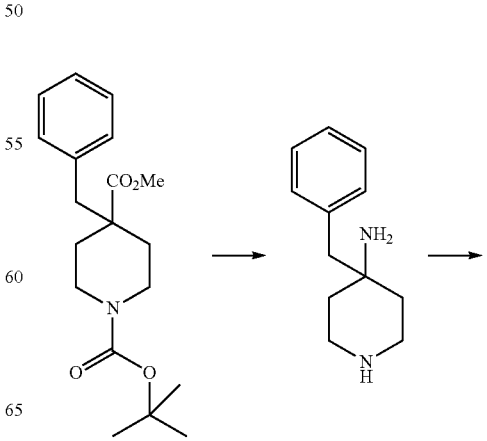

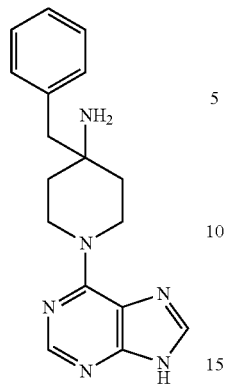

To a mixture of acid (1.467 g, 4.593 mmol) and triethylamine (1.28 ml, 9.186 mmol) in THF (46 ml) at −15° C. was added isobutyl chloroformate (0.901 ml, 6.890 mmol). After 1 h a solution of sodium azide (0.597 g, 9.186 mmol) in water (10 ml) was added and the solution warmed to room temperature overnight. Water (100 ml) was added and the aqueous phase extracted with diethyl ether (3×50 ml). Organic phases were combined, washed with saturated sodium bicarbonate (50 ml) and dried over sodium sulphate. Toluene (100 ml) was added and the overall volume reduced to approximately 90 ml. The resulting solution was warmed to 90° C. for 2 h, then cooled and added to 10% hydrochloric acid (70 ml). The biphasic mixture was warmed to 90° C. for 24 hours. The organic phase was separated and concentrated to dryness to give the crude amine salt (883 mg), which was used without further purification.

A portion of amine salt (0.044 g, 0.1680 mmol), 6-chloropurine (0.026 g, 0.1680 mmol) and triethylamine (0.117 ml, 0.8399 mmol) in n-butanol (1.7 ml) was heated to 100° C. for 24 hours. The mixture was concentrated to dryness then washed with methanol (5 ml), with the resulting solid dissolved in 2M NH$_3$ in methanol and passed through a —NH$_2$ isolute column (2 g). Concentration of the filtrate gave the amine as a solid (0.037 g, 71% from amine salt). LC/MS (LCT): R$_t$ 3.89 [M+H]$^+$ 308.

$^1$H NMR (DMSO) δ 1.51-1.78 (4H, m), 2.88 (2H, s), 3.97-4.21 (4H, m), 7.25-7.40 (5H, m), 8.12 (1H, s), 8.20 (1H, s)

Example 17

4-(4-Chlorobenzyl)-1-(7H-pyrrolo[2,3-d]pyrimidin-4-yl)piperidin-4-ylamine

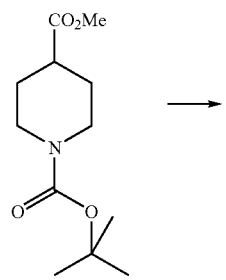

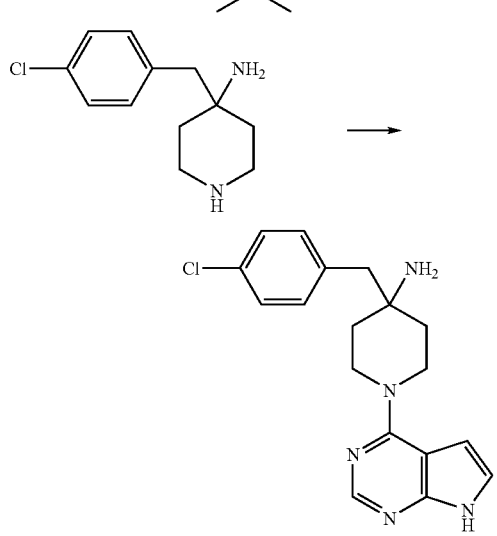

17A. 4-(4-Chlorobenzyl)piperidine-1,4-dicarboxylic acid 1-tert-butyl ester 4-methyl ester To a solution of isopropylamine (3.71 ml, 26.45 mmol) in THF (110 ml) at 0° C. was added n-butyllithium (10.1 ml of a 2.5M solution in hexanes, 25.25 mmol). The resulting LDA solution was added via cannula to a solution of piperidine-1,4-dicarboxylic acid 1-tert-butyl ester 4-methyl ester (5.85 g, 24.04 mmol) in THF (110 ml) and HMPA (20 ml) at −78° C. and stirring was continued for 1 hour. 4-Chlorobenzyl chloride (6.4 ml, 50.49 mmol) in THF (20 ml) was added and the solution was warmed to room temperature over 2 hours. After stirring for 18 hours, saturated aqueous ammonium chloride (500 ml) was added and the aqueous phase was extracted with diethyl ether (2×200 ml). The organic phases were combined, dried over magnesium sulphate and concentrated to dryness. Purification by silica column chromatography (0.5% methanol in DCM) gave the ester as an oil (3.03 g, 34%). LC-MS (LCT1) m/z 390 [M+Na$^+$], R$_t$ 8.02 min.

17B. 4-(4-Chlorobenzyl)piperidine-1,4-dicarboxylic acid mono-tert-butyl ester To a solution of 4-(4-chlorobenzyl)piperidine-1,4-dicarboxylic acid 1-tert-butyl ester 4-methyl ester (1.515 g, 4.117 mmol) in dioxane (20 ml), methanol (10 ml) and water (10 ml) at room temperature was added lithium hydroxide monohydrate (3.455 g, 82.341 mmol). After stirring at 50° C. for 2 days the solution was acidified to pH 6 with 2M HCl and the resulting white precipitate was extracted with diethyl ether (2×100 ml). The organic phases were combined, dried over sodium sulphate and concentrated to dryness, to give the acid as a white solid (1.460 g, 100%). LC-MS (LCT) m/z 376 [M+Na$^+$], R$_t$ 7.62 min.

17C. 4-(4-Chlorobenzyl)piperidin-4-yl amine

To a mixture of the acid (1.46 g, 4.126 mmol) and triethylamine (1.15 ml, 8.252 mmol) in THF (41 ml) at −15° C. was added isobutyl chloroformate (0.812 ml, 6.189 mmol). After 1 hour, a solution of sodium azide (0.536 g, 8.252 mmol) in water (10 ml) was added and the solution was warmed to room temperature overnight. Water (100 ml) was added and the aqueous phase was extracted with diethyl ether (3×50 ml). The organic phases were combined, washed with saturated sodium bicarbonate (50 ml) and dried over sodium sulphate. Toluene (100 ml) was added and the overall volume was reduced to approximately 90 ml. The resulting solution was warmed to 90° C. for 2 h, then cooled and added to 10% hydrochloric acid (70 ml). The biphasic mixture was warmed to 90° C. for 24 hours. The organic phase was separated and concentrated to dryness to give the crude amine salt (1.109 g).

The crude amine salt was dissolved in 2M NaOH (20 ml) and di-tert-butyl dicarbonate (1.61 g, 7.391 mmol) added. After 2 days the aqueous phase was extracted with diethyl ether (2×50 ml). The organic phases were combined, washed with 1M HCl (20 ml), saturated sodium bicarbonate (20 ml) and brine (20 ml), then dried over magnesium sulphate and concentrated. Purification by column chromatography (50% diethyl ether in hexanes) gave the doubly BOC-protected amine (0.685 g), which was subsequently deprotected by stirring with 4M HCl in dioxane (10 ml) and methanol (10 ml) at room temperature for 2 days. Concentration gave the desired amine as the bis-hydrochloride salt (0.492 g, 40% from acid).

$^1$H NMR (MeOD) δ 7.48-7.44 (m, 2H), 7.35-7.32 (m, 2H), 3.53-3.47 (4H, m), 3.21 (s, 2H), 2.18-2.13 (4H, m).

17D. 4-(4-Chlorobenzyl)-1-(7H-pyrrolo[2,3-d]pyrimidin-4-yl)piperidin-4-ylamine A solution of 4-(4-chlorobenzyl)piperidin-4-yl amine hydrochloride (0.060 g, 0.2016 mmol), 4-chloro-7H-pyrrolo[2,3-d]pyrimidine (0.031 g, 0.2016 mmol) and triethylamine (0.140 ml, 1.0079 mmol) in n-butanol (2.0 ml) was heated to 100° C. for 24 hours. Concentration and purification by preparative silica TLC gave a white solid (0.034 g, 49%). LC-MS (LCT) m/z 342 [M+H$^+$], R$_t$ 3.25 min.

$^1$H NMR (MeOD) δ 1.53-1.94 (4H, m), 2.81 (2H, s), 3.75-3.90 (2H, m), 4.21-4.41 (2H, m), 6.64 (1H, d, J=4 Hz), 7.13 (1H, J=4 Hz), 7.27-7.36 (4H, m), 8.14 (1H, s)

Example 18

4-(4-Chlorobenzyl)-1-(9H-purin-6-yl)piperidin-4-yl amine

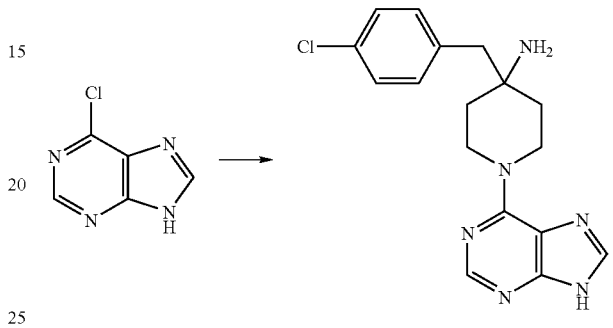

The title compound was prepared as described in Example 17 using 6-chloropurine in place of 4-chloro-7H-pyrrolo[2,3-d]pyrimidine. LC-MS (LCT) m/z 343 [M+H$^+$], R$_t$ 4.02 min.

$^1$H NMR (MeOD) δ 1.40-1.74 (4H, m), 2.68 (2H, s), 3.79-3.89 (2H, m), 4.59-4.77 (2H, m), 7.10-7.23 (4H, m), 7.89 (1H, s), 8.08 (1H, s)

Example 19

C-[4-(4-Chlorobenzyl)-1-(7H-pyrrolo[2,3-d]pyrimidin-4-yl)piperidin-4-yl]methylamine

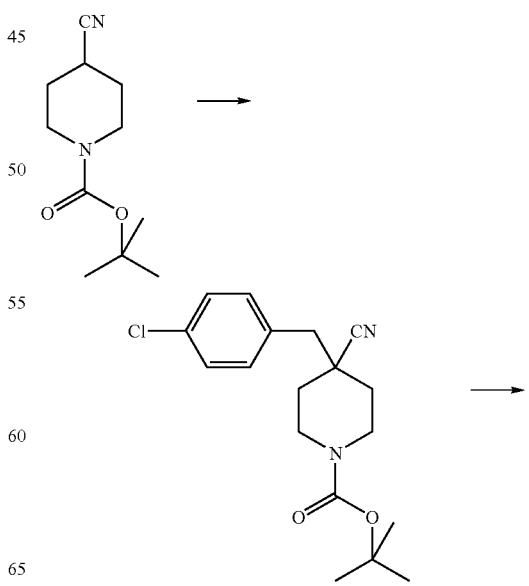

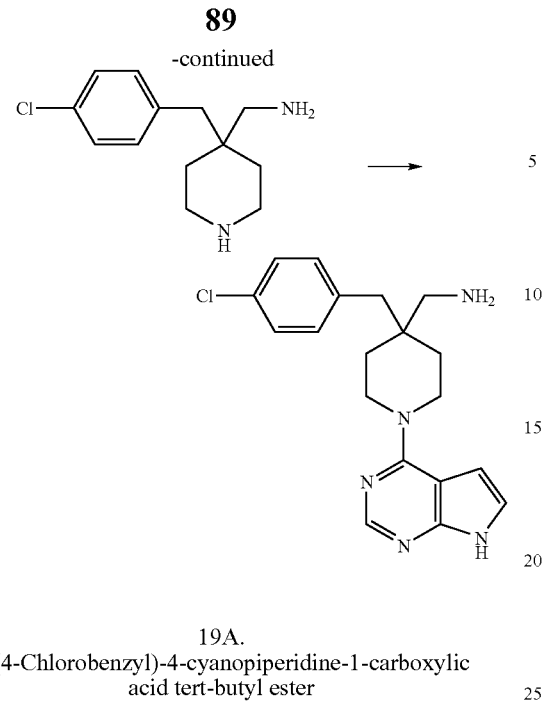

19A.
4-(4-Chlorobenzyl)-4-cyanopiperidine-1-carboxylic acid tert-butyl ester To a solution of isopropylamine (1.53 ml, 10.94 mmol) in THF (30 ml) at −78° C. was added n-butyllithium (4.38 ml of a 2.5M solution in hexanes, 10.938 mmol). After 10 minutes, a solution of 4-cyanopiperidine-1-carboxylic acid tert-butyl ester in THF (12 ml) was added. After a further 1 hour, a solution of 4-chlorobenzyl chloride (1.84 g, 11.4 mmol) in THF (5 ml) was added and the solution warmed to room temperature over 15 hours. Water (150 ml) was added and the aqueous phase extracted with diethyl ether (150 ml). The organic phase was dried over magnesium sulphate and concentrated to give a crude solid that was purified by recrystallisation from diethyl ether/hexane in two batches to give the product as a white solid (2.650 g, 83%). LC-MS (LCT2) m/z 357 [M+Na$^+$], 235 [M-Boc]$^+$, R$_t$ 8.02 min.

19B. C-[4-(4-Chlorobenzyl)piperidin-4-yl]methyl amine

To a solution of 4-(4-chlorobenzyl)-4-cyanopiperidine-1-carboxylic acid tert-butyl ester (0.500 g, 1.493 mmol) in methanol (3 ml) was added 4M HCl in dioxane (10 ml). After stirring for 19 hours, the solution was concentrated to give the deprotected amine as the hydrochloride salt (0.405 g).

The amine salt was dissolved in 1M BH$_3$.THF in THF (15 ml, 15 mmol) at room temperature and stirred for 2 days. The reaction was quenched with methanol (10 ml), concentrated, redissolved in methanol (10 ml) and 4M HCl in dioxane (20 ml) and the resulting solution refluxed for 6 hours. Concentration and purification by SCX-2 Isolute column (5 g), eluting with 1M NH$_3$/MeOH, gave the desired amine, which was converted to the bis-hydrochloride salt by dissolving in 2M aqueous HCl (6 ml) and methanol (6 ml) followed by concentration to give the product as a white solid (0.285 g, 61%).
$^1$H NMR (MeOD)-free amine-δ 7.31-7.28 (m, 2H), 7.20-7.17 (m, 2H), 2.94-2.75 (m, 4H), 2.70 (s, 2H), 2.52 (s, 2H), 1.45-1.41 (m, 4H).

19C. C-[4-(4-Chlorobenzyl)-1-(7H-pyrrolo[2,3-d]pyrimidin-4-yl)piperidin-4-yl]methylamine A solution of C-[4-(4-chlorobenzyl)piperidin-4-yl]methyl amine hydrochloride (0.063 g, 0.2016 mmol), 4-chloro-7H-pyrrolo[2,3-d]pyrimidine (0.031 g, 0.2016 mmol) and triethylamine (0.140 ml, 1.0079 mmol) in n-butanol (2.0 ml) was heated to 100° C. for 24 hours. Concentration and purification by SCX-2 Isolute column (2 g), eluting with 1M NH$_3$/MeOH, followed by silica column chromatography (15% methanol in DCM) gave a white solid (0.040 g, 56%). LC-MS (LCT2) m/z 356 [M+H$^+$], R$_t$ 2.97 min.
$^1$H NMR (MeOD) δ 1.61 (4H, br s), 2.62 (2H, s), 2.79 (2H, s), 3.90-3.94 (2H, m), 4.05-4.08 (2H, m), 6.63 (1H, d, J=3 Hz), 7.12 (J=3 Hz), 7.22-7.32 (4H, m), 8.13 (1H, s)

Example 20

6-[4-Aminomethyl-4-(4-chlorophenyl)piperidin-1-yl]-7,9-dihydropurin-8-one

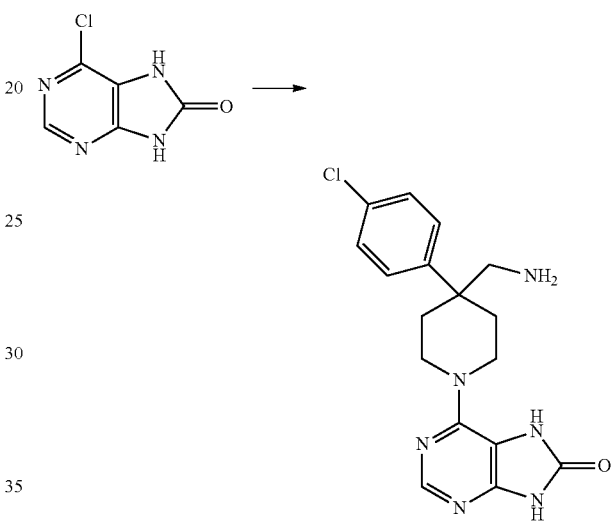

The title compound was prepared as described in Example 14 using 6-chloro-8-oxopurine in place of 4-chloro-7H-pyrrolo[2,3-d]pyrimidine. LC-MS (LCT) m/z 359 [M+H$^+$], R$_t$ 4.09 min.
$^1$H NMR (MeOD) δ 1.84-1.98 (2H, m), 2.30-2.42 (2H, m), 2.82 (2H, s), 3.24-3.40 (2H, m), 3.94-4.10 (2H, m), 7.42-7.49 (4H, m), 8.11 (1H, s)

Example 21

C-[4-(4-Chlorophenyl)-1-(1H-pyrrolo[2,3-b]pyridin-4-yl)piperidin-4-yl]methylamine

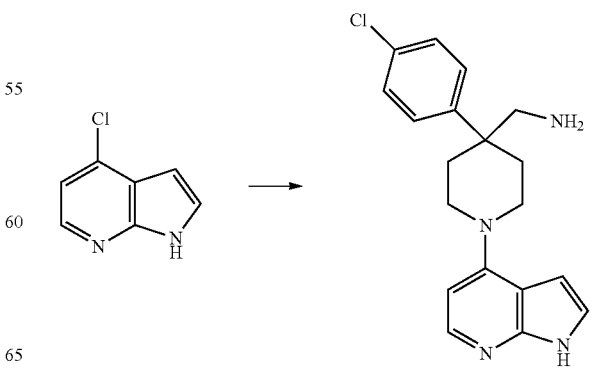

The title compound was prepared in a similar manner to Example 14, using 4-chloro-7-azaindole in place of 4-chloro-7H-pyrrolo[2,3-d]pyrimidine, with NMP as solvent and microwave heating at 155° C. LC-MS (LCT2) m/z 341 [M+H$^+$], R$_t$ 2.85 min.

$^1$H NMR (MeOD) δ 1.98-2.13 (2H, m), 2.37-2.49 (2H, m), 2.84 (2H, s), 3.18-3.28 (2H, m), 3.76-3.90 (2H, m), 6.46 (1H, d, J=6 Hz), 6.54 (1H, d, J=3.5 Hz), 7.18 (1H, d, J=3.5 Hz), 7.42-7.51 (4H, m), 7.91 (1H, d, J=6 Hz)

Example 22

6-[4-Aminomethyl-4-(4-chlorophenyl)piperidin-1-yl]-7-ethyl-7,9-dihydro-purin-8-one

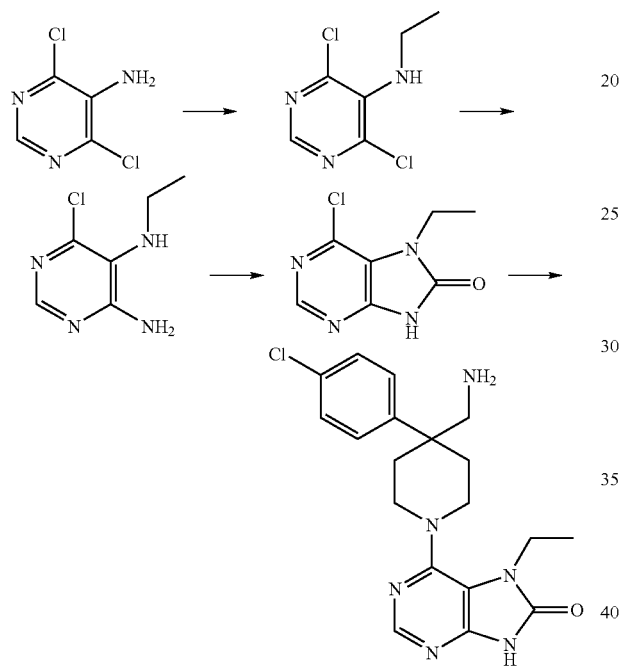

22A. Ethyl(4,6-dichloropyrimidin-5-yl)amine

Sodium hydride (55%, 0.17 g, 4.0 mmol) was added in a single portion to a solution of (4,6-dichloropyrimidin-5-yl)amine (0.61 g, 3.72 mmol) and ethyl iodide (0.30 mL, 3.8 mmol) in dry DMF (3 mL) at room temperature. The suspension was stirred for 18 hours, then diluted with saturated aqueous ammonium chloride (5 mL) and water (20 mL). The mixture was extracted with diethyl ether (30 mL), and the extract was dried, filtered and concentrated. Flash column chromatography on silica, eluting with 10% ethyl actetate-hexanes, gave ethyl(4,6-dichloropyrimidin-5-yl)amine (0.321 g, 1.67 mmol, 45%). LC-MS (LCT2) m/z 192, 194 [M+H$^+$], R$_t$ 6.07 min.

22B N$^5$-Ethyl-6-chloropyrimidine-4,5-diamine

A suspension of ethyl(4,6-dichloropyrimidin-5-yl)amine (0.31 g, 1.61 mmol) and concentrated aqueous ammonia (10 mL) in ethanol (3 mL) was heated to 100° C. in a sealed tube for 16 hours. The solution was cooled and evaporated to dryness. The residue was partitioned between ethyl acetate (20 mL) and dilute brine (10 mL). The organic layer was dried, filtered and concentrated to give N$^5$-ethyl-6-chloropyrimidine-4,5-diamine (0.214 g, 1.24 mmol, 77%) as a waxy solid. LC-MS (LCT2) m/z 173, 175 [M+H$^+$], R$_t$ 3.97.

22C. 7-Ethyl-6-chloro-7,9-dihydropurin-8-one

A solution of N$^5$-ethyl-6-chloropyrimidine-4,5-diamine (0.21 g, 1.22 mmol) and 1,1-carbonyldiimidazole (0.40 g, 2.44 mmol) in 1,4-dioxane (5 mL) was degassed, flushed with nitrogen and refluxed under nitrogen for 22 h. The solution was cooled and partitioned between ethyl acetate (15 mL), 1M hydrochloric acid (10 mL) and brine (5 mL). The organic layer was dried, filtered and concentrated to give 7-ethyl-6-chloro-7,9-dihydropurin-8-one (0.146 g, 0.735 mmol, 60%) as a yellow solid. LC-MS (LCT2) m/z 199, 201 [M+H$^+$], R$_t$ 4.62 min.

22D. 6-[4-Aminomethyl-4-(4-chlorophenyl)piperidin-1-yl]-7-ethyl-7,9-dihydro-purin-8-one A solution of 7-benzyl-6-chloro-7,9-dihydropurin-8-one (0.015 g, 0.075 mmol), C-[4-(4-chlorophenyl)piperidin-4-yl]methylamine bis hydrochloride (0.025 g, 0.085 mmol) and triethylamine (0.11 mL, 0.85 mmol) in n-butanol (0.5 mL) was heated at 150° C. in a microwave reactor for 3 h. The cooled mixture was partitioned between ethyl acetate (30 mL) and water (5 mL) and the organic layer was dried, filtered and concentrated. Purification on SCX-II acid resin, eluting with methanol then 1M ammonia/methanol, gave 6-[4-aminomethyl-4-(4-chlorophenyl)piperidin-1-yl]-7-ethyl-7,9-dihydropurin-8-one as a cream solid (0.016 g, 0.041 mmol, 56%). LC-MS (LCT2) m/z 387 [M+H$^+$], R$_t$ 14.18 min.

Example 23

C-[4-(4-Chlorobenzl)-1-(9H-purin-6-yl)piperidin-4-yl]methylamine

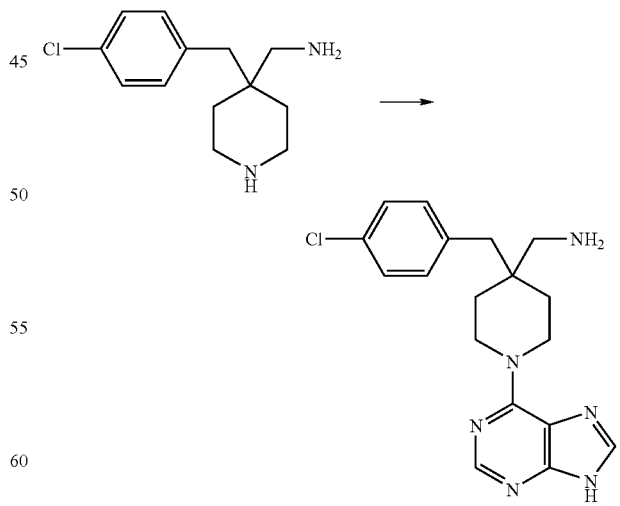

The title compound was prepared as described in Example 19 using 6-chloropurine in place of 4-chloro-7H-pyrrolo[2,3-d]pyrimidine. LC-MS (LCT2) m/z 357 [M+H$^+$], R$_t$ 4.07 min.

¹H NMR (MeOD) δ 1.57-1.62 (4H, m), 2.64 (2H, s), 2.82 (2H, s), 4.20-4.28 (2H, m), 4.39-4.47 (2H, m), 7.21-7.33 (4H, m), 7.98 (1H, s), 8.18 (2H, s)

Example 24

4-(4-Chlorophenyl)-1-(7H-pyrrolo[2,3-d]pyrimidin-4-yl)piperidine-4-carbonitrile

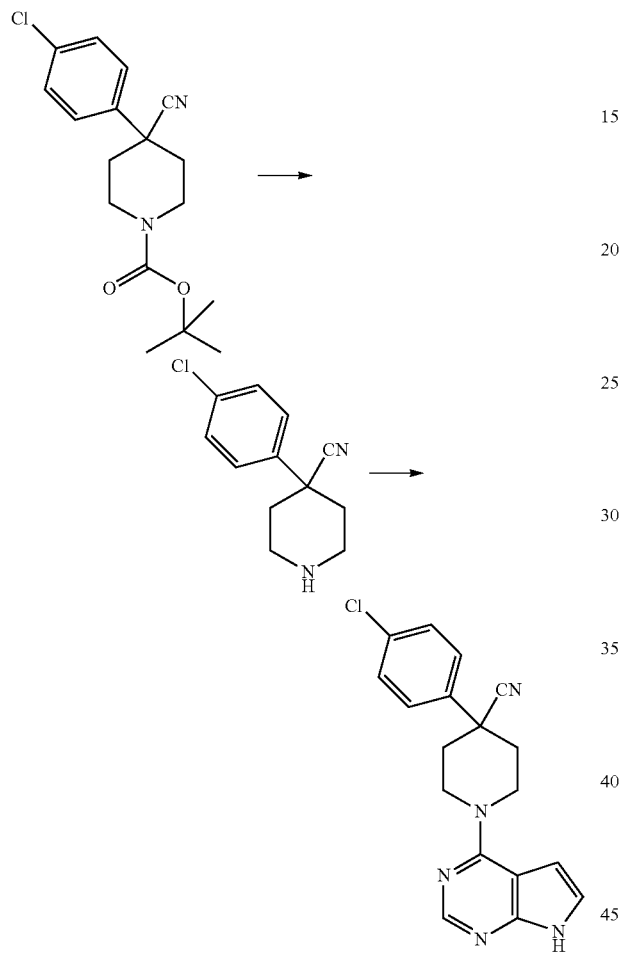

24A. 4-(4-Chlorophenyl)piperidine-4-carbonitrile

To a solution of 4-(4-chlorophenyl)-4-cyanopiperidine-1-carboxylic acid tert-butyl ester (1.000 g, 3.12 mmol) in methanol (5 ml) at rt was added 4M HCl in dioxane (15 ml). After stirring for 20 h the solution was concentrated to give the deprotected amine as the hydrochloride salt (0.785 g, 98%). LC-MS (LCT2) m/z 221 [M+H⁺], R$_t$ 12.84 min.

24B. 4-(4-Chlorophenyl)-1-(7H-pyrrolo[2,3-d]pyrimidin-4-yl)piperidine-4-carbonitrile A solution of 4-(4-chlorophenyl)piperidine-4-carbonitrile hydrochloride (0.055 g, 0.2155 mmol), 4-chloro-7H-pyrrolo[2,3-d]pyrimidine (0.033 g, 0.2155 mmol) and triethylamine (0.150 ml, 1.0775 mmol) in n-butanol (2.0 ml) was heated to 100° C. for 2 days. Concentration and trituration with methanol (3 ml) gave a white solid (0.058 g, 80%). LC-MS (LCT2) m/z 338 [M+H⁺], R$_t$ 16.17 min.

¹H NMR (DMSO) δ 2.03-2.15 (2H, m), 2.26-2.31 (2H, m), 3.36-3.41 (2H, m), 4.91 (2H, d, J=14 Hz), 6.66-6.68 (1H, m), 7.23-7.25 (1H, m), 7.50-7.63 (4H, m), 8.21 (1H, s)

Example 25

4-(4-Chlorophenyl)-1-(7H-pyrrolo[2,3-d]pyrimidin-4-yl)piperidin-4-ylamine

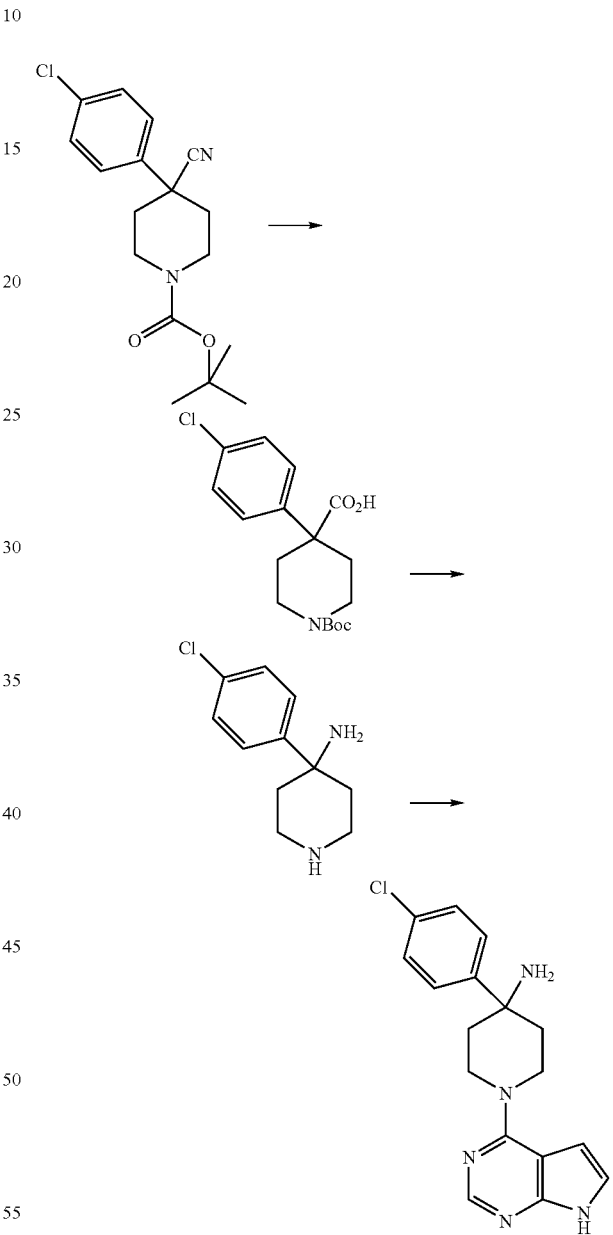

25A. 4-(4-Chlorophenyl)piperidine-1,4-dicarboxylic acid mono-tert-butyl ester A solution of 4-(4-chlorophenyl)-4-cyanopiperidine-1-carboxylic acid tert-butyl ester (0.683 g, 2.129 mmol) in 6M HCl (20 ml) was refluxed for 4 days. The solution was cooled, basified with NaOH and di-tert-butyl dicarbonate (0.558 g, 2.555 mmol) added. After stirring for 24 h the solution was extracted with diethyl ether (2×75 ml). The organic phases were combined, washed with brine (50 ml), dried over magnesium sulphate and concentrated. Purification by silica column chromatography (5% methanol in DCM) gave the acid as a white foam (0.339 g, 47%). LC-MS (LCT2) m/z 362 [M+Na$^+$], R$_t$ 8.17 min.

25B. 4-(4-Chlorophenyl)piperidin-4-yl amine

The title compound was prepared using the method described for Example 17C. $^1$H NMR (MeOD) δ 7.74-7.70 (m, 2H), 7.65-7.61 (m, 2H), 3.61-3.52 (m, 2H), 3.07-2.93 (m, 4H), 2.56-2.44 (m, 2H).

25C. 4-(4-Chlorophenyl)-1-(7H-pyrrolo[2,3-d]pyrimidin-4-yl)piperidin-4-ylamine A solution of 4-(4-chlorophenyl)piperidin-4-yl amine hydrochloride (0.030 g, 0.1058 mmol), 4-chloro-7H-pyrrolo [2,3-d]pyrimidine (0.016 g, 0.1058 mmol) and triethylamine (0.074 ml, 0.5289 mmol) in n-butanol (1.0 ml) was heated to 100° C. for 2 days. Concentration and purification by SCX-2 Isolute column (2 g), eluting with 1M NH$_3$/MeOH, followed by silica column chromatography (20% methanol in DCM) gave a white solid (0.026 g, 74%). LC-MS (LCT2) m/z 328 [M+H$^+$], R$_t$ 2.59 min.

$^1$H NMR (MeOD) δ 1.90-1.95 (2H, m), 2.18-2.34 (2H, m), 3.93-4.03 (2H, m), 4.20-4.29 (2H, m), 6.67 (1H, d, J=4 Hz), 7.15 (1H, d, J=4 Hz), 7.16-7.58 (4H, m), 8.16 (1H, s)

Example 26

C-[4-(3-Chlorophenyl)-1-(7H-pyrrolo[2,3-d]pyrimidin-4-yl)piperidin-4-yl]methylamine

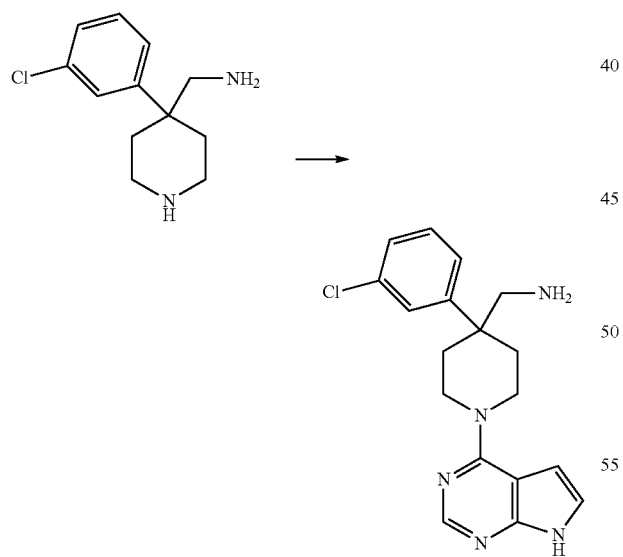

The title compound was prepared using the methods described in Example 14. LC-MS (LCT2) m/z 342 [M+H$^+$], R$_t$ 2.55 min.

$^1$H NMR (MeOD) δ 1.86-1.91 (2H, m), 2.30 (2H, d, J=14 Hz), 2.78 (2H, s), 3.43-3.50 (2H, m), 4.29-4.33 (2H, m), 6.59-6.60 (1H, m), 7.10-7.11 (1H, m), 7.27-7.29 (1H, m), 7.36-7.41 (2H, m), 7.47 (1H, s), 8.13 (1H, s)

Example 27

C-[4-(3-Chlorophenyl)-1-(9H-purin-6-yl)piperidin-4-yl]methylamine

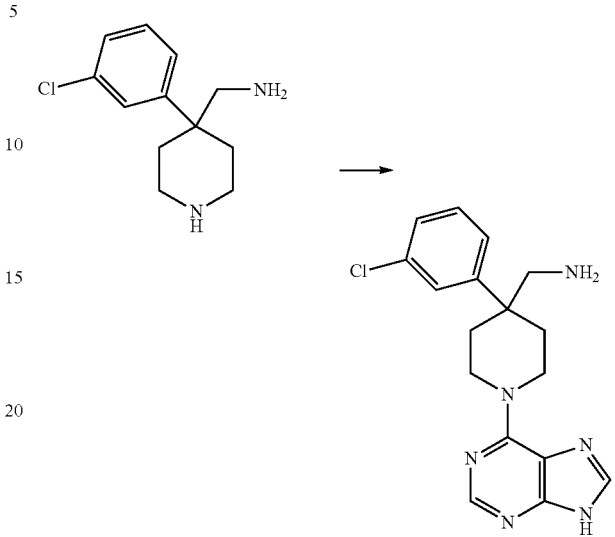

The title compound was prepared using the methods described in described in Examples 14 and 15. LC-MS (LCT2) m/z 343 [M+H$^+$], R$_t$ 13.60 min.

$^1$H NMR (DMSO) δ 1.81-1.90 (2H, m), 2.12-2.19 (2H, m), 2.70 (2H, s), 3.33 (2H, br s), 3.52 (2H, br s), 4.69 (2H, br s), 7.29-7.45 (4H, m), 8.10 (1H, s), 8.19 (1H, s)

Example 28

C-[4-(3,4-Dichlorophenyl)-1-(7H-pyrrolo[2,3-d]pyrimidin-4-yl)piperidin-4-yl]methylamine

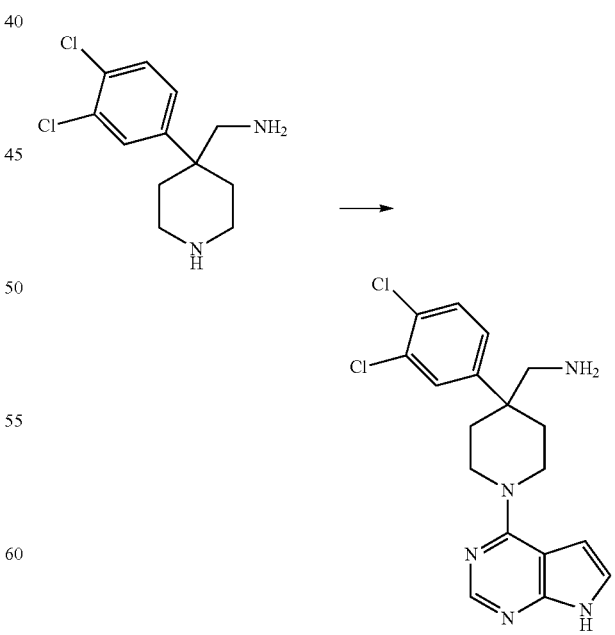

The title compound was prepared using the methods described in Example 14. LC-MS (LCT2) m/z 376 [M+H$^+$], R$_t$ 3.29 min.

¹H NMR (DMSO) δ 1.83-1.91 (2H, m), 2.16-2.25 (2H, m), 2.78 (2H, s), 3.39-3.47 (2H, m), 4.20-4.25 (2H, m), 6.58 (1H, d, J=3 Hz), 7.17 (1H, d, J=3 Hz), 7.41-7.45 (1H, m), 7.57-7.65 (2H, m), 8.13 (1H, s)

Example 29

C-[4-(3,4-Dichlorophenyl)-1-(9H-purin-6-yl)piperidin-4-yl]methylamine

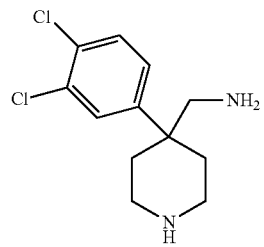

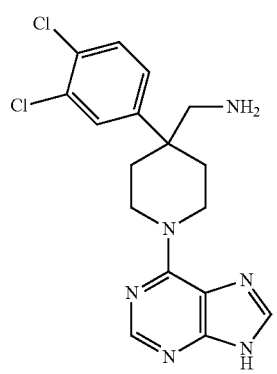

The title compound was prepared using the methods described in Examples 14 and 15. LC-MS (LCT2) m/z 377 [M+H⁺], $R_t$ 4.37 min.

¹H NMR (DMSO) δ 1.88-1.97 (2H, m), 2.23-2.28 (2H, m), 3.00 (2H, s), 3.66 (2H, br s), 7.73 (2H, br s), 7.46-7.50 (1H, m), 7.58-7.73 (2H, m), 8.09 (1H, s), 8.21 (1H, s)

Example 30

C-[1-(7H-pyrrolo[2,3-d]pyrimidin-4-yl)-4-trifluoromethoxyphenyl)piperidin-4-yl]methylamine

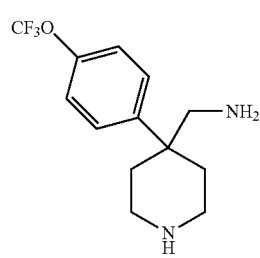

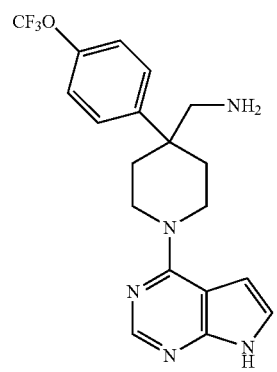

The title compound was prepared using the methods described in Example 14. LC-MS (LCT2) m/z 392 [M+H⁺], $R_t$ 3.25 min.

¹H NMR (MeOD) δ 1.17-1.21 (2H, m), 1.61-1.64 (2H, m), 2.08 (2H, s), 2.73-2.78 (2H, m), 3.59-3.63 (2H, m), 5.88 (1H, d, J=3.5 Hz), 6.38 (1H, d, J=3.5 Hz), 6.59-6.61 (2H, m), 6.83-6.84 (2H, m), 7.38 (1H, s)

Example 31

C-[1-(9H-Purin-6-yl)-4-(4-trifluoromethoxyphenyl)piperidin-4-yl]methylamine

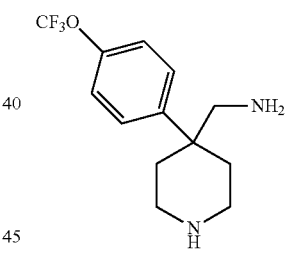

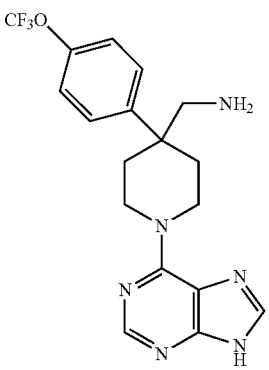

The title compound was prepared using the methods described in Examples 14 and 15. LC-MS (LCT2) m/z 393 [M+H⁺], $R_t$ 4.30 min.

¹H NMR (MeOD) δ 1.88-1.99 (2H, m), 2.35-2.41 (2H, m), 2.83 (2H, s), 3.62-3.71 (2H, m), 4.79-4.95 (2H, m), 7.34-7.57 (2H, m), 7.57-7.66 (2H, m), 7.99 (1H, s), 8.20 (1H, s)

Example 32

C-[1-(7H-Pyrrolo[2,3-d]pyrimidin-4-yl)-4-(4-trifluoromethylphenyl)piperidin-4-yl]methylamine

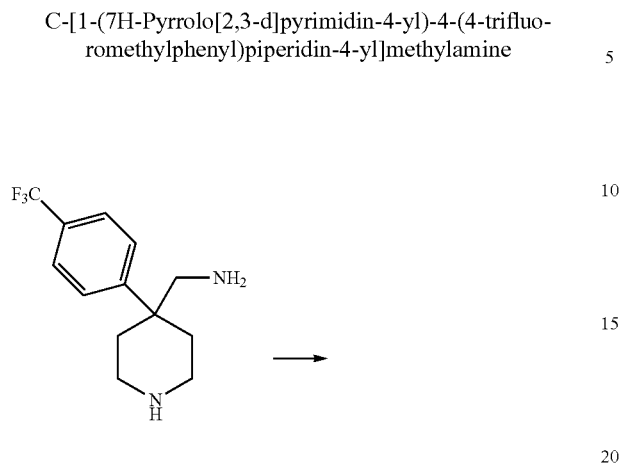

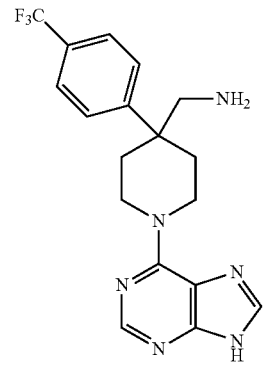

The title compound was prepared using the methods described in Example 14. LC-MS (LCT2) m/z 376 [M+H$^+$], R$_t$ 13.07 min.

$^1$H NMR (MeOD) δ 1.93-2.04 (2H, m), 2.40-2.46 (2H, m), 2.87 (2H, s), 3.47-3.58 (2H, m), 4.36-4.43 (2H, m), 6.65 (1H, d, J=3.5 Hz), 7.13 (1H, d, J=3.5 Hz), 7.68-7.77 (4H, m), 8.13 (1H, s)

Example 33

C-[1-(9H-Purin-6-yl)-4-(4-trifluoromethylphenyl)piperidin-4-yl]methylamine

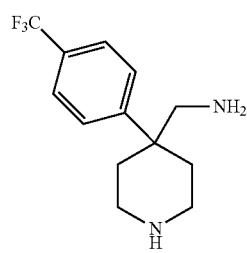

The title compound was prepared using the methods described in Examples 14 and 15. LC-MS (LCT2) m/z 377 [M+H$^+$], R$_t$ 4.19 min.

$^1$H NMR (MeOD) δ 1.92-2.03 (2H, m), 2.41-2.46 (2H, m), 2.87 (2H, s), 3.62-3.71 (2H, m) 4.79-4.87 (2H, m), 7.69-7.78 (4H, m), 8.02 (1H, s), 8.21 (1H, s)

Example 34

C-[1-(7H-Pyrrolo[2,3-d]pyrimidin-4-yl)-4-(3-trifluoromethylphenyl)piperidin-4-yl]methylamine

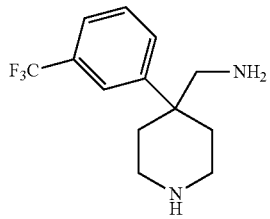

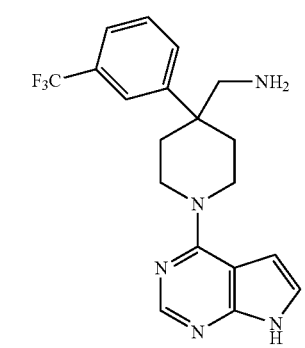

The title compound was prepared using the methods described in Example 14. LC-MS (LCT2) m/z 376 [M+H$^+$], R$_t$ 2.90 min.

¹H NMR (MeOD) δ 1.96-2.07 (2H, m), 2.40-2.45 (2H, m), 2.89 (2H, s), 3.49-3.59 (2H, m), 4.33-4.42 (2H, m), 6.66 (1H, d, J=3.5 Hz), 7.14 (1H, d, J=3.5 Hz), 7.61-7.81 (4H, m), 8.14 (1H, s)

Example 35

C-[1-(9H-Purin-6-yl)-4-(3-trifluoromethylphenyl)piperidin-4-yl]methylamine

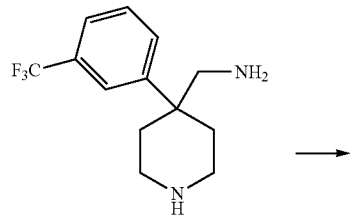

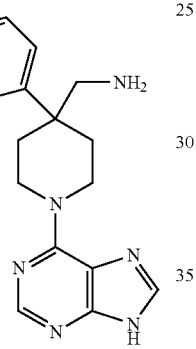

The title compound was prepared using the methods described in Examples 14 and 15. LC-MS (LCT2) m/z 377 [M+H⁺], R_t 3.97 min.

¹H NMR (MeOD) δ 1.94-2.05 (2H, m), 2.39-2.44 (2H, m), 2.89 (2H, s), 3.65-3.73 (2H, m), 4.80-5.10 (2H, m), 7.51-7.81 (4H, m), 8.02 (1H, s), 8.21 (1H, s)

Example 36

C-[4-(3,4-Difluorophenyl)-1-(7H-pyrrolo[2,3-d]pyrimidin-4-yl)piperidin-4-yl]methylamine

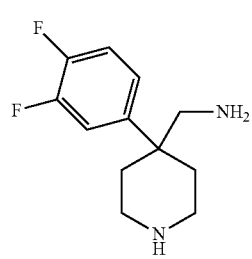

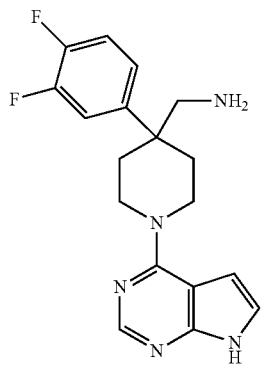

The title compound was prepared using the methods described in Example 14. LC-MS (LCT2) m/z 344 [M+H⁺], R_t 2.42 min.

¹H NMR (MeOD) δ 1.88-1.99 (2H, m), 2.32-2.37 (2H, m), 2.84 (2H, s), 3.45-3.57 (2H, m), 4.34-4.41 (2H, m), 6.64 (1H, d, J=3.5 Hz), 7.13 (1H, d, J=3.5 Hz), 7.31-7.47 (3H, m), 8.14 (1H, s)

Example 37

C-[4-(3,4-Difluorophenyl)-1-(9H-purin-6-yl)piperidin-4-yl]methylamine

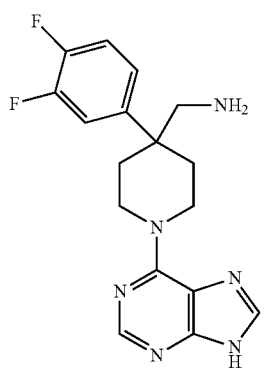

The title compound was prepared using the methods described in Examples 14 and 15. LC-MS (LCT2) m/z 345 [M+H⁺], R_t 3.42 min.

¹H NMR (MeOD) δ 1.87-1.98 (2H, m), 2.31-2.36 (2H, m), 2.82 (2H, s), 3.64-3.72 (2H, m), 4.79-4.95 (2H, m), 7.29-7.48 (3H, m), 8.02 (1H, s), 8.21 (1H, s)

Example 38

C-[4-(4-Methoxyphenyl)-1-(7H-pyrrolo[2,3-d]pyrimidin-4-yl)piperidin-4-yl]methylamine

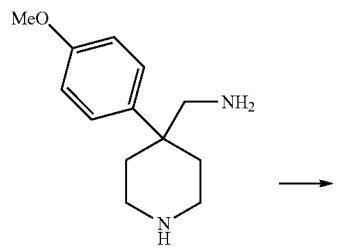

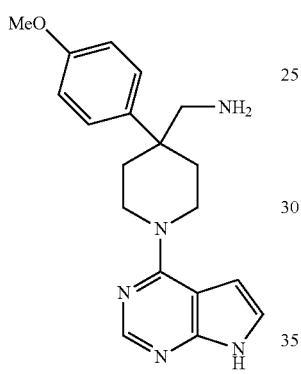

The title compound was prepared using the methods described in Example 14. LC-MS (LCT2) m/z 338 [M+H⁺], R_t 2.37 min.

¹H NMR (MeOD) δ 1.82-1.93 (2H, m), 2.36-2.42 (2H, m), 2.81 (2H, s), 3.41-3.51 (2H, m), 3.83 (3H, s), 4.38-4.45 (2H, m), 6.63 (1H, d, J=3.5 Hz), 7.00-7.03 (2H, m), 7.12 (1H, d, J=3.5 Hz), 7.39-7.42 (2H, m), 8.13 (1H, s)

Example 39

C-[4-(4-Methoxyphenyl)-1-(9H-purin-6-yl)Piperidin-4-yl]methylamine

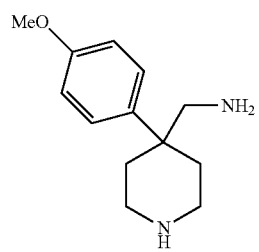

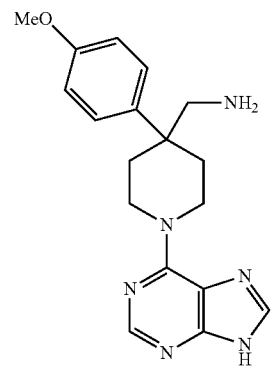

The title compound was prepared using the methods described in Examples 14 and 15. LC-MS (LCT2) m/z 339 [M+H⁺], R_t 3.20 min.

¹H NMR (MeOD) δ 1.81-1.91 (2H, m), 2.37-2.42 (2H, m), 2.77 (2H, s), 3.53-3.63 (2H, m), 3.84 (3H, s), 4.80-5.10 (2H, m), 7.02 (2H, d, J=9 Hz), 7.41 (2H, d, J=9 Hz), 8.01 (1H, s), 8.20 (1H, s)

Example 40

C-[4-(4-Benzyloxyphenyl)-1-(7H-pyrrolo[2,3-d]pyrimidin-4-yl)piperidin-4-yl]methylamine

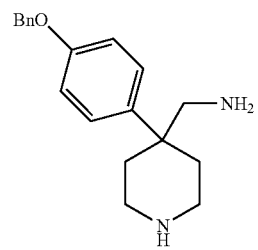

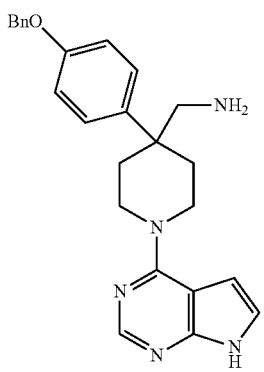

The title compound was prepared using the methods described in Example 14. LC-MS (LCT2) m/z 414 [M+H⁺], R_t 3.87 min.

¹H NMR (MeOD) δ 1.84-1.89 (2H, m), 2.36-2.38 (2H, m), 2.78 (2H, s), 3.44-3.49 (2H, m), 4.37-4.40 (2H, m), 5.11 (2H, s), 6.62-6.64 (1H, m), 7.07-7.13 (3H, m), 7.30-7.46 (7H, m), 8.12 (1H, s)

Example 41

C-[4-(4-Benzyloxyphenyl)-1-(9H-purin-6-yl)piperidin-4-yl]methylamine

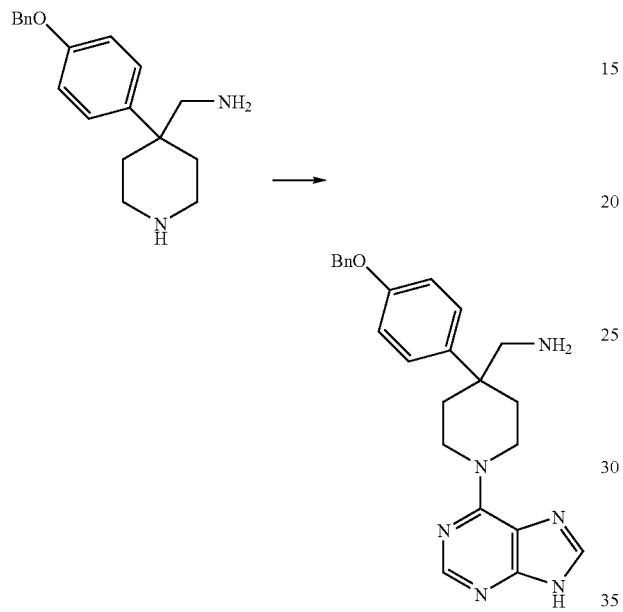

The title compound was prepared using the methods described in Examples 14 and 15. LC-MS (LCT2) m/z 415 [M+H⁺], R_t 4.85 min.
¹H NMR (MeOD) δ 1.81-1.91 (2H, m), 2.37-2.42 (2H, m), 2.73 (2H, s), 3.54-3.63 (2H, m), 4.80-5.10 (2H, m), 5.13 (2H, s), 7.09 (2H, d, J=9 Hz), 7.32-7.48 (7H, m), 8.01 (1H, s), 8.20 (1H, s)

Example 42

[4-(4-Chloro-phenyl)-1-(7H-pyrrolo[2,3-d]pyrimidin-4-yl)-piperidin-4-ylmethyl]-methyl-amine

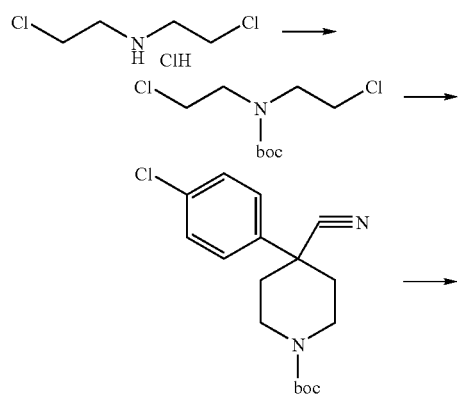

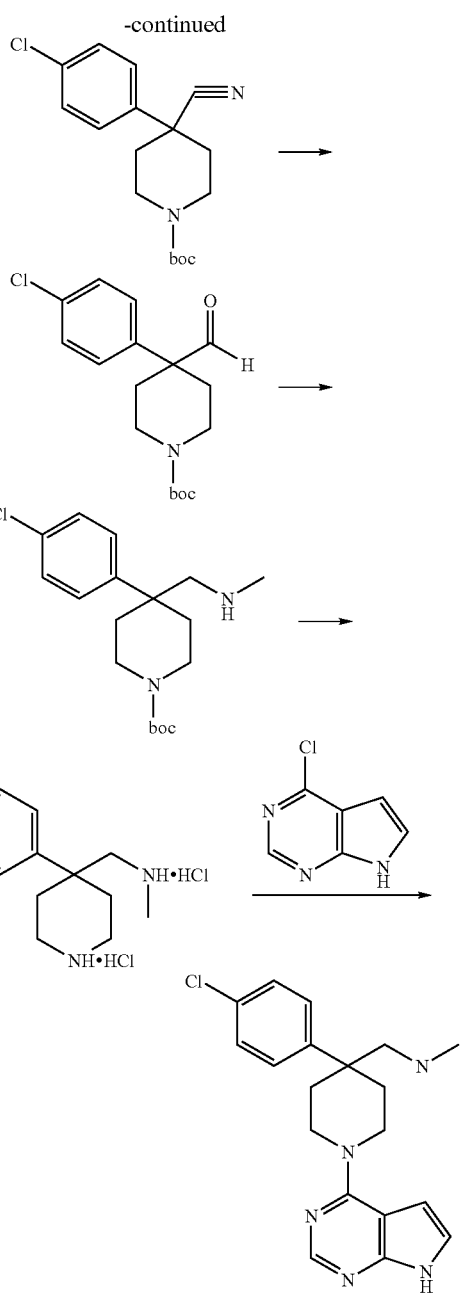

42A. Bis-(2-chloro-ethyl)-carbamic acid tert-butyl ester

A suspension of bis-(2-chloro-ethyl)-amine hydrochloride (5 g, 0.028 mol) in dichloromethane (42 ml) was rapidly stirred with 10% aqueous sodium hydroxide (28 ml) in an ice bath, to which di-tert-butyl dicarbonate (6.11 g, 0.028 mol) in dichloromethane (28 ml) was added. After stirring at room temperature for 18.5 hours, dichloromethane (30 ml) was added to the reaction mixture and the two phases were separated. The aqueous phase was further extracted with dichloromethane (30 ml). The combined organic layers were dried (Mg₂SO₄), filtered and concentrated to give bis-(2-chloroethyl)-carbamic acid tert-butyl ester (6.74 g, 0.028 mol, 100%). ¹H NMR (250 MHz, CDCl₃): 1.48 (9H, s), 3.62-3.68 (8H, m).

42B. 4-(4-Chlorophenyl)-4-cyano-piperidine-1-carboxylic acid tert-butyl ester Sodium hydride (60% dispersion in mineral oil, 2.9 g, 72.3 mmol) was added in small portions, over a period of 1 hour, to a solution of bis-(2-chloro-ethyl)-carbamic acid tert-butyl ester (6.74 g, 28 mmol) and 4-chlorobenzyl cyanide (3.8 g, 25 mmol) in anhydrous dimethylformamide (25 ml). The reaction mixture was heated at 65° C. for 1 hour and then stirred at room temperature for 89 hours. After this period, the reaction mixture was poured into ice/water (60 ml) and extracted with ethyl acetate (2×100 ml). The combined organic layers were washed with water and brine, dried, filtered and concentrated. Flash column chromatography on silica, eluting with hexane/dichloromethane/ethyl acetate (8:1:1), gave 4-(4-chlorophenyl)-4-cyano-piperidine-1-carboxylic acid tert-butyl ester (5.6 g, 17.5 mmol, 70%) as a white solid. LC-MS (LCT) m/z 320 [M+], $R_t$ 7.71 min.

42C. 4-(4-Chlorophenyl)-4-formyl-piperidine-1-carboxylic acid tert-butyl ester A solution of 4-(4-chlorophenyl)-4-cyano-piperidine-1-carboxylic acid tert-butyl ester (2.0 g, 6.2 mmol,) in dry toluene (30 ml) at −78° C., under nitrogen, was treated with a solution of DIBAL-H (10 ml, 10 mmol, 1M solution in toluene). The reaction was maintained at −78° C. for 3 hours, at which time it was quenched by slow addition a saturated solution of ammonium chloride (7.3 ml) and allowed to warm to room temperature. The reaction mixture was poured into water (50 ml) and extracted with ethyl acetate (2×100 ml). The organic layer was separated, dried ($Mg_2SO_4$), filtered and concentrated. Flash column chromatography on silica, eluting with 20% ethyl acetate in hexane, gave 4-(4-chlorophenyl)-4-formyl-piperidine-1-carboxylic acid tert-butyl ester (453 mg, 1.4 mmol, 22%) as a white solid. LC-MS (LCT2) m/z 346 [M+Na+], $R_t$ 8.49 min.

42D. 4-(4-Chloro-phenyl)-4-methylaminomethyl-piperidine-1-carboxylic acid tert-butyl ester A mixture of methylamine in ethanol (18 ml, 33% in ethanol) and 4-(4-chlorophenyl)-4-formyl-piperidine-1-carboxylic acid tert-butyl ester (206 mg, 0.62 mmol) was stirred at room temperature overnight. The solvents were concentrated. The crude material was redissolved in methanol (18 ml) followed by addition of sodium borohydride (49 mg, 1.29 mmol). After stirring for 40 minutes at room temperature, the mixture was partitioned between ethyl acetate (100 ml) and a saturated aqueous solution of sodium hydrogen carbonate (100 ml). After separation of the two phases the aqueous phase was re-extracted with ethyl acetate (100 ml). The combined organic layers were dried ($Na_2SO_4$), filtered and concentrated. Flash column chromatography on silica, eluting with 10% methanol in dichloromethane gave 4-(4-chloro-phenyl)-4-methylaminomethyl-piperidine-1-carboxylic acid tert-butyl ester (142 mg, 0.42 mmol, 68%). GC-MS m/z 239 [(M-Boc)+], $R_t$ 5.18 min. $^1$H NMR (250 MHz, $CDCl_3$): 1.43 (9H, s), 1.80-1.88 (2, m), 2.15-2.24 (2, m), 2.31 (3H, s), 2.81 (2H, s), 2.98-3.09 (2H, m), 3.72-3.78 (2H, m), 7.32 (2H, d, 9 Hz), 7.38 (2H, d, 9 Hz).

42E. [4-(4-Chlorophenyl)-piperidin-4-ylmethyl]-methylamine bis-hydrochloride A 4M solution of hydrochloric acid in dioxane (10 ml) was added dropwise to a solution of 4-(4-chlorophenyl)-4-methylaminomethyl-piperidine-1-carboxylic acid tert-butyl ester (142 mg, 0.42 mmol) in methanol (10 ml). The reaction was stirred overnight at room temperature. After this period of time, the solvents were concentrated to give [4-(4-chlorophenyl)-piperidin-4-ylmethyl]-methylamine bis-hydrochloride (132 mg, 0.42 mmol, 100%). This compound was used in the subsequent step without further purification. LC-MS (LCT2) m/z 239 [M+H+], $R_t$ 0.53 min.

42F. [4-(4-Chlorophenyl)-1-(7H-pyrrolo[2,3-d]pyrimidin-4-yl)-piperidin-4-ylmethyl]-methylamine A solution of 4-chloro-7H-pyrrolo[2,3-d]pyrimidine (15.5 mg, 0.1 mmol), [4-(4-chlorophenyl)-piperidin-4-ylmethyl]-methylamine bis-hydrochloride (34 mg, 0.11 mmol) and triethylamine (150 μL, 0.7 mmol) in n-butanol (1 ml) was heated at 100° C. in a microwave reactor for 60 minutes. After cooling the reaction the solvents were concentrated. Purification on SCX-II acid resin, eluting with methanol then 2M ammonia/methanol, followed by further purification by flash column chromatography on silica, eluting with 15% methanol in dichloromethane, gave [4-(4-chlorophenyl)-1-(7H-pyrrolo[2,3-d]pyrimidin-4-yl)-piperidin-4-ylmethyl]-methylamine (12.3 mg, 0.034 mmol, 34%). LC-MS (LCT2) m/z 356 [M+H+], $R_t$ 2.64 min.

$^1$H NMR (MeOD) δ 1.94-2.05 (2H, m), 2.28 (3H, s), 2.36-2.41 (2H, m), 2.80 (2H, s), 3.50-3.61 (2H, m), 4.30-4.39 (2H, m), 6.65 (1H, d, J=4 Hz), 7.14 (1H, d, J=4 Hz), 7.42-7.52 (4H, m), 8.13 (1H, s)

Example 43

[4-(4-Chlorophenyl)-1-(7H-pyrrolo[2,3-d]pyrimidin-4-yl)-piperidin-4-ylmethyl]-isopropylamine

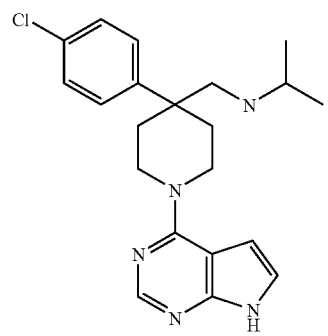 [SMILES: CC(C)NCC1(c2ccc(Cl)cc2)CCN(c2ncnc3[nH]ccc23)CC1]

The title compound was prepared by the method described in Example 42, but replacing methylamine with isopropylamine in step 44D. LC-MS (LCT2) m/z 384 [M+H+], $R_t$ 2.80 min.

$^1$H NMR (MeOD) δ 0.97 (6H, d, J=8 Hz), 1.96-2.07 (2H, m), 2.35-2.41 (2H, m), 2.61 (1H, septet, J=8 Hz), 2.83 (2H, s), 3.52-3.62 (2H, s), 4.31-4.37 (2H, m), 6.65 (1H, d, J=4 Hz), 7.14 (1H, d, J=4 Hz), 7.43 (2H, d, J=8 Hz), 7.52 (2H, d, J=8 Hz), 8.13 (1H, s)

Example 44

[4-(4-Chlorobenzyl)-1-(7H-pyrrolo[2,3-d]pyrimidin-4-yl)-piperidin-4-yl]-dimethylamine

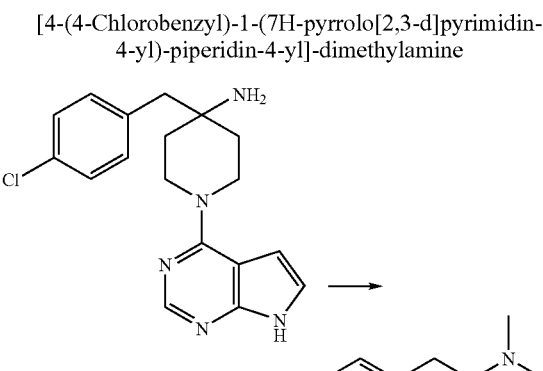

44A. [4-(4-Chlorobenzyl)-1-(7H-pyrrolo[2,3-d]pyrimidin-4-yl)-piperidin-4-yl]-dimethylamine A mixture of 4-(4-chlorobenzyl)-1-(7H-pyrrolo[2,3-d]pyrimidin-4-yl)-piperidin-4-ylamine from Example 17 (20 mg, 0.06 mmol), formic acid (0.16 ml, 96%) and formaldehyde (4 µl, 0.05 mmol, 37% in water) was heated at 100° C. for 48 hours. After cooling the reaction mixture to room temperature, the mixture was basified to pH 10 by addition of a 1M aqueous solution of sodium hydroxide, followed by extraction with ethyl acetate (20 ml). The organic layer was dried ($Mg_2SO_4$), filtered and concentrated. Flash column chromatography on silica, eluting with 15% methanol in dichloromethane gave [4-(4-chlorobenzyl)-1-(7H-pyrrolo[2,3-d]pyrimidin-4-yl)-piperidin-4-yl]-dimethylamine (3.8 mg, 0.01 mmol, 17%). LC-MS (LCT2) m/z 370 [M+H$^+$], R$_t$ 2.62 min.

$^1$H NMR (MeOD) δ 1.42-1.53 (2H, m), 2.02-2.18 (2H, m), 2.43 (6H, s), 2.81 (2H, s), 3.51-3.61 (2H, m), 4.30-4.35 (2H, m), 6.60 (1H, d, J=4 Hz), 7.09 (1H, d, J=4 Hz), 7.17-7.28 (4H, m), 8.06 (1H, s).

Example 45

C-[4-(3,4-Dichlorobenzyl)-1-(7H-pyrrolo[2,3-d]pyrimidin-4-yl)piperidin-4-yl]methylamine

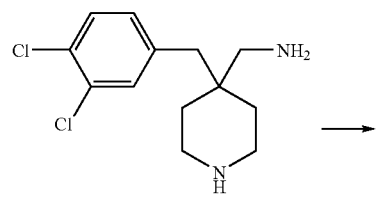

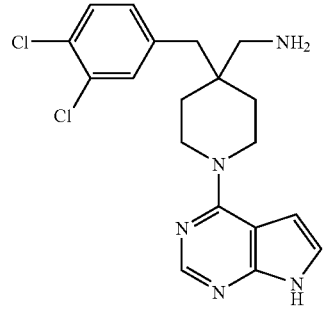

The title compound was prepared using the methods described in Example 19. LC-MS (LCT2) m/z 390 [M+H$^+$], R$_t$ 3.37 min.

$^1$H NMR (MeOD) δ 1.48-1.64 (4H, m), 2.63 (2H, s), 2.81 (2H, s), 3.85-4.16 (4H, m), 6.64 (1H, d, J=3.5 Hz), 7.12-7.21 (2H, m), 7.44-7.47 (2H, m), 8.13 (1H, s)

Example 46

C-[4-(3, 4-Dichlorobenzyl)-1-(9H-purin-6-yl)piperidin-4-yl]methylamine

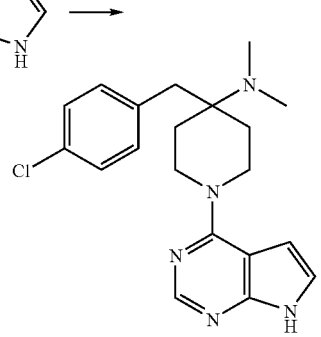

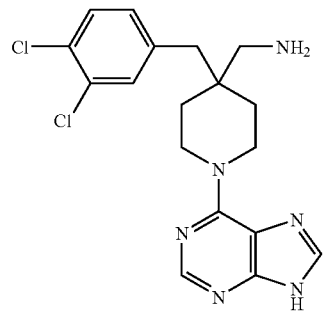

The title compound was prepared using the methods described in Examples 19 and 23. LC-MS (LCT2) m/z 391 [M+H$^+$], R$_t$ 4.42 min.

$^1$H NMR (MeOD) δ 1.40-1.53 (4H, m), 2.51 (2H, s), 2.69 (2H, s), 4.00-4.11 (2H, m), 4.30-4.40 (2H, m), 7.03-7.08 (1H, m), 7.30-7.35 (2H, m), 7.88 (1H, s), 8.08 (1H, s)

Example 47

C-[1-(7H-Pyrrolo[2,3-d]pyrimidin-4-yl)-4-(4-trifluoromethoxybenzyl)piperidin-4-yl]methylamine

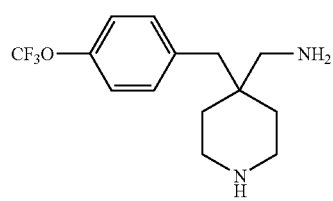

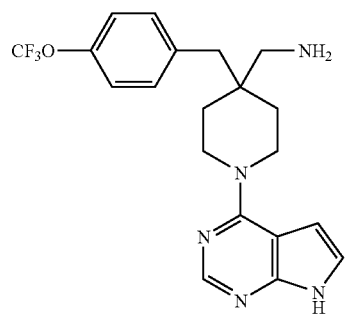

The title compound was prepared using the methods described in Example 19. LC-MS (LCT2) m/z 406 [M+H+], R$_t$ 3.39 min.

$^1$H NMR (MeOD) δ 1.61-1.65 (4H, m), 2.63 (2H, s), 2.86 (2H, s), 3.89-4.15 (4H, m), 6.64 (1H, d, J=4 Hz), 7.13 (1H, d, J=4 Hz), 7.21-7.37 (4H, m), 8.13 (1H, s)

Example 48

C-[1-(9H-Purin-6-yl)-4-(4-trifluoromethoxybenzyl)piperidin-4-yl]methylamine

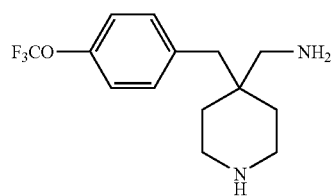

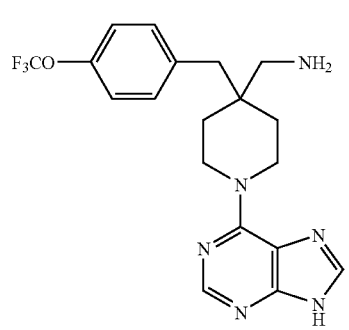

The title compound was prepared using the methods described in Examples 19 and 23. LC-MS (LCT2) m/z 407 [M+H+], R$_t$ 4.42 min.

$^1$H NMR (MeOD) δ 1.54-1.63 (4H, m), 2.64 (2H, s), 2.86 (2H, s), 4.18-4.28 (2H, m), 4.40-4.50 (2H, m), 7.20-7.36 (4H, m), 8.01 (1H, s), 8.21 (1H, s)

Example 49

4-(3,4-Dichlorobenzl)-1-(7H-pyrrolo[2,3-d]pyrimidin-4-yl)piperidin-4-ylamine

The title compound was prepared using the methods described in Example 17. LC-MS (LCT) m/z 376 [M+H+], R$_t$ 3.30 min.

$^1$H NMR (MeOD) δ 1.54-1.61 (2H, m), 1.72-1.83 (2H, m), 2.79 (2H, s), 3.73-3.84 (2H, m), 4.28-4.37 (2H, m), 6.64 (1H, d, J=3.5 Hz), 7.13 (1H, d, J=3.5 Hz), 7.18-7.22 (1H, m), 7.46-7.54 (2H, m), 8.14 (1H, s)

Example 50

4-(3,4-Dichlorobenzyl)-1-(9H-purin-6-yl)piperidin-4-yl amine

The title compound was prepared using the methods described in Examples 17 and 18. LC-MS (LCT) m/z 377 [M+H+], R$_t$ 4.19 min.

¹H NMR (MeOD) δ 1.37-1.46 (2H, m), 1.58-1.69 (2H, m), 2.67 (2H, s), 3.76-3.85 (2H, m), 4.65-4.75 (2H, m), 7.05-7.09 (1H, m), 7.32-7.36 (2H, m), 7.88 (1H, s), 8.08 (1H, s)

Example 51

1-(7H-pyrrolo[2,3-d]pyrimidin-4-yl)-4-(4-trifluoromethoxybenzyl)piperidin-4-ylamine

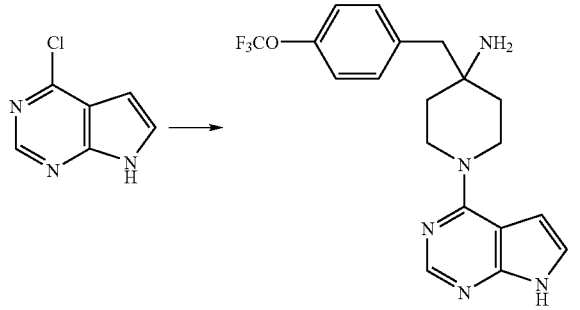 [SMILES: Clc1ncnc2[nH]ccc12 ; NC1(Cc2ccc(OC(F)(F)F)cc2)CCN(c2ncnc3[nH]ccc23)CC1]

The title compound was prepared using the methods described in Example 17. LC-MS (LCT) m/z 392 [M+H⁺], R_t 3.34 min.

¹H NMR (MeOD) δ 1.56-1.61 (2H, m), 1.74-1.85 (2H, m), 2.85 (2H, s), 3.76-3.87 (2H, m), 4.26-4.35 (2H, m), 6.64 (1H, d, J=3.5 Hz), 7.13 (1H, d, J=3.5 Hz), 7.23-7.39 (4H, m), 8.14 (1H, s)

Example 52

1-(9H-Purin-6-yl)-4-(4-trifluoromethoxybenzyl)piperidin-4-ylamine

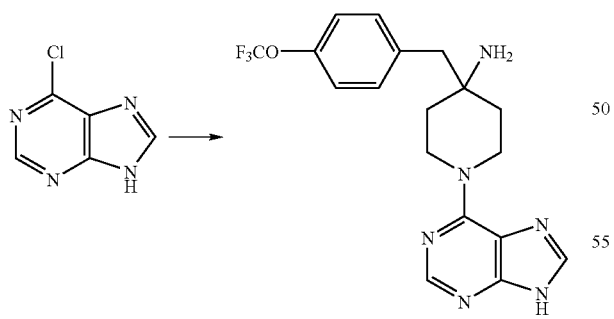

The title compound was prepared using the methods described in Examples 17 and 18. LC-MS (LCT) m/z 393 [M+H⁺], R_t 4.20 min.

¹H NMR (MeOD) δ 1.55-1.60 (2H, m), 1.72-1.92 (2H, m), 2.85 (2H, s), 3.92-4.02 (2H, m), 4.76-4.88 (2H, m), 7.23-7.38 (4H, m), 8.01 (1H, s), 8.21 (1H, s)

Example 53

1-(7H-pyrrolo[2,3-d]pyrimidin-4-yl)-4-(3-chlorobenzyl)piperidin-4-ylamine

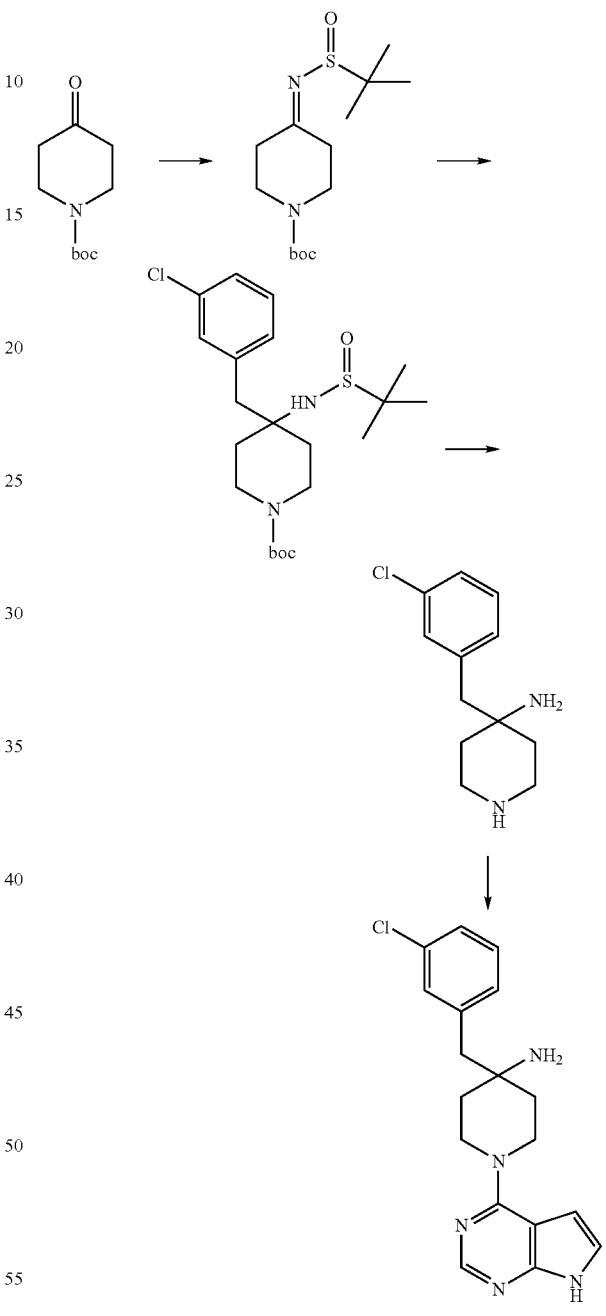

53A. 4-(3-chlorobenzyl)-4-(2-methylpropane-2-sulphinylamino)-piperidine-1-carboxylic acid tert-butyl ester A solution of N-BOC-piperidone (0.205 g, 1.03 mmol), t-butylsulphinamide (0.13 g, 1.07 mmol) and titanium tetraethoxide (0.42 ml, 2.0 mmol) in dry THF (5 ml) was refluxed under nitrogen for 5 h. The cooled solution was diluted with brine (10 ml) and ethyl acetate (10 ml). The suspension was shaken, the filtered through Celite, washing with ethyl acetate (10 ml). The two-phase filtrate was separated and the organic layer was dried (Na$_2$SO$_4$) filtered and concentrated to give the crude sulphinimine (0.293 g). The crude sulphinimine (0.293 g) was suspended in dry THF (2 ml) and stirred at room temperature under nitrogen. A solution of 3-chlorobenzyl magnesium bromide (ca. 4 mmol) (freshly prepared as a solution in diethyl ether from 3-chlorobenzylbromide and magnesium turnings) was added to give an orange solution. After 3 hours, the mixture was diluted with saturated aqueous ammonium chloride (20 ml) and extracted with ethyl acetate (20 ml). The extract was washed with water (20 ml), brine (10 ml), dried (Na$_2$SO$_4$), filtered and concentrated. Flash column chromatography, eluting with 50% ethyl acetate-hexanes, gave 4-(3-chlorobenzyl)-4-(2-methylpropane-2-sulphinylamino)-piperidine-1-carboxylic acid tert-butyl ester as a straw-coloured foam (0.139 g, 0.324 mmol, 31%). LC-MS (LCT) m/z 451, 453 [M+Na$^+$], R$_t$ 8.22 min.

53B. 1-(7H-pyrrolo[2,3-d]pyrimidin-4-yl)-4-(3-chlorobenzyl)piperidin-4-ylamine A solution of 4-(3-chlorobenzyl)-4-(2-methylpropane-2-sulpinylamino)-piperidine-1-carboxylic acid tert-butyl ester (0.134 g, 0.312 mmol) and 4M HCl in dioxane (2 ml, 8 mmol) in dry methanol (2 ml) was stirred at room temperature for 5 hours. The mixture was concentrated then applied to an acidic resin cartridge (SCX-II, 5 g) and eluted with methanol and 2M ammonia-methanol. The amine-containing fractions were further purified by application to a basic resin cartridge (NH2, 2 g), eluting with methanol, to give the crude amine as a yellow oil (0.063 g). A solution of the crude amine (0.063 g), triethyl amine (0.3 ml, 2 mmol) and 4-4-chloro-7H-pyrrolo[2,3-d]pyrimidine (0.039 g, 0.25 mmol) in dry 1-butanol (1 ml) was refluxed under nitrogen for 16 hours. The solution was concentrated and applied to an acidic resin column (SCX, 2 g) then eluted with methanol and 1M ammonia-methanol. The basic fractions were combined and concentrated. Flash silica column chromatography, eluting with 10% methanol-dichloromethane, gave the product as a yellow oil. Trituration and washing with diethyl ether gave a cream solid (0.031 g, 0.0907 mmol, 29%). LC-MS (LCT) m/z 344, 342 [M+H$^+$], R$_t$ 2.90 min.

$^1$H NMR (MeOD) δ 1.45 (2H, d, J=13 Hz), 1.63-1.68 (2H, m), 2.69 (2H, s), 3.65-3.69 (2H, m), 4.19 (2H, d, J=14 Hz), 6.52 (1H, d, 4 Hz), 7.01 (1H, d, J=4 Hz), 7.08 (1H, d, J=7 Hz), 7.15-7.21 (3H, m), 8.01 (1H, s)

Example 54

4-(4-Chlorobenzyl)-1-(1H-pyrrolo[2,3-b]pyridin-4-yl)-piperidin-4-ylamine

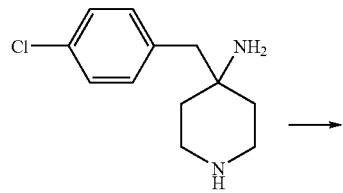

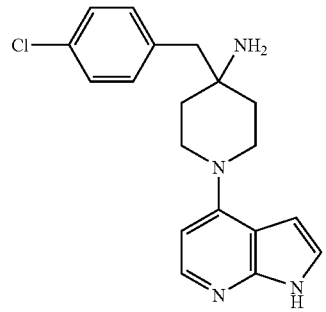

The title compound was prepared in a similar manner to Examples 14 and 17, using 4-fluoro-1-triisopropylsilanyl-1H-pyrrolo[2,3-b]pyridine (*Org Lett* 2003, 5, 5023-5026) in place of 4-chloro-7H-pyrrolo[2,3-d]pyrimidine, with NMP as solvent and microwave heating at 160° C. LC-MS (LCT2) m/z 341, 343 [M+H$^+$], R$_t$ 2.39 min.

$^1$H NMR (CDCl$_3$) δ 0.98-1.47 (2H, m), 1.76-1.80 (2H, m), 2.65 (2H, s), 3.43-3.48 (2H, m), 3.78-3.81 (2H, m), 6.37 (1H, d, J=6 Hz), 6.46 (1H, d, J=4 Hz), 7.05-7.07 (3H, m), 7.23-7.25 (2H, m), 7.86 (1H, d, J=6 Hz)

Example 55

4-(2-Chlorobenzyl)-1-(7H-pyrrolo[2,3-d]pyrimidin-4-yl)piperidin-4-ylamine

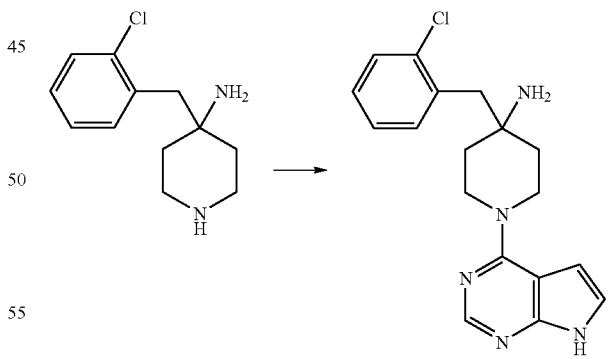

The title compound was prepared as described in Example 53. LC-MS (LCT2) m/z 342 [M+H$^+$], R$_t$ 2.86 min.

$^1$H NMR (MeOD) δ 1.61-1.63 (2H, m), 1.82-1.87 (2H, m), 3.01 (2H, s), 3.68-3.73 (2H, m), 4.37-4.40 (2H, m), 6.60-6.62 (1H, m), 7.11-7.12 (1H, m), 7.23-7.29 (2H, m), 7.37-7.43 (2H, m), 8.11 (1H, s)

Example 56

4-(4-tert-Butylbenzyl)-1-(7H-pyrrolo[2,3-d]pyrimidin-4-yl)piperidin-4-yl amine

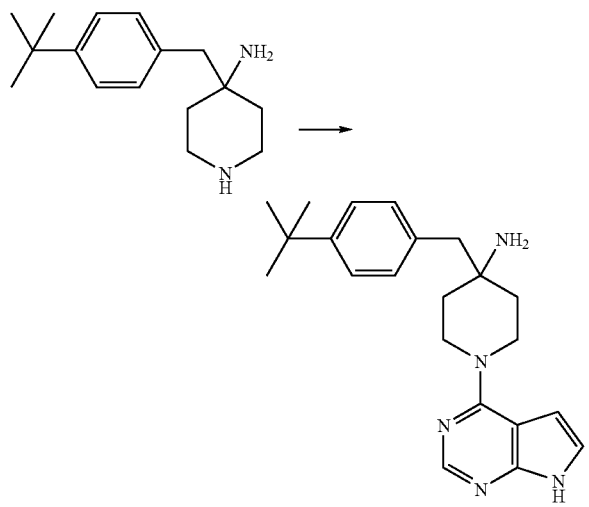

The title compound was prepared as described in Example 53. LC-MS (LCT2) m/z 364 [M+H$^+$], R$_t$ 4.24 min.

$^1$H NMR (MeOD) δ 1.32 (9H, s), 1.55-1.58 (2H, m), 1.75-1.81 (2H, m), 2.78 (2H, s), 3.79-3.85 (2H, m), 4.24-4.29 (2H, m), 6.63 (1H, d, J=4 Hz), 7.13 (1H, d, J=4 Hz), 7.37 (2H, d, J=8 Hz), 7.37 (2H, d, J=8 Hz), 8.12 (1H, s)

Example 57

4-(3-Methoxybenzyl)-1-(7H-pyrrolo[2,3-d]pyrimidin-4-yl)piperidin-4-ylamine

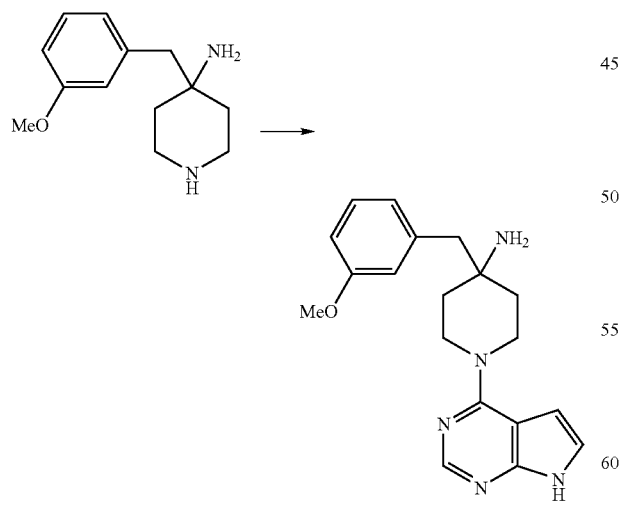

The title compound was prepared as described in Example 53. LC-MS (LCT2) m/z 338 [M+H$^+$], R$_t$ 2.61 min.

$^1$H NMR (MeOD) δ 1.53-1.55 (2H, m), 1.72-1.77 (2H, m), 2.73 (2H, s), 3.75-3.79 (2H, m), 3.78 (3H, s), 4.23-4.26 (2H, m), 6.58-6.59 (1H, m), 6.80-6.82 (3H, m), 7.09-7.10 (1H, m), 7.20-7.21 (1H, m), 8.12 (1H, s)

Example 58

4-(3-Trifluoromethoxybenzyl)-1-(7H-pyrrolo [2,3-d] pyrimidin-4-yl)piperidin-4-ylamine

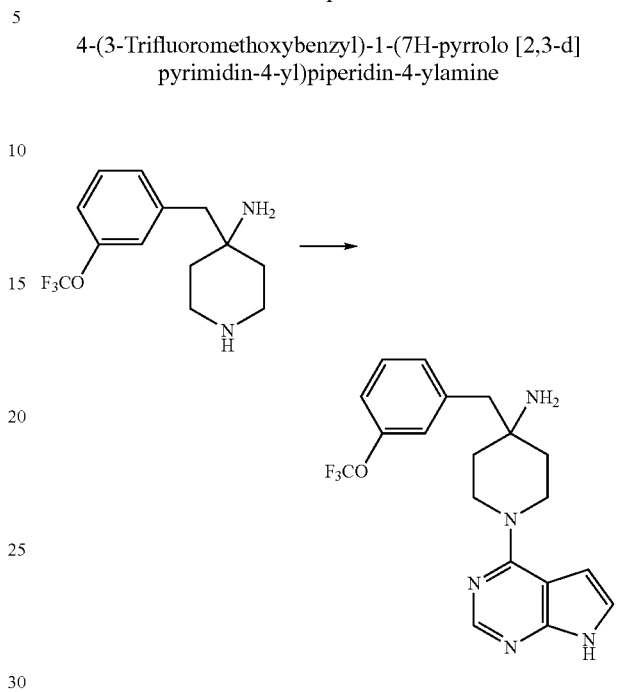

The title compound was prepared as described in Example 53. LC-MS (LCT2) m/z 392 [M+H$^+$], R$_t$ 3.47 min.

$^1$H NMR (MeOD) δ 1.40-1.43 (2H, m), 1.59-1.65 (2H, m), 2.68 (2H, s), 3.60-3.64 (2H, m), 4.16-4.18 (2H, m), 6.47 (1H, d, J=3.5 Hz), 6.98 (1H, d, J=3.5 Hz), 7.03-7.12 (2H, m), 7.26-7.29 (1H, m), 8.01 (1H, s)

Example 59

4-(2,4-Dichlorobenzyl)-1-(7H-pyrrolo[2,3-d]pyrimidin-4-yl)piperidin-4-ylamine

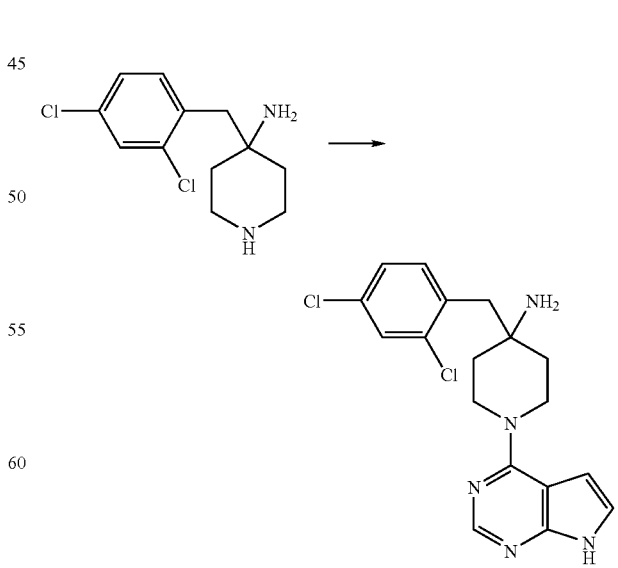

The title compound was prepared as described in Example 53. LC-MS (LCT2) m/z 376 [M+H$^+$], R$_t$ 3.53 min.

¹H NMR (MeOD) δ 1.59-1.62 (2H, m), 1.79-1.84 (2H, m), 2.98 (2H, s), 3.67-3.72 (2H, m), 4.38-4.41 (2H, m), 6.62-6.63 (1H, m), 7.11-7.13 (1H, m), 7.30-7.48 (3H, m), 8.11 (1H, s)

Example 60

4-(2-Chloro-4-fluorobenzyl)-1-(7H-pyrrolo[2,3-d]pyrimidin-4-yl)piperidin-4-ylamine

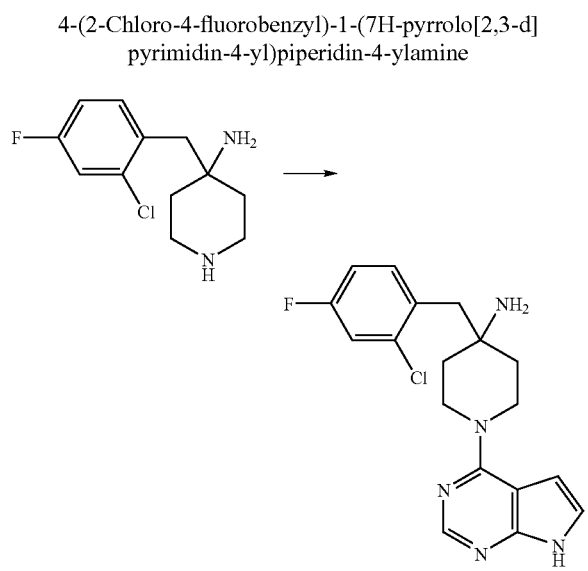

The title compound was prepared as described in Example 53. LC-MS (LCT2) m/z 360 [M+H⁺], R_t 2.98 min.

¹H NMR (MeOD) δ 1.56-1.59 (2H, m), 1.76-1.81 (2H, m), 2.92 (2H, s), 3.64-3.68 (2H, m), 4.36-4.38 (2H, m), 6.58-6.59 (1H, m), 7.01-7.05 (1H, m), 7.09-7.10 (1H, m), 7.19-7.21 (1H, m), 7.35-7.38 (1H, m), 8.11 (1H, s)

Example 61

4-(2,6-Dichlorobenzyl)-1-(7H-pyrrolo[2,3-d]pyrimidin-4-yl)piperidin-4-ylamine

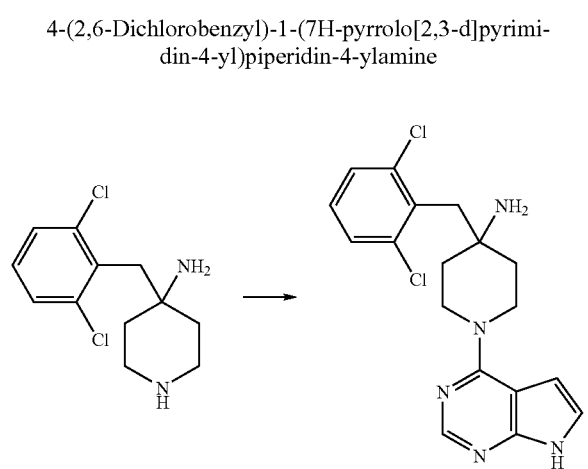

The title compound was prepared as described in Example 53. LC-MS (LCT2) m/z 376 [M+H⁺], R_t 3.11 min.

¹H NMR (MeOD) δ 1.70-1.73 (2H, m), 1.86-1.90 (2H, m), 3.24 (2H, s), 3.59-3.64 (2H, m), 4.41-4.44 (2H, m), 6.58-6.59 (1H, m), 7.08-7.09 (1H, m), 7.17-7.20 (1H, m), 7.38-7.40 (2H, m), 8.09 (1H, s)

Example 62

[4-(4-Chlorobenzyl)-1-(7H-pyrrolo[2,3-d]pyrimidin-4-yl)piperidin-4-yl]methylamine

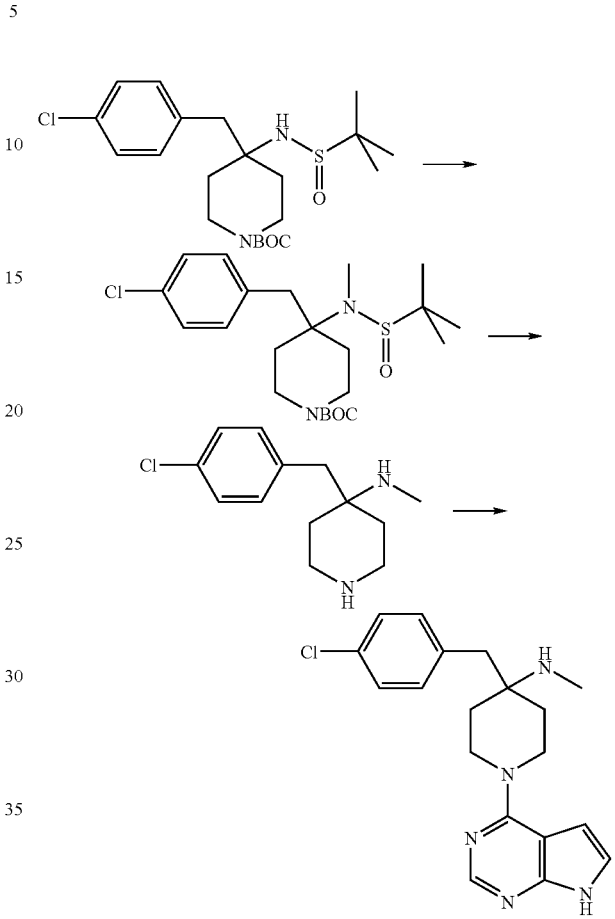

62A 4-(4-Chlorobenzyl)-4-(2-methylpropane-2-sulfinylamino)piperidine-1-carboxylic acid tert-butyl ester The title compound was prepared as described in Example 53. LC-MS (LCT2) m/z 451 [M+Na⁺], R_t 8.39 min.

62B 4-(4-Chlorobenzyl)-4-[methyl(2-methylpropane-2-sulfinyl)amino]piperidine-1-carboxylic acid tert-butyl ester To a solution of 4-(4-chlorobenzyl)-4-(2-methylpropane-2-sulfinylamino)-piperidine-1-carboxylic acid tert-butyl ester (205 mg, 0.478 mmol) in DMF (4.8 mL) at 0° C. was added sodium hydride (25 mg of a 60% dispersion in mineral oil, 0.621 mmol). After 15 min methyl iodide (33 □l, 0.526 mmol) was added, and the solution warmed to rt. After 12 h, sodium hydride (120 mg, 60% dispersion in mineral oil, 3.00 mmol) and methyl iodide (165 □l, 2.65 mmol) were added. After 30 min water (20 mL) was added and the solution extracted with ethyl acetate (3×20 mL). Organic extracts were combined, dried over magnesium sulphate and the resulting crude product was purified by silica column chromatography, eluting with 66% ethyl acetate-hexanes, to give the title product as an oil (163 mg, 77%). LC-MS (LCT2) m/z 465 [M+Na⁺], R_t 8.41 min.

62C [4-(4-Chlorobenzyl)piperidin-4-yl]methylamine

The title compound was prepared as described in Example 53 by treatment of the product of 62B with HCl. LC-MS (LCT2) m/z 239 [M+H⁺], R$_t$ 0.59 min.

62D [4-(4-Chlorobenzyl)-1-(7H-pyrrolo[2,3-d]pyrimidin-4-yl)piperidin-4-yl]methylamine The title compound was prepared as described in Example 53. LC-MS (LCT2) m/z 356 [M+H⁺], R$_t$ 2.72 min.

¹H NMR (MeOD) δ 1.62-1.65 (4H, m), 2.44 (3H, s), 2.82 (2H, s), 3.74-3.78 (2H, m), 4.21-4.34 (2H, m), 6.61-6.62 (1H, m), 7.10-7.12 (1H, m), 7.17-7.19 (2H, m), 7.30-7.32 (2H, m), 8.12 (1H, s)

Example 63

1-(7H-Pyrrolo[2,3-d]pyrimidin-4-yl)-4-(2trifluoromethoxybenzyl)piperidin-4-ylamine

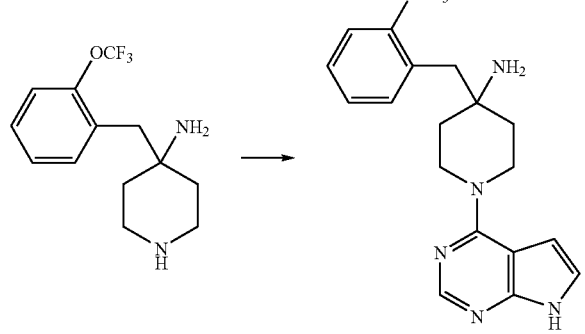

The title compound was prepared as described in Example 53. LC-MS (LCT2) m/z 392 [M+H⁺], R$_t$ 3.31 min.

¹H NMR (MeOD) δ 1.57-1.59 (2H, m), 1.74-1.78 (2H, m), 2.90 (2H, s), 3.73-3.78 (2H, m), 4.30-4.34 (2H, m), 6.59-6.61 (1H, m), 7.11-7.13 (1H, m), 7.33-7.44 (4H, m), 8.12 (1H, s)

Example 64

4-(2,5-Dichlorobenzyl)-1-(7H-pyrrolo[2,3-d]pyrimidin-4-yl)piperidin-4-ylamine

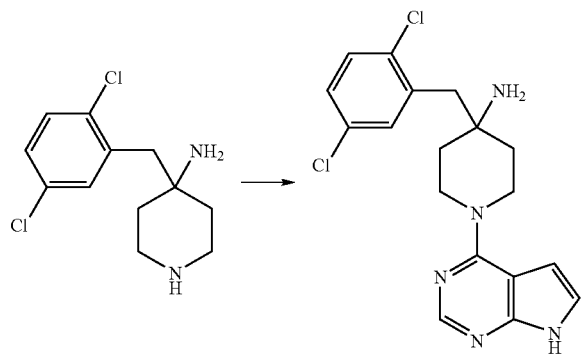 [SMILES: NC1(Cc2cc(Cl)ccc2Cl)CCNCC1 ; NC1(Cc2cc(Cl)ccc2Cl)CCN(c2ncnc3[nH]ccc23)CC1]

The title compound was prepared as described in Example 53. LC-MS (LCT2) m/z 376 [M+H⁺], R$_t$ 3.34 min.

¹H NMR (MeOD) δ 1.59-1.61 (2H, m), 1.79-1.84 (2H, m), 3.04 (2H, s), 3.64-3.69 (2H, m), 4.38-4.41 (2H, m), 6.59-6.60 (1H, m), 7.10-7.12 (1H, m), 7.21-7.25 (1H, m), 7.30-7.32 (1H, m), 7.41-7.43 (1H, m), 8.12 (1H, s)

Example 65

4-(2,3-Dichlorobenzyl)-1-(7H-pyrrolo[2,3-d]pyrimidin-4-yl)piperidin-4-ylamine

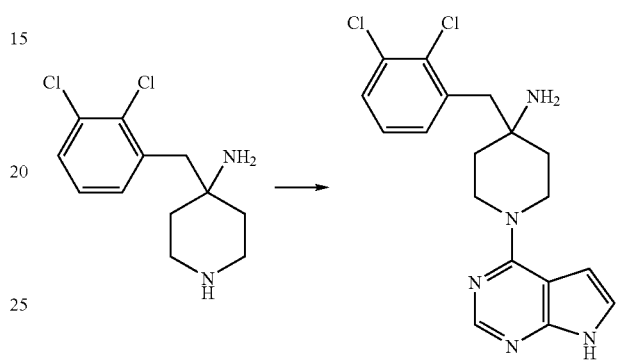

The title compound was prepared as described in Example 53. LC-MS (LCT2) m/z 376 [M+H⁺], R$_t$ 3.16 min.

¹H NMR (MeOD) δ 1.58-1.61 (2H, m), 1.79-1.84 (2H, m), 2.95 (2H, s), 3.64-3.69 (2H, m), 4.38-4.41 (2H, m), 6.59-6.60 (1H, m), 7.10-7.11 (1H, m), 7.21-7.25 (1H, m), 7.36-7.43 (2H, m), 8.11 (1H, s)

Example 66

4-(4-tert-Butylbenzyl)-1-(1H-pyrrolo[2,3-b]pyridin-4-yl)-piperidin-4-ylamine

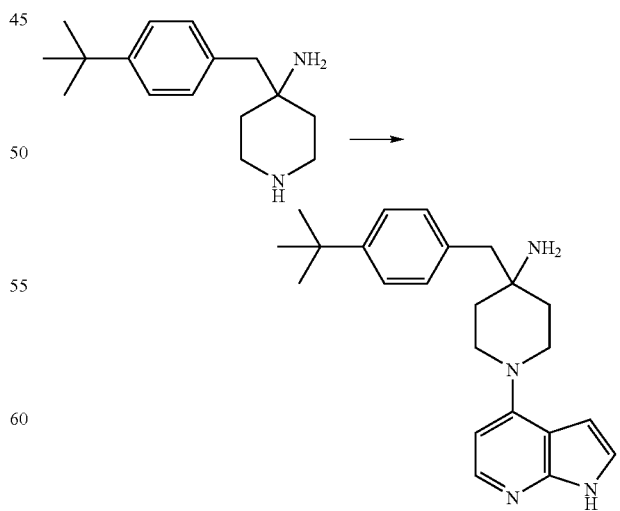

The title compound was prepared in a similar manner to Example 54. LC-MS (LCT2) m/z 363 [M+H⁺], R$_t$ 3.19 min.

$^1$H NMR (MeOD) δ 1.33 (9H, s), 1.60-1.65 (2H, m), 1.85-1.92 (2H, m), 2.81 (2H, s), 3.48-3.52 (2H, m), 3.70-3.78 (2H, s), 6.52-6.52 (2H, m), 7.17-7.21 (3H, m), 7.38-7.40 (2H, m), 7.90-7.91 (1H, m)

Example 67

4-(2,4-Dichlorobenzyl)-1-(1H-pyrrolo[2,3-b]pyridin-4-yl)-piperidin-4-ylamine

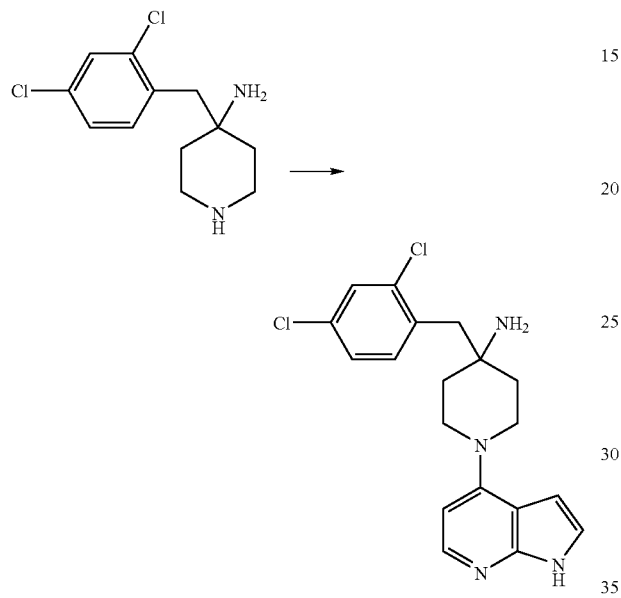

The title compound was prepared in a similar manner to Example 54. LC-MS (LCT2) m/z 375, 377, 379 [M+H$^+$], R$_t$ 2.80 min.

$^1$H NMR (MeOD) δ 1.52-1.55 (2H, m), 1.81-1.86 (2H, m), 2.90 (2H, s), 3.31-3.35 (2H, m), 3.68-3.70 (2H, m), 6.38-6.39 (2H, m), 7.06 (1H, d, J=4), 7.21 (1H, dd, J=8, 2 Hz), 7.29 (1H, d, J=8 Hz), 7.38 (1H, d, J=2), 7.80 (1H, d, J=6 Hz)

Example 68

C-[4-(4-Chlorophenyl)-1-(1H-pyrrolo[2,3-b]pyridin-4-yl)-piperidin-4-yl]-methylamine

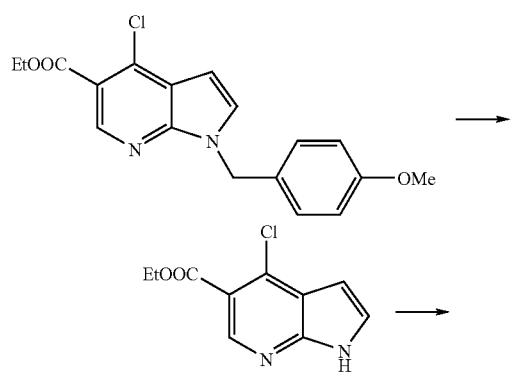

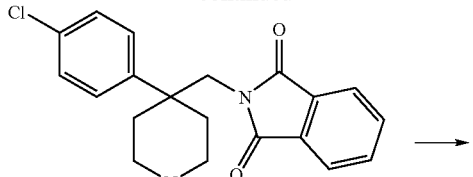

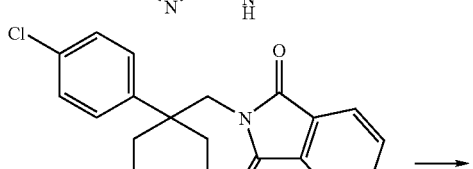

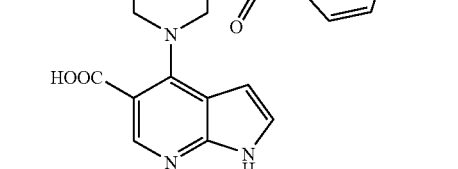

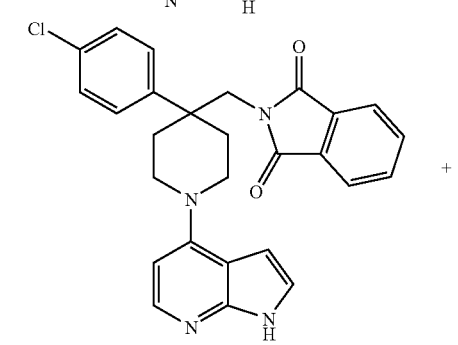

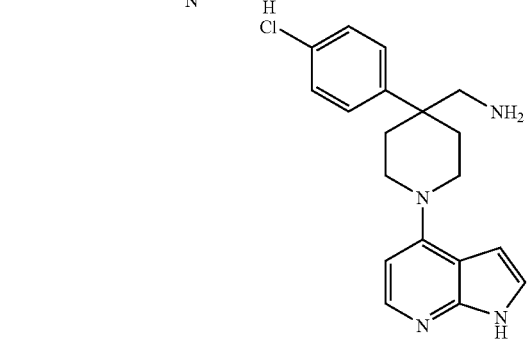

68A.
4-Chloro-1H-pyrrolo[2,3-b]pyridine-5-carboxylic acid ethyl ester

To a solution of 4-chloro-1-(4-methoxybenzyl)-1H-pyrrolo[2,3-b]pyridine-5-carboxylic acid ethyl ester (prepared as described in J. Heterocycl. Chem. 1972, 235 and Bioorg. Med. Chem. Lett. 2003, 2405) (3.48 g, 10 mmol) in TFA (20 mL), conc. H$_2$SO$_4$ (1.5 mL) and anisole (3 mL) were added at room temperature. The resulting solution was stirred at this temperature for 3 hours and then basified slowly by addition of ice-cold aqueous NaHCO$_3$. The aqueous solution was extracted with ethyl acetate and the combined organic layers were dried (Na$_2$SO$_4$) and concentrated. The residue was filtered and washed with n-hexanes to give a yellow solid (1.04 g, 46%). LC-MS (LCT2) m/z 226 [M+H⁺], $R_t$ 6.22 min.

68B 4-[4-(4-Chlorophenyl)-4-(1,3-dioxo-1,3-dihydroisoindol-2-ylmethyl)-piperidin-1-yl]-1H-pyrrolo[2,3-b]pyridine-5-carboxylic acid ethyl ester A mixture of 4-chloro-1H-pyrrolo[2,3-b]pyridine-5-carboxylic acid ethyl ester (34 mg, 0.15 mmol), and 2-[4-(4-chlorophenyl)-piperidin-4-ylmethyl]-isoindole-1,3-dione (prepared by treatment of C-[4-(4-chlorophenyl)piperidin-4-yl]methylamine hydrochloride, Example 14, Step C with phthalic anhydride in acetic acid at 120° C.) (54 mg, 0.15 mmol) and triethylamine (0.1 mL) in n-butanol (2 mL) was irradiated in a microwave reactor (300 W) for 1 hr at 120° C. with simultaneous air-cooling. The resulting solids were broken up, washed with methanol, filtered and dried to give a cream-coloured solid (49 mg, 60%). LC-MS (LCT2) m/z 544 [M+H⁺], $R_t$ 7.83 min.

68C. 4-[4-(4-Chlorophenyl)-4-(1,3-dioxo-1,3-dihydroisoindol-2-ylmethyl)-piperidin-1-yl]-1H-pyrrolo[2,3-b]pyridine-5-carboxylic acid 4-[4-(4-Chlorophenyl)-4-(1,3-dioxo-1,3-dihydroisoindol-2-ylmethyl)-piperidin-1-yl]-1H-pyrrolo[2,3-b]pyridine-5-carboxylic acid ethyl ester (49 mg, 0.09 mmol) was hydrolysed in a mixture of 2M NaOH (1 mL) and 1,4-dioxane (1 mL) at 80° C. overnight. The solution was acidified by dropwise addition of conc. HCl. Solvents were evaporated and the resulting solid was filtered and washed with water, then dried. A white solid (45 mg) was obtained which was used in the next step without further purification.

68D. C-[4-(4-Chloro-phenyl)-1-(1H-pyrrolo[2,3-b]pyridin-4-yl)-piperidin-4-yl]-methylamine A mixture of crude 4-[4-(4-chlorophenyl)-4-(1,3-dioxo-1,3-dihydroisoindol-2-ylmethyl)-piperidin-1-yl]-1H-pyrrolo[2,3-b]pyridine-5-carboxylic acid (12.8 mg, 0.025 mmol) and water (1 mL) was irradiated in a microwave reactor (250 W) for 2 hrs at 180° C. The resulting suspension was filtered and the filtrate was concentrated. Preparative TLC gave the product (4 mg, 47%). LC-MS (LCT2) m/z 342 [M+H⁺], $R_t$ 2.19 min.

¹H NMR (MeOD) δ 2.00 (2H, m), 2.42 (2H, m), 2.85 (2H, s), 3.40 (2H, m), 4.00 (2H, m), 6.45 (1H, d, J=5.8 Hz), 7.50 (4H, m), 8.06 (1H, d, J=5.8 Hz), 8.2 (1H, s)

Example 69

4-Amino-1-(7H-pyrrolo[2,3-d]pyrimidin-4-yl)-piperidine-4-carboxylic acid 4-chloro-benzylamide

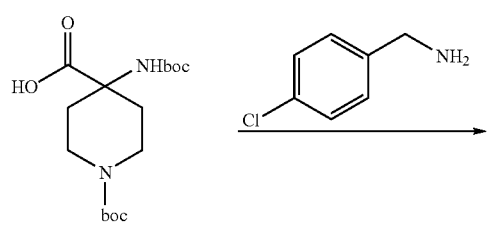

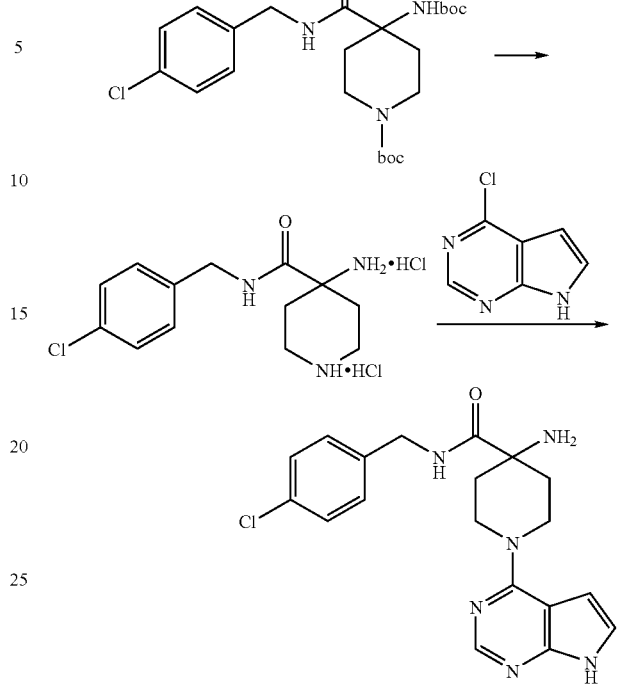

69A. 4-tert-Butoxycarbonylamino-4-(4-chloro-benzylcarbamoyl)-piperidine-1-carboxylic acid tert-butyl ester Dry DMF (1 mL) was added to a mixture of 4-tert-butoxycarbonylamino-piperidine-1,4-dicarboxylic acid mono tert-butyl ester (151 mg, 0.44 mmol) and HATU (220 mg, 0.58 mmol) under nitrogen. N-Ethyldiisopropylamine (0.38 mL, 2.1 mmol) was added to the solution and the reaction mixture was stirred for 15 min. 4-Chlorobenzylamine (70 uL, 0.57 mmol) was added and the solution was stirred for 23 h at rt and under nitrogen. The reaction mixture was partioned between dichloromethane (10 mL) and water (10 mL). The aqueous phase was further extracted with dichloromethane (20 mL). The combined organic layers were dried (Mg₂SO₄), filtered and concentrated. Flash column chromatography on silica, eluting with 4% methanol in dichloromethane, gave 4-tert-butoxycarbonylamino-4-(4-chloro-benzylcarbamoyl)-piperidine-1-carboxylic acid tert-butyl ester (177 mg, 0.38 mmol, 86%). LC-MS (LCT2) m/z 490 [M+Na⁺], $R_t$ 8.09 min.

69B. 4-Amino-piperidine-4-carboxylic acid 4-chloro-benzylamide dihydrochloride A 4M solution of HCl in dioxane (7.7 ml, 31 mmol) was added dropwise to a solution of 4-tert-butoxycarbonylamino-4-(4-chloro-benzylcarbamoyl)-piperidine-1-carboxylic acid tert-butyl ester (96 mg, 0.20 mmol) in methanol (7.7 mL) and stirred at rt for 17 h. The solvents were concentrated to give 4-amino-piperidine-4-carboxylic acid 4-chloro-benzylamide dihydrochloride (71 mg, 0.20 mmol, 100%) that was used in the next step without further purification.

¹H NMR (500 MHz, CD₃OD): 2.18 (2H, m), 2.64 (2H, m), 3.44 (4H, m), 4.47 (2H, s), 7.36 (4H, m).

69C. 4-Amino-1-(7H-pyrrolo[2,3-d]pyrimidin-4-yl)-piperidine-4-carboxylic acid 4-chloro-benzylamide A degassed mixture of 4-amino-piperidine-4-carboxylic acid 4-chloro-benzylamide dihydrochloride (48 mg, 0.13 mmol), 4-chloro-7H-pyrrolo[2,3-d]pyrimidine (21 mg, 0.12 mmol), triethylamine (126 uL, 0.9 mmol) and n-butanol (1.2 mL) was stirred at 100° C. for 18 h. The solvents were removed by evaporation and the crude mixture was first purified on a SCX-II acid resin, eluting with methanol then 2M ammonia/methanol, and then by preparative TLC, eluting with 10% methanol in dichloromethane, to give 4-amino-1-(7H-pyrrolo[2,3-d]pyrimidin-4-yl)-piperidine-4-carboxylic acid 4-chloro-benzylamide (37 mg, 0.096 mmol, 80%). LC-MS (LCT2) m/z 385 [M+H$^+$], R$_t$ 2.84 min.
$^1$H NMR (MeOD) δ 1.60-1.62 (2H, m), 2.19-2.25 (2H, m), 3.65-3.71 (2H, m), 4.38 (2H, s), 4.47-4.50 (2H, m), 6.65 (1H, d, J=4 Hz), 7.14 (1H, d, J=4 Hz), 7.27-7.33 (4H, m), 8.14 (1H, s)

Example 70

4-Amino-1-(7H-pyrrolo[2,3-d]pyrimidin-4-yl)-piperidine-4-carboxylic acid 3-chloro-benzylamide

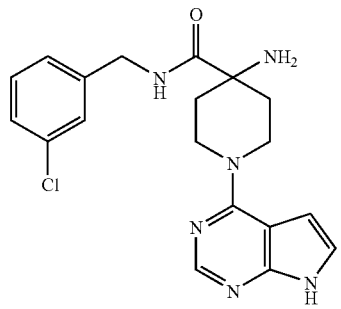 [SMILES: NC1(C(=O)NCc2cccc(Cl)c2)CCN(c2ncnc3[nH]ccc23)CC1]

The title compound was prepared as described for Example 69. LC-MS (LCT2) m/z 385 [M+H$^+$], R$_t$ 2.94 min.
$^1$H NMR (MeOD) δ 1.60-1.63 (2H, m), 2.20-2.25 (2H, m), 3.65-3.71 (2H, m), 4.39 (2H, s), 4.48-4.51 (2H, m), 6.65 (1H, d, J=4 Hz), 7.14 (1H, d, J=4 Hz), 7.22-7.32 (4H, m), 8.14 (1H, s)

Example 71

4-Amino-1-(7H-pyrrolo[2,3-d]pyrimidin-4-yl)-piperidine-4-carboxylic acid 4-trifluoromethyl-benzylamide

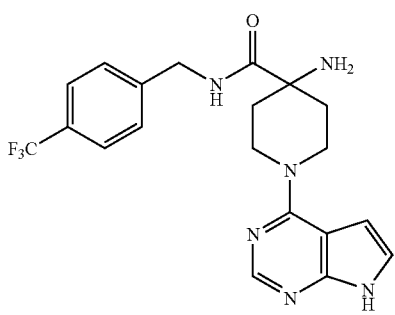 [SMILES: NC1(C(=O)NCc2ccc(C(F)(F)F)cc2)CCN(c2ncnc3[nH]ccc23)CC1]

The title compound was prepared as described for Example 69. LC-MS (LCT2) m/z 419 [M+H$^+$], R$_t$ 3.26 min.
$^1$H NMR (MeOD) δ 1.62-1.64 (2H, m), 2.20-2.26 (2H, m), 3.65-3.71 (2H, m), 4.48-4.51 (4H, m), 6.65 (1H, d, J=4 Hz), 7.14 (1H, d, J=4 Hz), 7.49 (2H, d, J=8 Hz), 7.63 (2H, d, J=8 Hz), 8.14 (1H, s)

Example 72

4-Amino-1-(7H-pyrrolo[2,3-d]pyrimidin-4-yl)-piperidine-4-carboxylic acid 4-fluoro-benzylamide

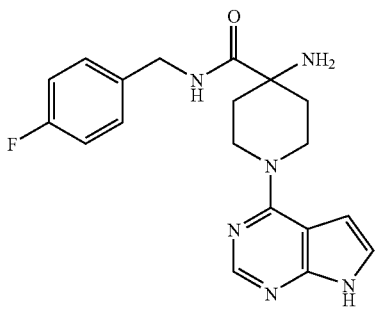

The title compound was prepared as described for Example 69. LC-MS (LCT2) m/z 369 [M+H$^+$], R$_t$ 2.43 min.
$^1$H NMR (MeOD) δ 1.59-1.62 (2H, m), 2.19-2.25 (2H, m), 3.65-3.70 (2H, m), 4.38 (2H, s), 4.47-4.50 (2H, m), 6.65 (1H, d, J=4 Hz), 7.05 (2H, dd, J=8.5 Hz), 7.14 (1H, d, J=4 Hz), 7.30-7.33 (2H, m), 8.14 (1H, s)

Example 73

4-Amino-1-(7H-pyrrolo[2,3-d]pyrimidin-4-yl)-piperidine-4-carboxylic acid 2-chloro-benzylamide

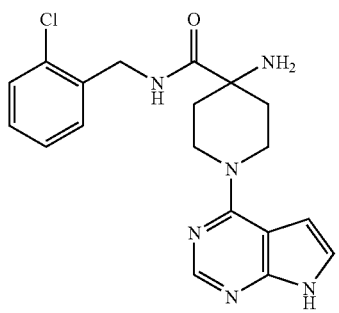 [SMILES: NC1(C(=O)NCc2ccccc2Cl)CCN(c2ncnc3[nH]ccc23)CC1]

The title compound was prepared as described for Example 69. LC-MS (LCT2) m/z 385 [M+H$^+$], R$_t$ 2.77 min.
$^1$H NMR (MeOD) δ 1.61-1.64 (2H, m), 2.21-2.26 (2H, m), 3.66-3.71 (2H, m), 4.49-4.50 (4H, m), 6.65 (1H, d, J=4 Hz), 7.14 (1H, d, J=4 Hz), 7.27-7.41 (4H, m), 8.14 (1H, s)

Example 74

4-Amino-1-(7H-pyrrolo[2,3-d]pyrimidin-4-yl)-piperidine-4-carboxylic acid 4-trifluoromethoxy-benzylamide

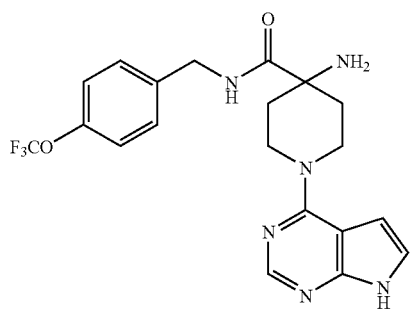 [SMILES: NC1(C(=O)NCc2ccc(OC(F)(F)F)cc2)CCN(c2ncnc3[nH]ccc23)CC1]

The title compound was prepared as described for Example 69. LC-MS (LCT2) m/z 435 [M+H⁺], R$_t$ 3.55 min.

¹H NMR (MeOD) δ 1.61-1.63 (2H, m), 2.20-2.25 (2H, m), 3.66-3.71 (2H, m), 4.42 (2H, s), 4.48-4.51 (2H, m), 6.65 (1H, d, J=4 Hz), 7.14 (1H, d, J=4 Hz), 7.24 (2H, d, J=7 Hz), 7.40 (2H, d, J=7 Hz), 8.14 (1H, s)

Example 75

4-Amino-1-(7H-pyrrolo[2,3-d]pyrimidin-4-yl)-piperidine-4-carboxylic acid (4-chloro-benzyl)-methylamide

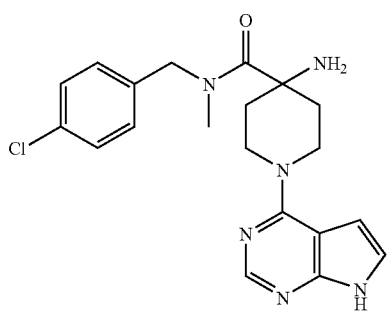 [SMILES: CN(Cc1ccc(Cl)cc1)C(=O)C1(N)CCN(c2ncnc3[nH]ccc23)CC1]

The title compound was prepared as described for Example 69. LC-MS (LCT2) m/z 399 [M+H⁺], R$_t$ 3.13 min.

¹H NMR (MeOD) δ 1.76-1.78 (2H, m), 2.33-2.37 (2H, m), 3.18 (3H, br s), 4.02-4.11 (4H, m), 4.95 (2H, s), 6.62-6.64 (1H, m), 7.10-7.13 (1H, m), 7.22-7.26 (2H, m), 7.32-7.36 (2H, m), 8.13 (1H, s)

Example 76

4-Amino-1-(7H-pyrrolo[2,3-d]pyrimidin-4-yl)-piperidine-4-carboxylic acid 4-tert-butyl-benzylamide

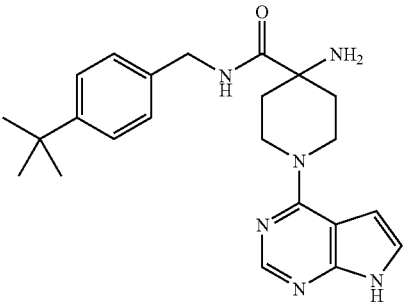 [SMILES: CC(C)(C)c1ccc(CNC(=O)C2(N)CCN(c3ncnc4[nH]ccc34)CC2)cc1]

The title compound was prepared as described for Example 69. LC-MS (LCT2) m/z 407 [M+H⁺], R$_t$ 4.28 min.

¹H NMR (MeOD) δ 1.31 (9H, s), 1.56-1.63 (2H, m), 2.18-2.25 (2H, m), 3.60-3.70 (2H, m), 4.37 (2H, s), 4.40-4.50 (2H, m), 6.65 (1H, d, J=4 Hz), 7.14 (1H, d, J=4 Hz), 7.24 (2H, d, J=8 Hz), 7.36 (2H, d, J=8 Hz), 8.14 (1H, s)

Example 77

4-Amino-1-(7H-pyrrolo[2,3-d]pyrimidin-4-yl)-piperidine-4-carboxylic acid 2,4-dichloro-benzylamide

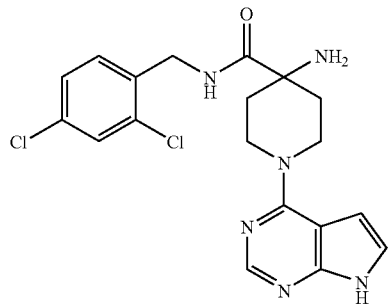 [SMILES: NC1(C(=O)NCc2ccc(Cl)cc2Cl)CCN(c2ncnc3[nH]ccc23)CC1]

The title compound was prepared as described for Example 69. LC-MS (LCT2) m/z 419 [M+H⁺], R$_t$ 3.69 min.

¹H NMR (MeOD) δ 1.62-1.64 (2H, m), 2.17-2.25 (2H, m), 3.65-3.71 (2H, m), 4.47-4.51 (4H, m), 6.65 (1H, d, J=4 Hz), 7.14 (1H, d, J=4 Hz), 7.31-7.33 (2H, m), 7.47-7.47 (1H, d, J=1.5 Hz), 8.14 (1H, s)

Example 78

4-Amino-1-(7H-pyrrolo[2,3-d]pyrimidin-4-yl)-piperidine-4-carboxylic acid 3,4-dichloro-benzylamide

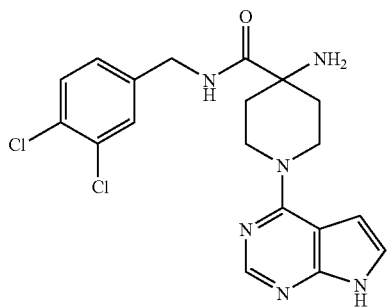 [SMILES: NC1(C(=O)NCc2ccc(Cl)c(Cl)c2)CCN(c2ncnc3[nH]ccc23)CC1]

The title compound was prepared as described for Example 69. LC-MS (LCT2) m/z 419 [M+H$^+$], R$_t$ 3.65 min.

$^1$H NMR (MeOD) δ 1.60-1.62 (2H, m), 2.18-2.24 (2H, m), 3.65-3.70 (2H, m), 4.37 (2H, s), 4.48-4.50 (2H, m), 6.64 (1H, d, J=4 Hz), 7.13 (1H, d, J=4 Hz), 7.22-7.24 (1H, m), 7.46-7.48 (2H, m), 8.14 (1H, s)

Example 79

4-(4-Chloro-benzyloxymethyl)-1-(7H-pyrrolo[2,3-d]pyrimidin-4-yl)-piperidin-4-ylamine

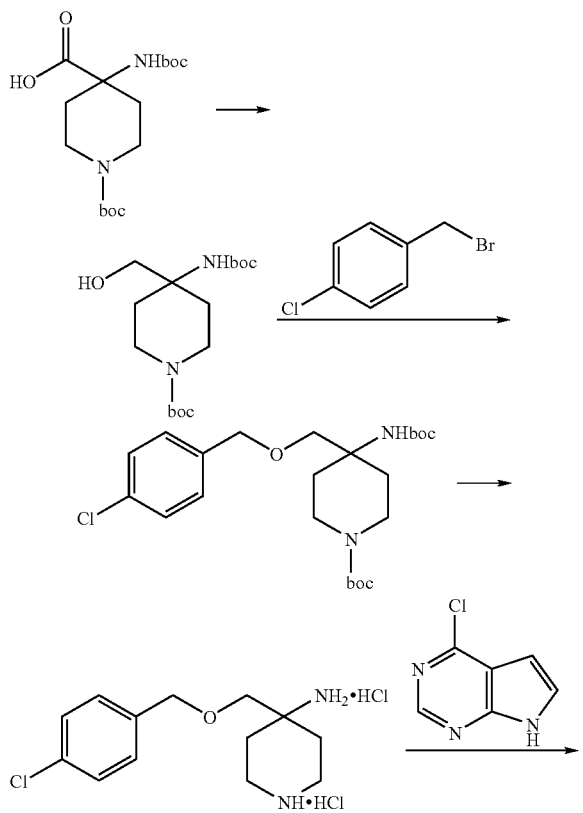

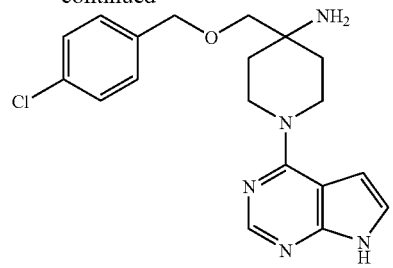

79A. 4-tert-Butoxycarbonylamino-4-hydroxymethyl-piperidine-1-carboxylic acid tert-butyl ester A 1M solution of lithium aluminium hydride in tetrahydrofuran (1.66 mL, 1.66 mmol) was added dropwise to a cooled (0° C.) solution of 4-tert-butoxycarbonylamino-piperidine-1,4-dicarboxylic acid mono-tert-butyl ester (400 mg, 1.1 mmol) in dry tetrahydrofuran (5 mL). The solution was stirred for 3 h at rt under nitrogen. Water (172 μL) and 10% sodium hydroxide aq (232 μL) were added and the mixture was stirred for 2 h. Further water (172 μL) was added and the mixture was filtered through a pad of celite and washed with diethyl ether. The crude product was purified by flash column chromatography on silica, eluting with 10% methanol in dichloromethane, to give 4-tert-butoxycarbonylamino-4-hydroxymethyl-piperidine-1-carboxylic acid tert-butyl ester (178 mg, 0.54 mmol, 49%). LC-MS (LCT2) m/z 353 [M+Na$^+$], R$_t$ 6.67 min.

79B. 4-tert-Butoxycarbonylamino-4-(4-chloro-benzyloxymethyl)-piperidine-1-carboxylic acid tert-butyl ester Sodium hydride (60% suspension in oil, 4.9 mg, 0.11 mmol) was added in small portions to a cooled (0° C.) solution of 4-tert-butoxycarbonylamino-4-hydroxymethyl-piperidine-1-carboxylic acid tert-butyl ester (19 mg, 0.057 mmol) in dry DMF (0.2 mL). The suspension was stirred vigorously at 0° C. for 15 min followed by addition of 4-chlorobenzyl bromide (14 mg, 0.066 mmol). After stirring for 45 min at 0° C., the reaction mixture was warmed to rt. When TLC showed complete consumption of the starting material, the reaction mixture was partioned between ethyl acetate (5 mL) and water (2 mL). The aqueous phase was further extracted with ethyl acetate (5 mL). The combined organic layers were dried (Mg$_2$SO$_4$), filtered and concentrated. Flash column chromatography on silica, eluting with 1% methanol in dichloromethane, gave 4-tert-butoxycarbonylamino-4-(4-chloro-benzyloxymethyl)-piperidine-1-carboxylic acid tert-butyl ester (6 mg, 0.013 mmol, 22%). LC-MS (LCT2) m/z 477 [M+Na$^+$], R$_t$ 8.74 min.

79C. 4-(4-Chloro-benzyloxymethyl)-piperidin-4-ylamine dihydrochloride

A 4M solution of HCl in dioxane (0.68 ml, 2.7 mmol) was added dropwise to a solution of 4-tert-butoxycarbonylamino- 4-(4-chloro-benzyloxymethyl)-piperidine-1-carboxylic acid tert-butyl ester (12 mg, 0.028 mmol) in methanol (1 mL). The solution was stirred at rt for 17 h. The solvents were removed by evaporation to give 4-(4-chloro-benzyloxymethyl)-piperidin-4-ylamine dihydrochloride (9.2 mg, 0.028 mmol, 100%) that was used in the next step without further purification.

$^1$H NMR (500 MHz, CD$_3$OD): 2.12-2.24 (4H, m), 3.22-3.32 (2H, m), 3.42-3.45 (2H, m), 3.75 (2H, s), 4.66 (2H, s), 7.38-7.43 (4H, m).

79D. 4-(4-Chloro-benzyloxymethyl)-1-(7H-pyrrolo [2,3-d]pyrimidin-4-yl)-piperidin-4-ylamine A degassed mixture of 4-(4-chloro-benzyloxymethyl)-piperidin-4-ylamine dihydrochloride (9.2 mg, 0.028 mmol), 4-chloro-7H-pyrrolo[2,3-d]pyrimidine (5.9 mg, 0.035 mmol), triethylamine (36 uL, 0.2 mmol) and n-butanol (0.35 mL) was stirred at 100° C. for 17 h. The solvents were removed by evaporation. The crude mixture was purified on an SCX-II acid resin, eluting with methanol then 2M ammonia/methanol, and then by preparative TLC eluting with 10% methanol in dichloromethane, to give 4-(4-chloro-benzyloxymethyl)-1-(7H-pyrrolo[2,3-d]pyrimidin-4-yl)-piperidin-4-ylamine (8.2 mg, 0.022 mmol, 78%). LC-MS (LCT2) m/z 372 [M+H$^+$], R$_t$ 3.19 min.

$^1$H NMR (MeOD) δ 1.66-1.70 (2H, m), 1.86-1.88 (2H, m), 3.47 (2H, s), 3.95-3.98 (2H, m), 4.03-4.06 (2H, m), 4.57 (2H, s), 6.62 (1H, d, J=4 Hz), 7.13 (1H, d, J=4 Hz), 7.34-7.37 (4H, m), 8.14 (1H, s)

Example 80

4-Amino-1-(7H-pyrrolo[2,3-d]pyrimidin-4-yl)-piperidine-4-carboxylic acid 2,4-difluoro-benzylamide

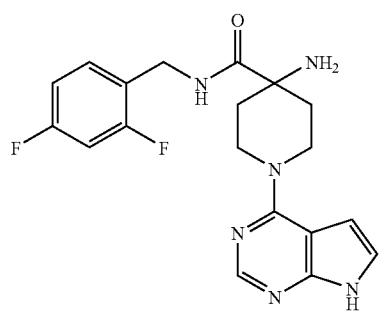 [SMILES: NC1(C(=O)NCc2ccc(F)cc2F)CCN(c2ncnc3[nH]ccc23)CC1]

The title compound was prepared as described for Example 69. LC-MS (LCT2) m/z 387 [M+H$^+$], R$_t$ 2.46 min.

$^1$H NMR (MeOD) δ 1.59-1.61 (2H, m), 2.18-2.24 (2H, m), 3.66-3.71 (2H, m), 4.43 (2H, s), 4.46-4.49 (2H, m), 6.63 (1H, d, J=4 Hz), 6.92-6.96 (2H, m), 7.13 (1H, d, J=4 Hz), 7.84-7.87 (1H, m), 8.14 (1H, s)

Example 81

[4-Amino-1-(7H-pyrrolo [2,3-d]pyrimidin-4-yl)-piperidin-4-yl]-(3,4-dihydro-1H-isoquinolin-2-yl)-methanone

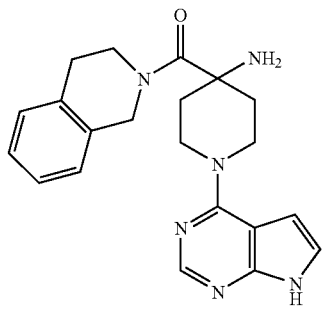 [SMILES: NC1(C(=O)N2CCc3ccccc3C2)CCN(c2ncnc3[nH]ccc23)CC1]

The title compound was prepared according to the method described in Example 69. LC-MS (LCT2) m/z 377 [M+H$^+$], R$_t$ 2.73 min.

$^1$H NMR (CD$_3$OD) δ 1.70-1.80 (2H, m), 2.25-2.35 (2H, m), 2.80-2.95 (2H, m), 4.04-4.08 (6H, m), 4.90-5.00 (2H, m), 6.63 (1H, s), 7.05-7.16 (5H, m), 8.14 (1H, s).

Example 82

[4-Amino-1-(7H-pyrrolo[2,3-d]pyrimidin-4-yl)-piperidin-4-yl]-(2-phenyl-pyrrolidin-1-yl)-methanone

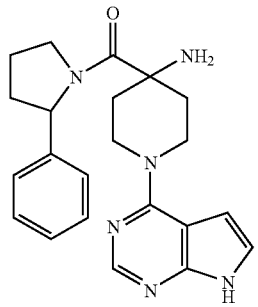 [SMILES: NC1(C(=O)N2CCCC2c2ccccc2)CCN(c2ncnc3[nH]ccc23)CC1]

The title compound was prepared according to the method described in Example 69. LC-MS (LCT2) m/z 391 [M+H$^+$], R$_t$ 2.68 min.

$^1$H NMR (CD$_3$OD) δ 1.50-2.31 (8H, m), 3.65-4.04 (5H, m), 4.20-4.40 (1H, m), 5.10-5.20 (1H, m), 6.63 (1H, s), 7.12-7.29 (6H, m), 8.11 (1H, s).

Example 83

4-(4-Chlorobenzyl)-1-(1H-pyrazolo[3,4-b]pyridin-4-yl)-piperidin-4-ylamine

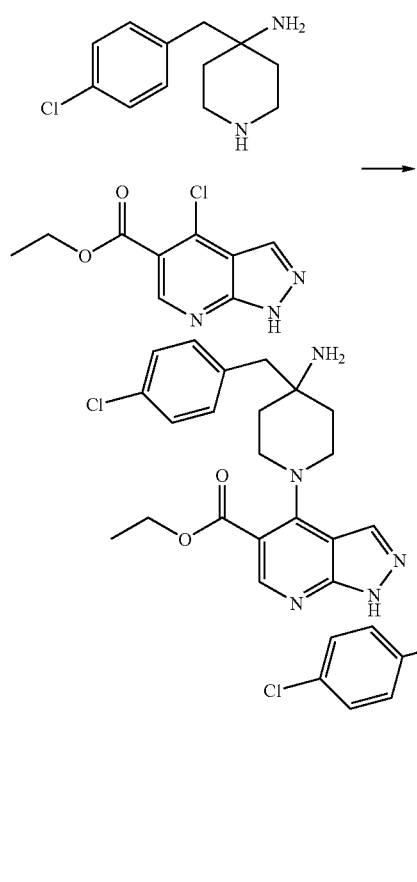

83A. 4-[4-Amino-4-(4-chlorobenzyl)-piperidin-1-yl]-1H-pyrazolo[3,4-b]pyridine-5-carboxylic acid ethyl ester A mixture of 4-chloro-1H-pyrrolo[2,3-b]pyridine-5-carboxylic acid ethyl ester (Example 68A) (50 mg, 0.22 mmol), 4-(4-chlorobenzyl)-piperidin-4-ylamine hydrochloride (65 mg, 0.22 mmol) and triethylamine (150μ) in n-butanol (1.5 mL) was irradiated in a microwave reactor (200 W) for 1 hr at 100° C. After cooling, the solvent was evaporated. The solids obtained were dissolved in ethyl acetate, the organic layer was washed with aqueous sodium hydrogen carbonate, brine and then dried ($Na_2SO_4$). Evaporation of the organic solution gave 4-[4-amino-4-(4-chlorobenzyl)-piperidin-1-yl]-1H-pyrazolo[3,4-b]pyridine-5-carboxylic acid ethyl ester as an off-white solid (80 mg, 87%). LC-MS (LCT2) m/z 415 [M+H$^+$], R$_t$ 3.99 mm.

$^1$H NMR (d$_6$-DMSO) δ 1.30 (3H, t, J=7 Hz), 1.36 (2H, m), 1.68 (2H, m), 2.68 (2H, s), 3.50 (2H, m), 3.60 (2H, m), 4.25 (2H, q, J=7 Hz), 7.25 (2H, d, J=8.3 Hz), 7.35 (2H, d, J=8.3 Hz), 8.20 (1H, s), 8.40 (1H, s), 13.50 (1H, s)

83B. 4-(4-Chlorobenzyl)-1-(1H-pyrazolo[3,4-b]pyridin-4-yl)-piperidin-4-ylamine 4-[4-Amino-4-(4-chlorobenzyl)-piperidin-1-yl]-1H-pyrazolo[3,4-b]pyridine-5-carboxylic acid ethyl ester (55 mg, 0.13 mmol) was suspended in 2M potassium hydroxide (1.5 mL) and irradiated in a microwave reactor (250 W) for 2 hours at 120° C. After cooling, water (2 mL) was added and the solids formed were collected by filtration. The filtrate was extracted with ethyl acetate (2×4 mL) and dried ($Na_2SO_4$). The extracts were evaporated and the resulting yellow solids were combined with the previous material and dissolved in acetone (10 mL) and n-hexanes (2 mL). The solvents were concentrated until precipitation occurred. The solids were collected by filtration and washed with n-hexanes to give 4-(4-chlorobenzyl)-1-(1H-pyrazolo[3,4-b]pyridin-4-yl)-piperidin-4-ylamine as a light yellow powder (26 mg, 57%). LC-MS (LCT2) m/z 342 [M+H$^+$], R$_t$ 2.07 min.

$^1$H NMR (d$_6$-DMSO) δ 1.38 (2H, m), 1.62 (2H, m), 2.65 (2H, s), 3.50 (2H, m), 3.85 (2H, m), 6.35 (1H, d, J=5 Hz), 7.27 (2H, d, J=8 Hz), 7.34 (2H, d, J=8 Hz), 8.02 (1H, d, J=5 Hz), 8.15 (1H, s), 13.13 (1H, s)

Example 84

4-(4-tert-Butyl-benzyl)-1-(1H-pyrazolo[3,4-b]pyridine-4-yl)-piperidin-4-ylamine

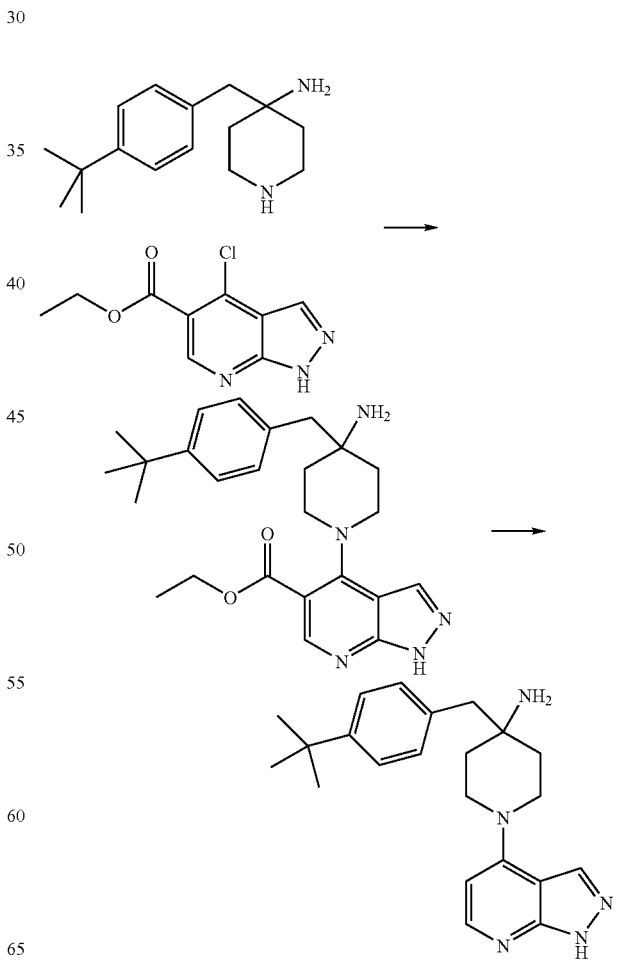

84A. 4-[4-Amino-4-(4-tert-butyl-benzyl)-piperidin-1-yl]-1H-pyrazolo[3,4-b]pyridine-5-carboxylic acid ethyl ester A mixture of 4-chloro-1H-pyrrolo[2,3-b]pyridine-5-carboxylic acid ethyl ester (Example 68A) (50 mg, 0.22 mmol), 4-(4-tert-butyl-benzyl)-piperidin-4-ylamine hydrochloride (70.8 mg, 0.22 mmol) and triethylamine (150 µL) in n-butanol (1.5 mL) was irradiated in a microwave reactor (200 W) for 1 hour at 100° C. After cooling, the solvent was evaporated and the residue was purified by column chromatography (EtOAc-MeOH 4:1) to give an off-white solid (63 mg, 65%). LC-MS (LCT2) m/z 436 [M+H$^+$], R$_t$ 5.01 min.

$^1$H NMR (d$_6$-DMSO) δ 1.38 (9H, s), 1.38 (3H, t, J=7 Hz), 1.85 (4H, m), 3.0 (2H, s), 3.62 (2H, m), 3.70 (2H, m), 4.25 (2H, q, J=7 Hz), 7.15 (2H, d, J=8.2 Hz), 7.30 (2H, d, J=8.2 Hz), 8.20 (1H, s), 8.40 (1H, s), 13.45 (1H, s)

84B. 4-(4-tert-Butyl-benzyl)-1-(1H-pyrazolo[3,4-b]pyridin-4-yl)-piperidin-4-ylamine 4-[4-Amino-4-(4-tert-butyl-benzyl)-piperidin-1-yl]-1H-pyrazolo[3,4-b]pyridine-5-carboxylic acid ethyl ester (23 mg, 0.053 mmol) was suspended in 2M potassium hydroxide (1 mL) and irradiated in a microwave reactor (250 W) for 2 hours at 120° C. After cooling, water (2 mL) was added and the aqueous layer was extracted with ethyl acetate (2×4 mL). The organic layers were dried (Na$_2$SO$_4$) and concentrated to give a yellow solid (9 mg, 47%). LC-MS (LCT2) m/z 364 [M+H$^+$], R$_t$ 2.80 min.

$^1$H NMR (CD$_3$OD) δ 1.32 (9H, s), 1.63 (2H, m), 1.86 (2H, m), 2.80 (2H, s), 3.70 (2H, m), 3.95 (2H, m), 6.46 (1H, d, J=5.8 Hz), 7.20 (2H, J=8 Hz), 7.40 (2H, J=8 Hz), 8.08 (1H, d, J=5.8 Hz), 8.20 (1H, s)

Example 85

4-(4-tert-Butyl-benzyl)-1-(1H-pyrrolo[2,3-b]pyridin-4-yl)-piperidin-4-ylamine

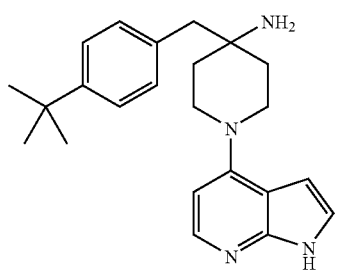 [SMILES: CC(C)(C)c1ccc(CC2(N)CCN(c3ccnc4[nH]ccc34)CC2)cc1]

The title compound was prepared as described for Example 54. LC-MS (LCT2) m/z 363 [M+H$^+$], R$_t$ 3.19 min.

$^1$H NMR (CD$_3$OD) δ 1.33 (9H, s), 1.60-1.65 (2H, m), 1.85-1.90 (2H, m), 2.81 (2H, s), 3.48-3.52 (2H, m), 3.72-3.78 (2H, m), 6.50-6.52 (2H, m), 7.17-7.21 (3H, m), 7.39 (2H, d, J=8 Hz), 7.92 (1H, d, J=5 Hz)

Example 86

N-[4-Amino-1-(7H-pyrrolo[2,3-d]pyrimidin-4-yl)-piperidin-4-ylmethyl]-4-chloro-benzamide

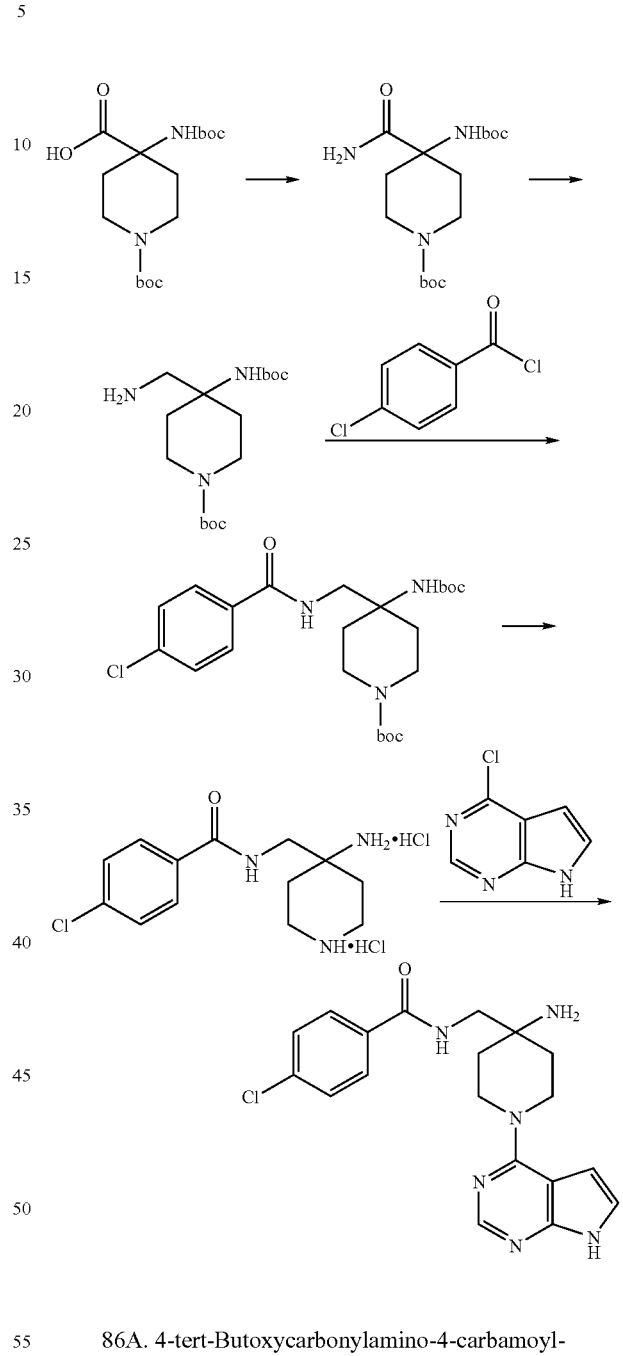

86A. 4-tert-Butoxycarbonylamino-4-carbamoyl-piperidine-1-carboxylic acid tert-butyl ester 1-Hydroxybenzotriazole hydrate (150 mg, 1.1 mmol) and 1-(3-dimethylaminopropyl)-3-ethyl-carbodiimide hydrochloride (214 mg, 1.1 mmol) were added to a stirred solution of 4-tert-butoxycarbonylamino-piperidine-1,4-dicarboxylic acid mono-tert-butyl ester (149 mg, 0.44 mmol) in DMF (9 mL). The reaction mixture was stirred for 80 minutes, and ammonium hydroxide (1.2 mL, ammonia sol. aq.) was added. After stirring for a further 20 hours at room temperature, brine (18 mL) and water (3 mL) were added to the reaction mixture. The aqueous phase was extracted with ethyl acetate (2×12 mL) and the combined organic phases were dried (Mg$_2$SO$_4$), filtered and concentrated to give 4-tert-butoxycarbonylamino-4-carbamoyl-piperidine-1-carboxylic acid tert-butyl ester (147 mg, 0.43 mmol, 97%). LC-MS (LCT2) m/z 366 [M+Na$^+$], R$_t$ 16.63 min.

86B. 4-Aminomethyl-4-tert-butoxycarbonylamino-piperidine-1-carboxylic acid tert-butyl ester A 1M solution of borane complex in THF (2.25 mL, 2.25 mmol) was added to a cooled solution (0° C.) of 4-tert-butoxycarbonylamino-4-carbamoyl-piperidine-1-carboxylic acid tert-butyl ester (107 mg, 0.3 mmol) in THF (4.3 mL). After stirring for 5 minutes at 0° C. the reaction mixture was allowed to warm to room temperature. The reaction mixture was further warmed to 60° C. and stirred overnight. The reaction mixture was cooled to room temperature and methanol (5.1 mL) was added. After stirring for 30 minutes, the solvents were removed by evaporation. The reaction mixture was partitioned between an aqueous saturated solution of ammonium chloride (10 mL) and dichloromethane (10 mL). After further extraction of the aqueous phase with dichloromethane (20 mL), the combined organic phases were dried (Mg$_2$SO$_4$), filtered and concentrated. Flash column chromatography on silica, eluting with 5% methanol in dichloromethane, gave 4-aminomethyl-4-tert-butoxycarbonylamino-piperidine-1-carboxylic acid tert-butyl ester (5.5 mg, 0.017 mmol, 6%). LC-MS (LCT2) m/z 352 [M+Na$^+$], R$_t$ 7.16 min.

86C. 4-tert-Butoxycarbonylamino-4-[(4-chloro-benzoylamino)-methyl]-piperidine-1-carboxylic acid tert-butyl ester To a solution of 4-aminomethyl-4-tert-butoxycarbonylamino-piperidine-1-carboxylic acid tert-butyl ester (12.2 mg, 0.037 mmol) and triethylamine (16 µL, 0.12 mmol) in dry dichloromethane (4 mL) was added 4-chlorobenzoyl chloride (5 µL, 0.037 mmol). After stirring for 18 hours at room temperature, the reaction mixture was partionated between dichloromethane (2 mL) and water (1 mL) with 10% aqueous sodium hydroxide (0.1 mL). The two layers were separated and the aqueous phase was further extracted with dichloromethane (2 mL). The combined organic layers were dried (Mg$_2$SO$_4$), filtered and concentrated. Preparative TLC, eluting with 10% methanol-dichloromethane, gave 4-tert-butoxycarbonylamino-4-[(4-chloro-benzoylamino)-methyl]-piperidine-1-carboxylic acid tert-butyl ester (6 mg, 0.013 mmol, 35%). LC-MS (LCT2) m/z 490 [M+Na$^+$], R$_t$ 8.20 min.

86D. N-(4-Amino-piperidin-4-ylmethyl)-4-chloro-benzamide dihydrochloride

A 4M solution of HCl in dioxane (0.3 ml, 1.2 mmol) was added dropwise to a solution of 4-tert-butoxycarbonylamino-4-[(4-chloro-benzoylamino)-methyl]-piperidine-1-carboxylic acid tert-butyl ester (5.8 mg, 0.012 mmol) in methanol (0.5 mL). The solution was stirred at room temperature for 17 hours. The solvents were concentrated to give N-(4-amino-piperidin-4-ylmethyl)-4-chloro-benzamide dihydrochloride (6.1 mg, quantitative) that was used in the next step without further purification. $^1$H NMR (CD$_3$OD) δ 2.23-2.30 (4H, m), 3.46-3.61 (4H, m), 3.89 (2H, s), 7.58 (2H, d, J=7 Hz), 8.03 (2H, d, J=7 Hz).

86E. N-[4-Amino-1-(7H-pyrrolo[2,3-d]pyrimidin-4-yl)-piperidin-4-ylmethyl]-4-chloro-benzamide A degassed mixture of crude N-(4-amino-piperidin-4-ylmethyl)-4-chloro-benzamide dihydrochloride (6.1 mg), 4-chloro-7H-pyrrolo[2,3-d]pyrimidine (2.6 mg, 0.016 mmol), triethylamine (16 µL, 0.09 mmol) and n-butanol (0.3 mL) was stirred at 100° C. for 17 hours. The solvents were concentrated. The crude mixture was first purified on an SCX-II acidic resin, eluting with methanol then 2M ammonia-methanol, and then by preparative TLC, eluting with 15% methanol-dichloromethane, to give N-[4-amino-1-(7H-pyrrolo[2,3-d]pyrimidin-4-yl)-piperidin-4-ylmethyl]-4-chloro-benzamide (3.3 mg, 0.009 mmol, 69% over 2 steps). LC-MS (LCT2) m/z 385 [M+H$^+$], R$_t$ 2.58 min.

$^1$H NMR (CD$_3$OD) δ 1.79-1.81 (2H, m), 1.95-1.97 (2H, m), 3.67 (2H, s), 4.20-4.17 (4H, m), 6.72 (1H, d, J=5 Hz), 7.23 (1H, d, J=5 Hz), 7.58 (2H, d, J=7 Hz), 7.96 (2H, d, J=7 Hz), 8.24 (1H, s).

Examples 87 TO 90

By following the methods described above, or methods analogous thereto, the compounds of Examples 87 to 90 were prepared.

Example 87

4-Biphenyl-4-ylmethyl-1-(7H-pyrrolo[2,3-d]pyrimidin-4-yl)-piperidin-4-ylamine

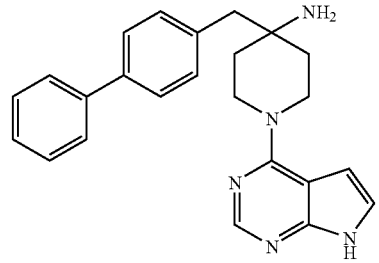 [SMILES: NC1(Cc2ccc(-c3ccccc3)cc2)CCN(c2ncnc3[nH]ccc23)CC1]

Example 88

4-Biphenyl-2-ylmethyl-1-(7H-pyrrolo[2,3-d]pyrimidin-4-yl)-piperidin-4-ylamine

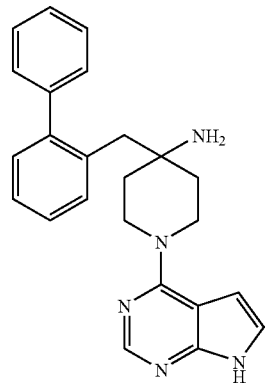 [SMILES: NC1(Cc2ccccc2-c2ccccc2)CCN(c2ncnc3[nH]ccc23)CC1]

Example 89

4-(2-Methoxy-benzyl)-1-(7H-pyrrolo[2,3-d]pyrimidin-4-yl)-piperidin-4-ylamine

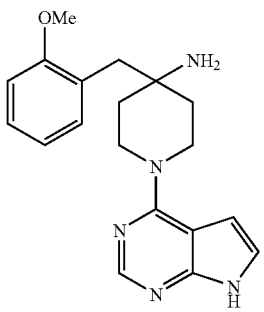 [SMILES: COc1ccccc1CC1(N)CCN(c2ncnc3[nH]ccc23)CC1]

Example 90

4-Naphthalen-1-ylmethyl-1-(7H-pyrrolo[2,3-d]pyrimidin-4-yl)-piperidin-4-ylamine

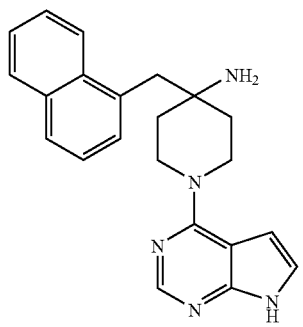 [SMILES: NC1(Cc2cccc3ccccc23)CCN(c2ncnc3[nH]ccc23)CC1]

ExampleS 91 TO 94

By following the methods described above, or methods analogous thereto, the compounds of Examples 91 to 94 are prepared.

Example 91

4-Amino-1-(7H-pyrrolo[2,3-d]pyrimidin-4-yl)-piperidine-4-carboxylic acid 4-chloro-2-fluoro-benzylamide

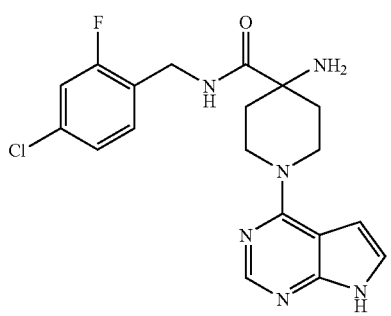 [SMILES: NC1(C(=O)NCc2ccc(Cl)cc2F)CCN(c2ncnc3[nH]ccc23)CC1]

Example 92

4-Amino-1-(7H-pyrrolo[2,3-d]pyrimidin-4-yl)-piperidine-4-carboxylic acid (biphenyl-3-ylmethyl)-amide

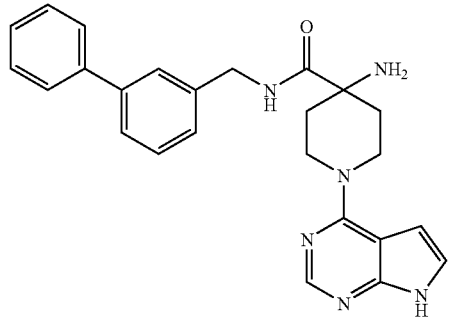 [SMILES: NC1(C(=O)NCc2cccc(-c3ccccc3)c2)CCN(c2ncnc3[nH]ccc23)CC1]

Example 93

4-Biphenyl-3-ylmethyl-1-(7H-pyrrolo[2,3-d]pyrimidin-4-yl)-piperidin-4-ylamine

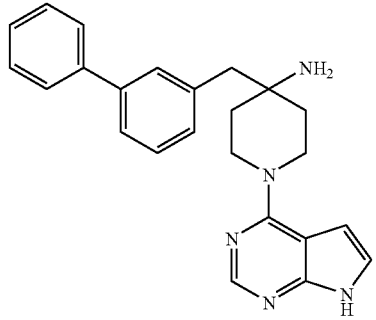 [SMILES: NC1(Cc2cccc(-c3ccccc3)c2)CCN(c2ncnc3[nH]ccc23)CC1]

Example 94

4-(6-Chloro-biphenyl-3-ylmethyl)-1-(7H-pyrrolo[2,3-d]pyrimidin-4-yl)-piperidin-4-ylamine

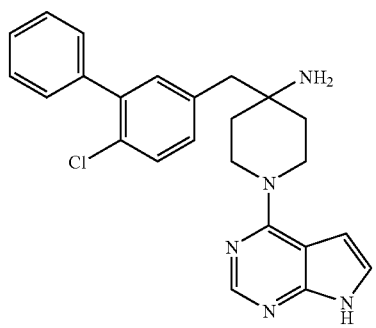 [SMILES: NC1(Cc2ccc(Cl)c(-c3ccccc3)c2)CCN(c2ncnc3[nH]ccc23)CC1]

Biological Activity

Example 95

Measurement of PKA Kinase Inhibitory Activity (IC$_{50}$)

Compounds of the invention can be tested for PK inhibitory activity using the PKA catalytic domain from Upstate Biotechnology (#14-440) and the 9 residue PKA specific peptide (GRTGRRNSI), also from Upstate Biotechnology (#12-257), as the substrate. A final concentration of 1 nM enzyme is used in a buffer that includes 20 mM MOPS pH 7.2, 40 µM ATP/γ$^{33}$P-ATP and 50 mM substrate. Compounds are added in dimethylsulphoxide (DMSO) solution to a final DMSO concentration of 2.5%. The reaction is allowed to proceed for 20 minutes before addition of excess orthophosphoric acid to quench activity. Unincorporated γ$^{33}$P-ATP is then separated from phosphorylated proteins on a Millipore MAPH filter plate. The plates are washed, scintillant is added and the plates are then subjected to counting on a Packard Topcount.

The % inhibition of the PKA activity is calculated and plotted in order to determine the concentration of test compound required to inhibit 50% of the PKA activity (IC$_{50}$).

Following the protocol described above, the IC$_{50}$ values of the compounds of Examples 1, 3, 6, 8, 10, 11, 12, 13, 14, 17-20, 25, 26, 28, 31-32, 38, 40, 42 and 44 have been found to be less than 10 µM whilst the compounds of Examples 4, 5, 7 and 9 each have IC$_{50}$ values of less than 50 µM.

Example 96

Measurement of PKB Kinase Inhibitory Activity (IC$_{50}$)

The inhibition of protein kinase B (PKB) activity by compounds can be determined essentially as described by Andjelkovic et al. (Mol. Cell. Biol. 19, 5061-5072 (1999)) but using a fusion protein described as PKB-PIF and described in full by Yang et al (Nature Structural Biology 9, 940-944 (2002)). The protein is purified and activated with PDK1 as described by Yang et al. The peptide AKTide-2T (H-A-R-K-R-E-R-T-Y-S-F-G-H-H-A-OH) obtained from Calbiochem (#123900) is used as a substrate. A final concentration of 0.6 nM enzyme is used in a buffer that includes 20 mM MOPS pH 7.2, 30 µM ATP/γ$^{33}$P-ATP and 25 µM substrate.

Compounds are added in DMSO solution to a final DMSO concentration of 2.5%. The reaction is allowed to proceed for 20 minutes before addition of excess orthophosphoric acid to quench activity. The reaction mixture is transferred to a phosphocellulose filter plate where the peptide binds and the unused ATP is washed away. After washing, scintillant is added and the incorporated activity measured by scintillation counting.

The % inhibition of the PKB activity is calculated and plotted in order to determine the concentration of test compound required to inhibit 50% of the PKB activity (IC$_{50}$).

Following the protocol described above, the IC$_{50}$ values of the compounds of Examples 1 to 4, 6, 8 and 10 to 52 have been found to be less than 10 µM whilst the compounds of Examples 5, 7 and 9 each have IC$_{50}$ values of less than 50 µM.

Example 97

Anti-Proliferative Activity

The anti-proliferative activities of compounds of the invention are determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. All cell lines are obtained from ECACC (European Collection of cell Cultures) or ATCC.

In particular, compounds of the invention were tested against the PC3 cell line (ATCC Reference: CRL-1435) derived from human prostate adenocarcinoma. Many compounds of the invention were found to have IC$_{50}$ values of less than 25 µM in this assay and preferred compounds have IC$_{50}$ values of less than 15 µM.

Pharmaceutical Formulations

Example 98

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

(iv) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:
1. A compound of the formula (Ic):

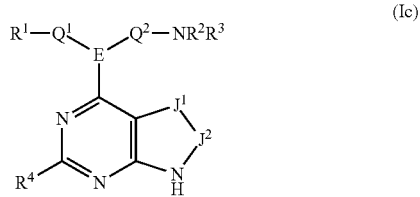

or salts, tautomers or N-oxides thereof, wherein;
$J^1$-$J^2$ J represents a group selected from $(R^8)_2C$—C(O) and $(R^7)C$=$C(R^6)$;
E is a monocyclic carbocyclic or heterocyclic group of 5 or 6 ring members wherein the heterocyclic group contains up to 3 heteroatoms selected from O, N and S;
$Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety; and wherein the carbon atoms of the linker group $Q^1$ may optionally bear one or more substituents selected from fluorine and hydroxy;
$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom a with respect to the $NR^2R^3$ group; and provided that when E is aryl or heteroaryl, then $Q^2$ is other than a bond;
$R^1$ is an aryl or heteroaryl group which is unsubstituted or is substituted by one or more substituents $R^{10}$ selected from halogen, hydroxy, trifluoromethyl, cyano, nitro, carboxy, amino, mono- or di-$C_{1-4}$ hydrocarbylamino, unsubstituted or substituted carbocyclic and heterocyclic groups having from 3 to 12 ring members; a group $R^a$-$R^b$ wherein $R^a$ is a bond, O, CO, $X^1C(X^2)X^1$, $X^1C(X^2)X^1$, $X^1C(X^2)X^1$, S, SO, SO$_2$, $NR^c$, SO$_2NR^c$ or $NR^cSO_2$; and $R^b$ is selected from hydrogen, unsubstituted or substituted carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, unsubstituted or substituted carbocyclic and heterocyclic groups having from 3 to 12 ring members and wherein one or more carbon atoms of the $C_{1-8}$ hydrocarbyl group may optionally be replaced by O, S, SO, SO$_2$, $NR^c$, $X^1C(X^2)$, $C(X^2)X^1$ or $X^1C(X^2)X^1$;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, cyano, amino, methylamino, dimethylamino, methoxy and a monocyclic or bicyclic aryl or heteroaryl group;
or $R^2$ and $R^3$ together with the nitrogen atom to which they are attached form a saturated monocyclic heterocyclic group having 4-7 ring members and optionally containing a second heteroatom ring member selected from O and N;
or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;
or $NR^2R^3$ and a carbon atom of linker group $Q^2$ to which it is attached together form a cyano group; and
$R^4$, $R^6$ and $R^8$ are each independently selected from hydrogen, halogen, $C_{1-5}$ saturated hydrocarbyl, cyano, CONH$_2$, CONHR$^9$, CF$_3$, NH$_2$, NHCOR$^9$ and NHCONHR$^9$;
$R^7$ is selected from hydrogen, halogen, $C_{1-5}$ saturated hydrocarbyl, cyano and CF$_3$;
$R^9$ is phenyl or benzyl each optionally substituted by one or more substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, SO$_2$, $NR^c$, SO$_2NR^c$ or $NR^cSO_2$; and $R^b$ is selected from hydrogen, unsubstituted or substituted carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, unsubstituted or substituted carbocyclic and heterocyclic groups having from 3 to 12 ring members and wherein one or more carbon atoms of the $C_{1-8}$ hydrocarbyl group may optionally be replaced by O, S, SO, SO$_2$, $NR^c$, $X^1C(X^2)$, $C(X^2)X^1$ or $X^1C(X^2)X^1$;
$R^c$ is selected from hydrogen and $C_{1-4}$ hydrocarbyl; and
$X^1$ is O, S or $NR^c$ and $X^2$ is =O, =S or =$NR^c$.
2. A compound according to claim 1, of the formula (Id):

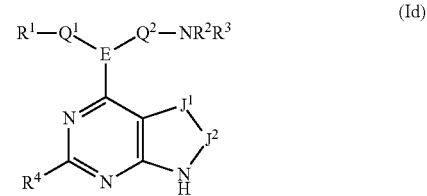

or salts, tautomers or N-oxides thereof, wherein
$Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of each linker group $Q^1$ and $Q^2$ may optionally bear one or more substituents selected from fluorine and hydroxy, provided that the hydroxy group when present is not located at a carbon atom a with respect to the $NR^2R^3$ group; and provided that when E is aryl or heteroaryl, then $Q^2$ is other than a bond; and $R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, amino, methylamino, dimethylamino, methoxy and a monocyclic or bicyclic aryl or heteroaryl group;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ and a carbon atom of linker group $Q^2$ to which it is attached together form a cyano group.

3. A compound according to claim 1 having the formula (II):

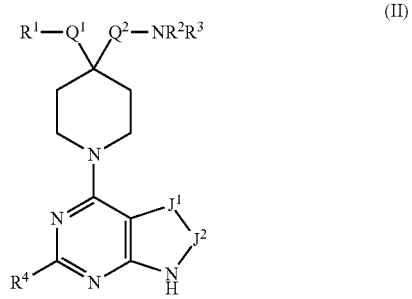

or a salt, tautomer or N-oxide thereof.

4. A compound according to claim 1 wherein $J^1$-$J^2$ is HC=CH.

5. A compound according to claim 1 wherein each of $R^6$, $R^7$ and $R^8$ when present is hydrogen.

6. A compound according to claim 1 wherein $R^2$ and $R^3$ are independently selected from hydrogen, $C_{1-4}$ hydrocarbyl and $C_{1-4}$ acyl.

7. A compound according to claim 6 wherein $NR^2R^3$ is an amino group or a methylamino group.

8. A compound according to claim 1 wherein the aryl or heteroaryl group $R^1$ is substituted by one or more substituents $R^{10c}$ selected from:
halogen,
hydroxy,
trifluoromethyl,
cyano,
amino, mono- or di-$C_{1-4}$ alkylamino,
cyclopropylamino,
monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
a group $R^a$-$R^b$;
$R^a$ is a bond, O, CO, OC(O), $NR^cC(O)$, $OC(NR^c)$, $C(O)O$, $C(O)NR^c$, S, SO, $SO_2NR^c$, $SO_2NR^c$ or $NR^cSO_2$;

$R^b$ is selected from hydrogen, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;

and $R^b$ is further selected from a $C_{1-8}$ hydrocarbyl group optionally substituted by one or more substituents selected from hydroxy, oxo, halogen, cyano, amino, mono- or di-$C_{1-4}$ alkylamino, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy, and wherein one or two carbon atoms of the $C_{1-8}$ hydrocarbyl group may optionally be replaced by O, S or $NR^c$; provided that $R^a$ is not a bond when $R^b$ is hydrogen; and $R^c$ is selected from hydrogen and $C_{1-4}$ alkyl.

9. A compound according to claim 1 wherein $R^1$ is a phenyl group which is unsubstituted or substituted by up to 5 substituents selected from hydroxy; $C_{1-4}$ acyloxy; fluorine; chlorine; bromine; trifluoromethyl; trifluoromethoxy; difluoromethoxy; benzyloxy; cyano; $C_{1-4}$ hydrocarbyloxy and $C_{1-4}$ hydrocarbyl each optionally substituted by $C_{1-2}$ alkoxy or hydroxy.

10. A compound according to claim 1, having the formula (IV):

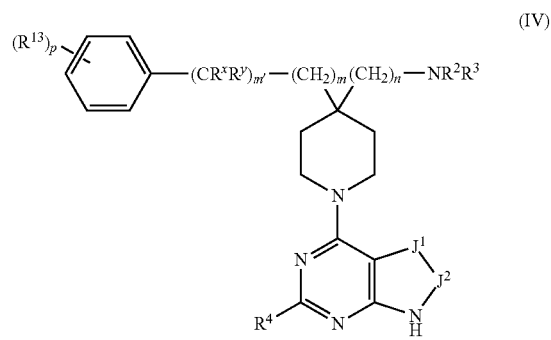

wherein m is 0, 1 or 2; m' is 0 or 1 provided that the sum of m and m' is in the range 0 to 2 and the sum of the carbon atoms in the $(CR^xR^y)_{m'}$—$(CH_2)_m$ linker is from 0 to 3; n is 0 or 1; p is 0, 1, 2 or 3; $R^x$ and $R^y$ are the same or different and each is selected from hydrogen, methyl and fluorine; and each $R^{13}$ is independently selected from $R^{10}$, $R^{10a}$, $R^{10b}$ and $R^{10c}$; wherein $R^{10}$ is selected from:
halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$;

$R^{10a}$ is selected from:

halogen, hydroxy, trifluoromethyl, cyano, nitro, carboxy, amino, mono- or di-$C_{1-4}$ hydrocarbylamino, carbocyclic and heterocyclic groups having from 3 to 7 ring members; a group $R^a$-$R^b$ wherein $R^a$ is a bond, O, CO, OC(O), $NR^cC(O)$, $OC(NR^c)$, C(O)O, C(O)$NR^c$, OC(O)O, $NR^cC(O)O$, OC(O)$NR^c$, $NR^cC(O)NR^c$, S, SO, $SO_2,NR^c$, $SO_2NR^c$ or $NR^cSO_2$; and $R^b$ is selected from hydrogen, carbocyclic and heterocyclic groups having from 3 to 7 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 7 ring members and wherein one or more carbon atoms of the $C_{1-8}$ hydrocarbyl group may optionally be replaced by O, S, SO, $SO_2$, $NR^c$, OC(O), $NR^cC(O)$, $OC(NR^c)$, C(O)O, C(O)$NR^c$, OC(O)O, $NR^cC(O)O$, OC(O)$NR^c$ or $NR^cC(O)NR^c$;

$R^c$ is selected from hydrogen and $C_{1-4}$ hydrocarbyl;

$R^{10b}$ is selected from:

halogen, hydroxy, trifluoromethyl, cyano, amino, mono- or di-$C_{1-4}$ alkylamino, cyclopropylamino, carbocyclic and heterocyclic groups having from 3 to 7 ring members; a group $R^a$-$R^b$ wherein $R^a$ is a bond, O, CO, OC(O), $NR^cC(O)$, $OC(NR^c)$, C(O)O, C(O)$NR^c$, S, SO, $SO_2,NR^c$, $SO_2NR^c$ or $NR^cSO_2$; and $R^b$ is selected from hydrogen, carbocyclic and heterocyclic groups having from 3 to 7 ring members, and a $C_{1-8}$ hydrocarbyl group optionally substituted by one or more substituents selected from hydroxy, oxo, halogen, cyano, amino, mono- or di-$C_{1-4}$ alkylamino, carbocyclic and heterocyclic groups having from 3 to 7 ring members and wherein one or more carbon atoms of the $C_{1-8}$ hydrocarbyl group may optionally be replaced by O, S, SO, $SO_2$ or $NR^c$; provided that $R^a$ is not a bond when $R^b$ is hydrogen; and $R^c$ is selected from hydrogen and $C_{1-4}$ alkyl;

$R^{10c}$ is selected from:

halogen,
hydroxy,
trifluoromethyl,
cyano,
amino, mono- or di-$C_{1-4}$ alkylamino,
cyclopropylamino,
monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
a group $R^a$-$R^b$;
$R^a$ is a bond, O, CO, OC(O), $NR^c(O)$, $OC(NR^c)$, C(O)O, C(O)$NR^c$, S, SO, $SO_2,NR^c$, $SO_2NR^c$ or $NR^cSO_2$;
$R^b$ is selected from hydrogen, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;

and $R^b$ is further selected from a $C_{1-8}$ hydrocarbyl group optionally substituted by one or more substituents selected from hydroxy, oxo, halogen, cyano, amino, mono- or di-$C_{1-4}$ alkylamino, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy, and wherein one or two carbon atoms of the $C_{1-8}$ hydrocarbyl group may optionally be replaced by O, S or $NR^c$; provided that $R^a$ is not a bond when $R^b$ is hydrogen; and $R^c$ is selected from hydrogen and $C_{1-4}$ alkyl.

11. A compound according to claim 10 wherein m is 0 or 1.

12. A compound according to claim 10 wherein $NR^2R^3$ is selected from $NH_2$, NHMe and $NMe_2$.

13. A compound according to claim 10 of the formula (V):

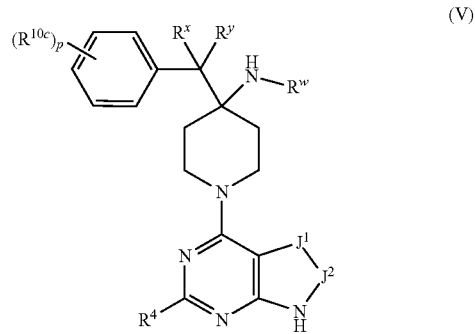

(V)

or a salt, tautomer or N-oxide thereof, wherein $R^{10c}$ is selected from:
halogen,
hydroxy,
trifluoromethyl,
cyano,
amino, mono- or di-$C_{1-4}$ alkylamino,
cyclopropylamino,
monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
a group $R^a$-$R^b$;
$R^a$ is a bond, O, CO, OC(O), $NR^c(O)$, $OC(NR^c)$, C(O)O, C(O)$NR^c$, S, SO, $SO_2,NR^c$, $SO_2NR^c$ or $NR^cSO_2$;
$R^b$ is selected from hydrogen, monocyclic carbocyclic and heterocyclic groups having from 3 to 7 ring members of which 0, 1 or 2 are selected from O, N and S and the remainder are carbon atoms, wherein the mono cyclic carbocyclic and heterocyclic groups are optionally substituted by one or more substituents selected from halogen, hydroxy, trifluoromethyl, cyano and methoxy;
and $R^b$ is further selected from a $C_{1-8}$ hydrocarbyl group optionally substituted by one or more substituents selected from hydroxy, oxo, halogen, cyano, amino, mono- or di-$C_{1-4}$ alkylamino, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy, and wherein one or two carbon atoms of the $C_{1-8}$ hydrocarbyl group may optionally be replaced by O, S or $NR^c$; provided that $R^a$ is not a bond when $R^b$ is hydrogen; and $R^c$ is selected from hydrogen and $C_{1-4}$ alkyl;

p is 1, 2 or 3;

$R^w$ is hydrogen or methyl; and $R^x$ and $R^y$ are the same or different and each is selected from hydrogen, methyl and fluorine.

14. A compound according to claim 1 of the formula (VI):

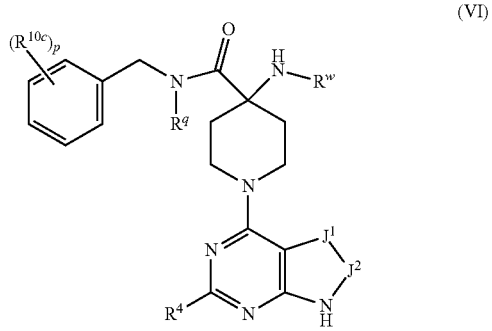

(VI)

wherein $R^q$ and $R^w$ are each independently selected from hydrogen and methyl;

p is 0, 1, 2 or 3; and each substituent $R^{10c}$ is independently selected from:
halogen,
hydroxy,
trifluoromethyl,
cyano,
amino, mono- or di-$C_{1-4}$ alkylamino,
cyclopropylamino,
monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
a group $R^a$-$R^b$;

$R^a$ is a bond, O, CO, OC(O), $NR^cC(O)$, $OC(NR^c)$, C(O)O, $C(O)NR^c$, S, SO, $SO_2$ $NR^c$ $SO_2NR^c$ or $NR^cSO_2$;

$R^b$ is selected from hydrogen, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;

and $R^b$ is further selected from a $C_{1-8}$ hydrocarbyl group optionally substituted by one or more substituents selected from hydroxy, oxo, halogen, cyano, amino, mono- or di-$C_{1-4}$ alkylamino, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy, and wherein one or two carbon atoms of the $C_{1-8}$ hydrocarbyl group may optionally be replaced by O, S or NR provided that $R^a$ is not a bond when $R^b$ is hydrogen; and $R^c$ is selected from hydrogen and $C_{1-4}$ alkyl.

15. A compound according to claim 1 of the formula (VII):

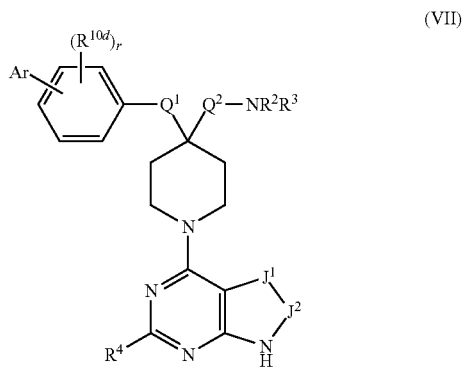

(VII)

wherein Ar is a 5- or 6-membered monocyclic aryl or heteroaryl group having up to 2 heteroatom ring members selected from O, N and S and being optionally substituted by one or two substituents selected from fluorine, chlorine, methyl and methoxy; $R^{10d}$ is a substituent selected from fluorine, chlorine, methyl, trifluoromethyl, trifluoromethoxy and methoxy; and r is 0, 1 or 2.

16. A compound according to claim 15 wherein Ar is unsubstituted phenyl.

17. A compound as defined in claim 1 in the form of a salt, or N-oxide.

18. A pharmaceutical composition comprising a compound as defined in claim 1 and a pharmaceutically acceptable carrier.

* * * * *

UNITED STATES PATENT AND TRADEMARK OFFICE
CERTIFICATE OF CORRECTION

PATENT NO. : 8,546,407 B2
APPLICATION NO. : 11/577963
DATED : October 1, 2013
INVENTOR(S) : Valerio Berdini et al.

Page 1 of 1

It is certified that error appears in the above-identified patent and that said Letters Patent is hereby corrected as shown below:

In the Claims:

Column 150, Line 58: Delete "mono cyclic" and insert -- monocyclic --

Column 152, Line 16: Delete "NR" and insert -- $NR^c$ --

Signed and Sealed this
Seventeenth Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,546,407 B2 | Page 1 of 1 |
| APPLICATION NO. | : 11/577963 | |
| DATED | : October 1, 2013 | |
| INVENTOR(S) | : Berdini et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1924 days.

Signed and Sealed this
Eleventh Day of November, 2014

Michelle K. Lee
*Deputy Director of the United States Patent and Trademark Office*